United States Patent

Hayashi et al.

[11] 4,069,387
[45] Jan. 17, 1978

[54] 16-CHLORO-SUBSTITUTED PROSTAGLANDINS AND DERIVATIVES THEREOF

[75] Inventors: Masaki Hayashi; Seiji Kori; Katsuichi Shimoji, all of Takatsuki, Japan

[73] Assignee: Ono Pharmaceutical Company, Osaka, Japan

[21] Appl. No.: 709,847

[22] Filed: July 29, 1976

[30] Foreign Application Priority Data

Aug. 8, 1975 United Kingdom ............... 33235/75

[51] Int. Cl.² ........................................... C07C 177/00
[52] U.S. Cl. .......................... 560/121; 260/345.8 P; 260/448.8 R; 260/514 D; 260/586 R; 260/617 R; 424/305; 424/317; 536/112; 542/426
[58] Field of Search ...................... 260/468 D, 514 D

[56] References Cited

U.S. PATENT DOCUMENTS

| 3,962,293 | 6/1976 | Magerlin .......................... 260/408 |
| 4,024,174 | 5/1977 | Hayashi et al. ..................... 260/468 |

Primary Examiner—Robert Gerstl
Attorney, Agent, or Firm—Albert H. Graddis; Frank S. Chow

[57] ABSTRACT

The present invention relates to compounds of the formula:

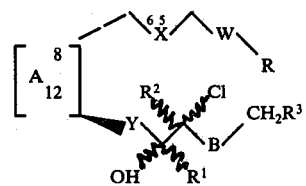

wherein A represents a grouping of the formula:

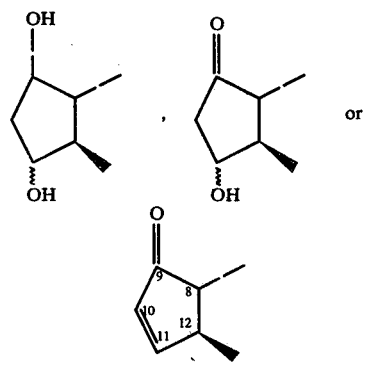

B represents a single bond or a straight- or branched-chain alkylene group containing from 1 to 9 carbon atoms, W represents ethylene or trans-vinylene, X represents ethylene or cis-vinylene, Y represents ethylene or trans-vinylene, R represents a hydroxymethyl group or a grouping of the formula $-COOR^4$, in which $R^4$ represents a hydrogen atom or a straight- or branched-chain alkyl group containing from 1 to 12 carbon atoms, $R^1$ represents a hydrogen atom or a methyl or ethyl group, $R^2$ represents a hydrogen atom or a methyl or ethyl group and $R^3$ represents a hydrogen or chlorine atom or a hydroxy group and cyclodextrin clathrates of such alcohols, acids and esters and, when $R^4$ in the formula $-COOR^4$ represents a hydrogen atom, nontoxic salts thereof, and intermediates therefor. These compounds exhibit characteristic prostaglandin-like activity.

10 Claims, No Drawings

16-CHLORO-SUBSTITUTED PROSTAGLANDINS AND DERIVATIVES THEREOF

This invention is concerned with new prostaglandin analogues.

Prostaglandins are derivatives of prostanoic acid which has the following formula:

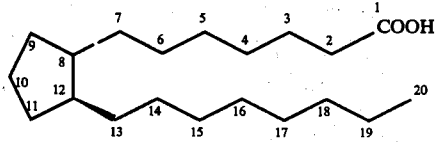

I

Various types of prostaglandins are known, the types depending inter alia on the structure and substituents on the alicyclic ring. For example, the alicyclic rings of prostaglandins F(PGF), E(PGE) and A(PGA) have the structures:

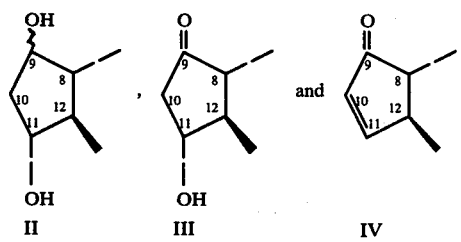

II   III   IV respectively. The dotted lines in the foregoing formulae and in other formulae throughout this specification denote, in accordacne with generally accepted rules of nomenclature, that the attached grouping lies behind the general plane of the ring system, i.e. that the grouping is in α-configuration, the thickened lines ◣ denote that the grouping lies in front of the general plane of the system, i.e. that the grouping is in β-configuration, and the wavy line ∼ indicates the grouping is in α- or β- configuration.

Such compounds are sub-classified according to the position of double bond(s) in the side chain(s) attached to the 8- and 12- positions of the alicyclic ring. Thus $PG_1$ compounds have a trans-double bond between $C_{13}$–$C_{14}$ (trans-$\Delta^{13}$) and $PG_2$ compounds have a cis-double bond between $C_5$–$C_6$ and a trans-double bond between $C_{13}$–$C_{14}$(cis-$\Delta^5$, trans-$\Delta^{13}$). For example, prostaglandin $F_{1\alpha}$(PGF$_{1\alpha}$) and prostaglandin $E_1$ (PGE$_1$) are charcterized by the following structures V and VI.

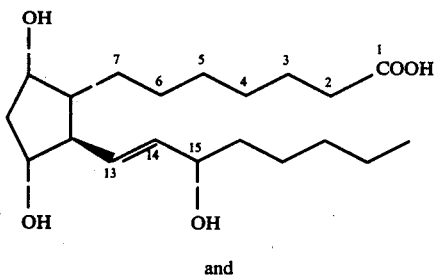

V and

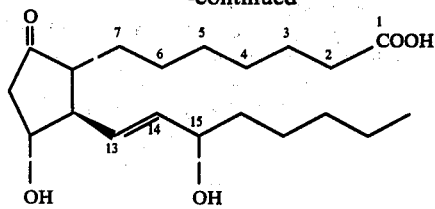

VI respectively. The structure of PGF$_{2\alpha}$ and PGE$_2$, as members of the PG$_2$ group, correspond to those of formulae V and VI respectively with a cis-double bond between the carbon atoms in positions 5 and 6. Compounds in which the double bond between the carbon atoms in positions 13 and 14 of members of the PG$_1$ group is replaced by ethylene are known as dihydro-prostaglandins, e.g. dihydro-prostaglandin-F$_{1\alpha}$(dihydro-PGF$_{1\alpha}$) and dihydro-prostaglandin-E$_1$ (dihydro-PGE$_1$).

Moreover, when one or more methylene groups are added to, or eliminated from, the aliphatic group attached to the 12-position of the alicyclic ring of the prostaglandins the compounds are known, in accordance with the usual rules of organic nomenclature, a homoprostaglandins (methylene group added) or non-prostaglandins (methylene group eliminated), and, when more than one methylene group is added or eliminated, the number is indicated by di-, tri- etc. before the prefix "homo" or "nor."

Prostaglandins are generally known to possess pharmacological properties, for example they stimulate smooth muscle, have hypotensive, diuretic, bronchodilating and antilipolytic activities, and als inhibit blood platelet aggregation and gastric acid secretion, and are, accordingly, useful in the treatment of hypertension, thrombosis, asthma and gastro-intestinal ulcers, in the induction of labour and abortion in pregnant female mammals, in the prevention of arteriosclerosis, and as diuretic agents. They are fat-soluble substances obtainable in very small quantities from various tissues of animals which secrete the prostaglandins in the living body.

For example, PGEs and PGAs have an inhibiting effect on gastric acid secretion and may, accordingly, be used in the treatment of gastric ulcers. They also inhibit the release of free fatty acid induced by epinephrine and as a result they reduce the concentration of free fatty acid in blood, and are, accordingly, useful in the prevention of arteriosclerosis and hyperlipemia. PGE$_1$ inhibits blood platelet aggregation and also removes the thrombus and prevents thrombosis. PGEs and PGFs have a stimulating effect on smooth muscle and increase the intestinal peristalsis; these actions indicate therapeutic utility on post-operative ileus and as purgatives. Furthermore, PGEs and PGEs may be used as oxytocics, as abortifacients in the first and second trimesters; in the post-labour abortion of the placenta, and as oral contraceptives because they regulate the sexual cycle of female mammals. PGEs and PGAs have vasodilator and diuretic activities. PGEs are useful for improvement in patients suffering from cerebral vascular disease because they increase the cerebral blood flow, and are also useful in the treatment of asthmatic conditions in patients because of their bronchodilating activity.

During the past decade widespread investigations have been carried out in order to discover inter alia new products possessing the pharmacological properties of the 'natural' prostaglandins or one or more of such proprties to an enhanced degree. It has now been found that by introducing a chlorine atom on the carbon atom in the 16-position of prostaglandins F, E and A and certain analogues thereof, new prostaglandin analogues are obtained which possess the pharmacological properties of the 'natural' prostaglandins and are, in some aspects of their activities, an improvement, for example they possess an enhanced strength of activity and/or a prolonged duration of activity.

The present invention accordingly provides the new prostaglandin analogues of the general formula:

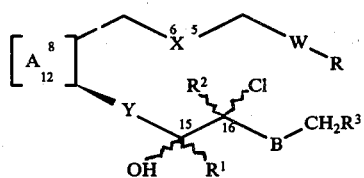

(wherein A represents a grouping of formula IV as indicated hereinbefore or a grouping of the formula:

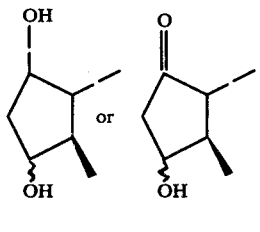

B represents a single bond or a straight- or branched-chain alkylene group containing from 1 to 9 (preferably 1 to 5) carbon atoms, W represents ethylene (i.e. —$CH_2Ch_2$—) or trans-vinylene (i.e.

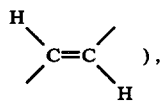

X represents ethylene or cis-vinylene (i.e.

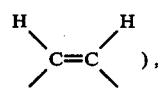

Y represents ethylene or trans-vinylene, R represents a hydroxymethyl group (i.e. —$CH_2OH$) or a grouping of the formula —$COOR^4$, in which $R^4$ represents a hydrogen atom or a straight- or branched-chain alkyl group containing from 1 to 12 carbon atoms, $R^1$ represents a hydrogen atom or a methyl or ethyl group, $R^2$ represents a hydrogen atom or a methyl or ethyl group and $R^3$ represents a hydrogen or chlorine atom or a hydroxy group) and cyclodextrin clathrates of such alcohols, acids and esters and, when $R^4$ in the formula —$COOR^4$ represents a hydrogen atom, non-toxic (e.g. sodium) salts thereof.

Preferably A represents a group of formula VIIIA or VIIIB, preferably B represents the n-propyl group, preferably W represents ethylene, preferably Y represents trans-vinylene, preferably R represents the carboxy or methoxycarbonyl group, preferably $R^1$ represents a hydrogen atom or a methyl group, preferably $R^2$ represents a hydrogen atom or a methyl group, preferably $R^3$ represents a hydrogen atom, and preferably the hydroxy groups depicted in formulae VII, VIIIA and VIIIB in α- or β-configuration are attached to the carbon atom in α-configuration.

The present invention is concerned with all compounds of general formula VII in the 'natural' form or its enantiomeric form, or mixtures thereof, more particularly the racemic form, consisting of equimolecular mixtures of natural and its enantiomeric form.

As will be apparent to those skilled in the art, the compounds depicted in general formula VII have at least four centres of chirality, these four centres of chirality being at the alicyclic ring carbon atoms of group A identified as 8 and 12 and at the $C_{15}$ and $C_{16}$ carbon atoms which have attached to them a hydroxy group and a chlorine atom respectively. Still further centres of chirality occurs when the alicyclic group A carries a hydroxy group on the carbon atom in position 11 (i.e. when the ring is that of formula VIIIB) or hydroxy groups in positions 9 and 11 (i.e. when the ring is that of formula VIIIA), and other centres of chirality may occur when B is a branched-chain alkylene group. The presence of chirality leads, as is well known, to the existence of isomerism. However, the compounds of general formula VII all have such a configuration that the side-chains attached to the ring carbon atoms in the positions identified as 8 and 12 are trans with respect to each other. Accordingly, all isomers of general formula VII, and mixtures thereof, which have those side-chains attached to the ring carbon atoms in positions 8 and 12 in the trans-configuration are to be considered within the scope of general formula VII.

According to a feature of the present invention, the prostaglandin analogues of general formula VII, wherein A represents a grouping of formula VIIIA or VIIIB, R represents a grouping of the formula — $COOR^5$ in which $R^5$ represents a hydrogen atom or a straight- or branched-chain alkyl group containing from 1 to 4 carbon atoms, $R^3$ represents a hydrogen atom or a hydroxy group, and the other symbols are as hereinbefore defined, i.e. compounds of the general formula:

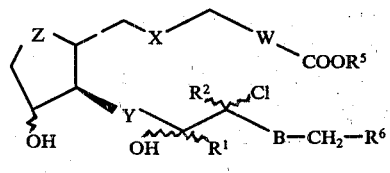

(wherein Z represents

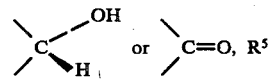

represents a hydrogen atom or a straight- or branched-chain alkyl group containing from 1 to 4 carbon atoms, $R^6$ represents a hydrogen atom or a hydroxy group, and the other symbols are as hereinbefore defined) are prepared by the process which comprises hydrolyzing to hydroxy groups the groups $OR^7$, $OR^8$ (when $R^8$ is other than a hydrogen atom) and $R^9$ (when $R^9$ is other than a hydrogen atom) of a compound of the general formula:

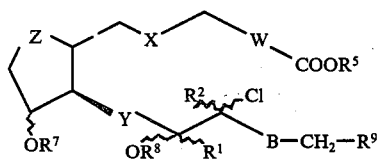 IX wherein R[7] represents a 2-tetrahydropyranyl group unsubstituted or substituted by at least one alkyl group, or a 2-tetrahydrofuranyl or 1-ethoxyethyl group, R[8] represents a hydrogen atom or a 2-tetrahydropyranyl group unsubstituted or substituted by at least one alkyl group, or a 2-tetrahydrofuranyl or 1-ethoxyethyl group, R[9] represents a hydrogen atom or a grouping of the formula —OR[7], in which R[7] is as hereinbefore defined, and the other symbols are as hereinbefore defined. Preferably the symbols R[7] represent the 2-tetrahydropyranyl group, and preferably the symbol R[8], when other than a hydrogen atom, also represents the 2-tetrahydropyranyl group.

The groups OR[7], OR[8] (when R[8] is other than a hydrogen atom) and R[9] (when R[9] is other than a hydrogen atom) of the compounds of general formula IX may be converted to hydroxy groups by mild hydrolysis with an aqueous solution of an organic acid, e.g. acetic acid, or with a dilute aqueous inorganic acid, e.g. hydrochloric acid, advantageously in the presence of a water-miscible organic solvent, e.g., tetrahydrofuran or an alkanol containing from 1 to 4 carbon atoms, e.g. methanol. The mild hydrolysis may be carried out at a temperature ranging from ambient to 70° C (preferably at a temperature below 45°) with an acid mixture, e.g. a mixture of hydrochloric acid with tetrahydrofuran or methanol, or a mixture of acetic acid, water and tetrahydrofuran. The products of formula VIIA may be purified by column chromatography on silica gel, which procedure may, when the starting material of formula IX is a mixture of compounds with the group OR[8] in the 15-position in α- and β- configurations, lead to a separation of the resulting 15α-hydroxy and 15β-hydroxy isomers of formula VIIA.

If desired, acids of general formula VIIA, wherein R[5] represents a hydrogen atom and the other symbols are as hereinafter defined, may be prepared by treatment of corresponding esters of that formula, viz. compounds wherein R[5] represents an alkyl group containing from 1 to 4 carbon atoms, (1) when Z represents

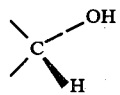

with an aqueous solution of an alkali metal, e.g. sodium or potassium, hydroxide or carbonate in the presence of a wter-miscible organic solvent, e.g. tetrahydrofuran or an alkanol containing from 1 to 4 carbon atoms, e.g. methanol, or (2) when Z represents

with bakers's yeast [cf, C.J. Sih et al, J. Amer. Chem. Soc. 94, 3643–3644 (1972)].

The PGE compounds of general formula VIIA wherein Z represents

may be converted to the corresponding PGA compounds of general formula VII, wherein A represents a grouping of formula IV, by subjecting the PGEs to dehydration using an aqueous solution of an organic or inorganic acid having a higher concentration than that employed for hydrolyzing the groups OR[7] or compounds of general formula IX, e.g. 1N hydrochloric acid or acetic acid, and heating at a temprature of 30° to 60° C. If desired, simultaneous hydrolysis and dehydration under acid conditions as hereinbefore described may be effected on compounds of general formula IX, wherein Z represents

and the other symbols are as hereinbefore defined, to produce directly PGA compounds of formula VII wherein A represents a grouping of formula IV.

Compounds of general formula VIIA, wherein W, X and Y each represent an ethylene group and the other symbols are as hereinbefore defined, may be prepared from compounds of general formula VIIA, wherein W represents an ethylene or trans-vinylene group, X represents an ethylene or cis-vinylene group, Y represents a trans-vinylene group and the other symbols are as hereinbefore defined, by reduction. Suitably, the reduction may be effected by hydrogenation in the presence of a hydrogenation catalyst, e.g. palladium on charcoal, palladium black or platinum dioxide, in an inert organic solvent, for example a lower alkanol, e.g. methanol or ethanol, at laboratory temperature at normal or elevated pressure, for example at a hydrogen pressure from atmospheric to 15 kg./cm².

Compounds of general formula VII, wherein A represents a grouping of formula VIIIA or VIIIB, R represents a grouping of the formula —COOR[5] in which R[5] is as hereinbefore defined, R[3] represents a chlorine atom, and the other symbols are as hereinbefore defined, i.e. compounds of the general formula:

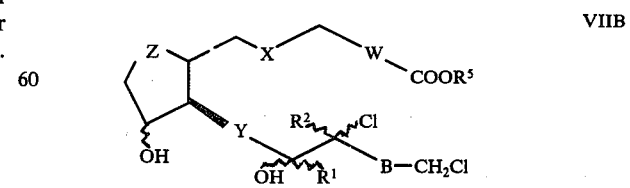 VIIB (wherein the various symbols are as hereinbefore defined), may be prepared from a compound of general formula:

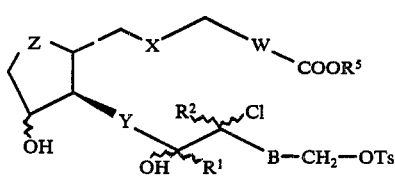

(wherein Ts represents the tosyl group, and the other symbols are as hereinbefore defined) by chlorination. The chlorination may be suitably carried out by methods known per se, for example with lithium chloride in N,N-dimethylformamide at room temperature. By the term "methods known per se" as used in this specification is meant methods heretofore used or described in the chemical literature.

Compounds of general formula X may be prepared from compounds of general formula VIIA, wherein $R^6$ represents a hydroxy group and the other symbols are as hereinbefore defined, by tosylation with tosyl chloride in an inert organic solvent, e.g. methylene chloride, in the presence of a base, e.g. pyridine or triethylamine, at a temperature ranging from ambient to 0° C.

Compounds of general formula IX, wherein Z represents

$R^8$ is other than a hydrogen atom and the other symbols are as hereinbefore defined, i.e. compounds of the general formula:

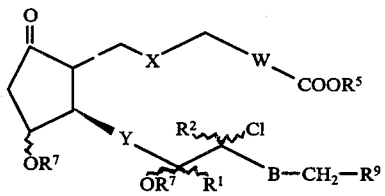

(wherein the various symbols are as hereinbefore defined) may be prepared from compounds of general formula IX, wherein Z represents

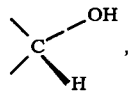

$R^8$ is other than a hydrogen atom, and the other symbols are as hereinbefore defined), by methods known per se for the conversion of a hydroxy group in the 9-position of a prostaglandin compound to an oxo group, for example by means of a chromic acid solution (obtained from chromium trioxide, manganese sulphate and sulphuric acid in water), Jones' reagent or a dimethyl sulphide-N-chlorosuccinimide complex.

Compounds of general formula IX, wherein Z represents

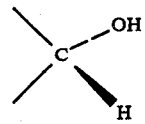

and the other symbols are as hereinbefore defined, i.e. compounds of the general formula:

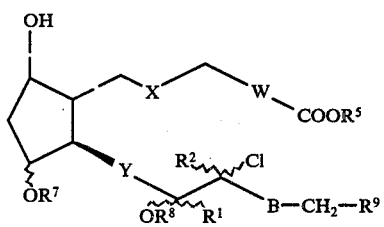

(wherein the various symbols are as hereinbefore defined), may be prepared from a compound of the general formula:

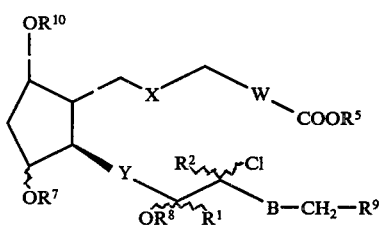

(wherein $R^{10}$ represents an alkylcarbonyl group containing from 2 to 5 carbon atoms, and the other symbols are as hereinbefore defined) by hydrolysis under alkaline conditions. The hydrolysis under alkaline conditions may be effected (1) with an aqueous solution of an alkali metal, e.g. sodium or potassium, hydroxide or carbonate in the presence of a water-miscible solvent, e.g. tetrahydrofuran or an alkanol containing from 1 to 4 carbon atoms, to give a compound of general formula IXB wherein $R^5$ represents a hydrogen atom, or (2) with anhydrous potassium carbonate in an anhydrous alkanol containing from 1 to 4 carbon atoms, preferably absolute methanol, to give a compound of general formula IXB wherein $R^5$ represents an alkyl group containing from 1 to 4 carbon atoms.

Compounds of general formula IXB, wherein W and X each represent an ethylene group, Y represents a transvinylene group and the other symbols are as hereinbefore defined, may be prepared from compounds of general formula IXB, wherein W and/or X represent(s) a vinylene group, Y represents a trans-vinylene group and the other symbols are as hereinbefore defined, by reduction. Suitably, the reduction may be effected by hydrogenation in the presence of a hydrogenation catalyst, e.g. palladium on charcoal or palladium black, in an inert organic solvent, for example a lower alkanol, e.g. methanol or ethanol, at laboratory temperature at normal or elevated pressure, for example at a hydrogen pressure from atmospheric to 15 kg./cm².

Compounds of general formula XI, wherein $R^8$ is other than a hydrogen atom and the other sumbols are as hereinbefore defined, i.e. compounds of the general formula:

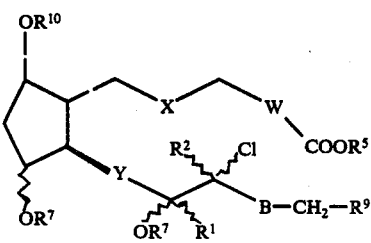

XIA (wherein the various symbols are as hereinbefore defined), may be prepared from compounds of general formula XI wherein $R^8$ represents a hydrogen atom and the other symbols are as hereinbefore defined, i.e. compounds of the general formula:

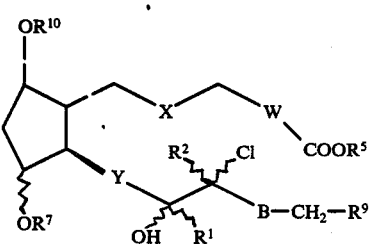

XIB (wherein the various symbols are as hereinbefore defined), by reaction with a dihydropyran, dihydrofuran or ethyl vinyl ether in an inert organic solvent, e.g. methylene chloride, in the presence of a condensing agent, e.g. p-toluenesulphonic acid.

Compounds of general formula XIB, wherein Y represents a trans-vinylene group, $R^1$ represents a hydrogen atom and the other symbols are as hereinbefore defined, i.e. compounds of the general formula

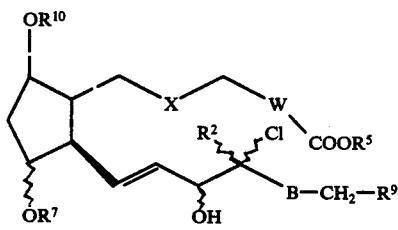

XIC (wherein the various symbols are as hereinbefore defined), may be prepared from a compound of the general formula:

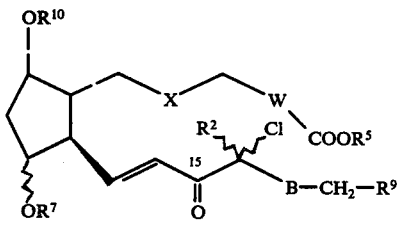

XII (wherein the various symbols are as hereinbefore defined) by reduction to convert the 15-oxo group to a hydroxy group. The reduction is suitably effected (1) with excess sodium borohydride in an alkanol containing from 1 to 4 carbon atoms, e.g. methanol, at a low temperature, preferably at −30° to −60° C., or (2) with zinc borohydride in a suitable inert organic solvent, e.g. 1,2-dimethoxyethane, at −10° to 10° C. The product thus obtained is a mixture of isomers in which the hydroxy group at position 15 is in α- or β-configuration. If desired, the isomer having the hydroxy group in α-configuration may be separated from the isomer having the hydroxy group in β-configuration by column chromatography of the mixture on silica gel.

Compounds of general formula XIB, wherein Y represents a trans-vinylene group, $R^1$ represents a methyl or ethyl group and the other symbols are as hereinbefore defined, i.e. compounds of the general formula:

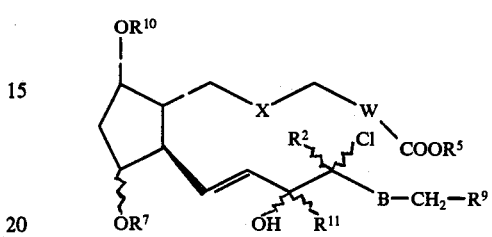

XID (wherein $R^{11}$ represents a methyl or ethyl group and the other symbols are as hereinbefore defined) may be prepared from compounds of general formula XII by treatment with an organometallic compound of the general formula:

$R^{11}$-Met         XIII (wherein Met represents a lithium atom or a magnesium halide group and $R^{11}$ is as hereinbefore defined) in an inert organic solvent, e.g. diethyl ether, tetrahydrofuran or n-hexane, at a low temperature, preferably below 0° C., more particularly in the case of an organolithium compound below −20° C., followed by hydrolysis of the resulting organometallic compound, for example by treatment with water or an aqueous solution of ammonium chloride or an acid, e.g. hydrochloric acid or oxalic acid, to give a mixture of the α- and β-hydroxy isomers of compounds of general formula XID.

Compounds of general formula XIB, wherein W, X and Y each represent an ethylene group and the other symbols are as hereinbefore defined, may be prepared from compounds of general formula XIC or XID by reduction.

Suitably, the reduction may be effected by hydrogenation in the presence of a hydrogenation catalyst, e.g. palladium on charcoal, palladium black or platinum dioxide, in an inert organic solvent, for example a lower alkanol, e.g. methanol or ethanol, at laboratory temperature at normal or elevated pressure, for example at a hydrogen pressure from atmospheric to 15 kg./cm².

Compounds of general formula IXB, wherein the various symbols are as hereinbefore defined, may be converted to compounds of the general formula:

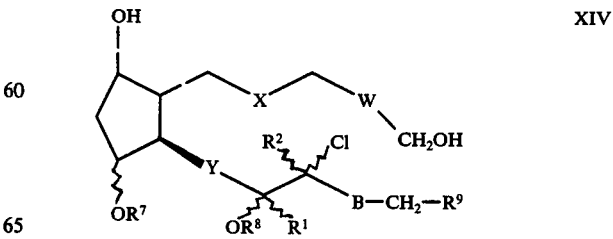

XIV (wherein the various symbols are as hereinbefore defined) by methods known per se for the conversion of an alkoxycarbonyl group to a hydroxymethyl group, for example by treatment with diisobutylaluminium hydride in an inert organic solvent, e.g. toluene or tetrahydrofuran, at a low temperature, e.g. at $-78°$ C.

Compounds of general formula XIV may be converted to compounds of the general formula:

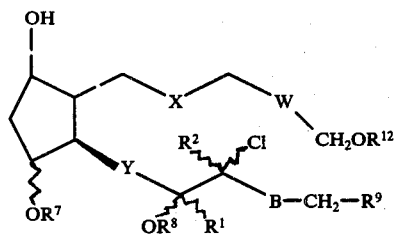

XV (wherein $R^{12}$ represents the trimethylsilyl group or the trityl group and the other symbols are as hereinbefore defined) by reaction (1) with a suitable trimethylsilylating reagent, e.g. trimethylsilyl chloride, N-trimethylsilyldiethylamine or N,O-bis(trimethylsilyl)acetamide, in an inert organic solvent, e.g. methylene chloride or acetone, at a temperature ranging from ambient to $0°$ C., or (2) with trityl chloride in pyridine or methylene chloride in the presence of a base, e.g. pyridine or a tertiary amine, at a temperature ranging from ambient to $70°$ C.

Compounds of general formula XV may be converted to compounds of the general formula:

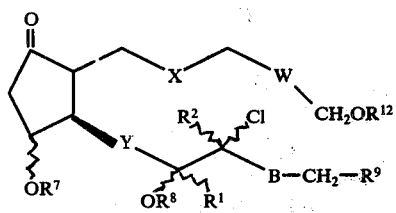

XVI (wherein the various symbols are as hereinbefore defined) by oxidation with Collins' reagent or a dimethyl sulphide-N-chlorosuccinimide complex.

Compounds of general formula XIV or XVI may be converted to compounds of general formula VII, wherein A represents a grouping of formula VIIIA or VIIB, R represents a hydroxymethyl group, $R^3$ represents a hydrogen atom or a hydroxy group and the other symbols are as hereinbefore defined, i.e. compounds of the general formula:

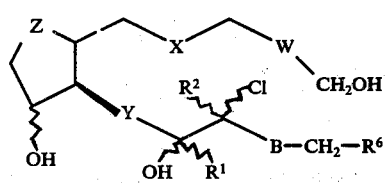

VIIC (wherein the various symbols are as hereinbefore defined) by means heretofore mentioned for the conversion of compounds of general formula IX to those of general formula VIIA.

The method hereinbefore described for the preparation of prostaglandin analogues of general formula VII may be represented by the series of reactions depicted schematically in Scheme A, wherein the various symbols are as hereinbefore defined.

SCHEME A

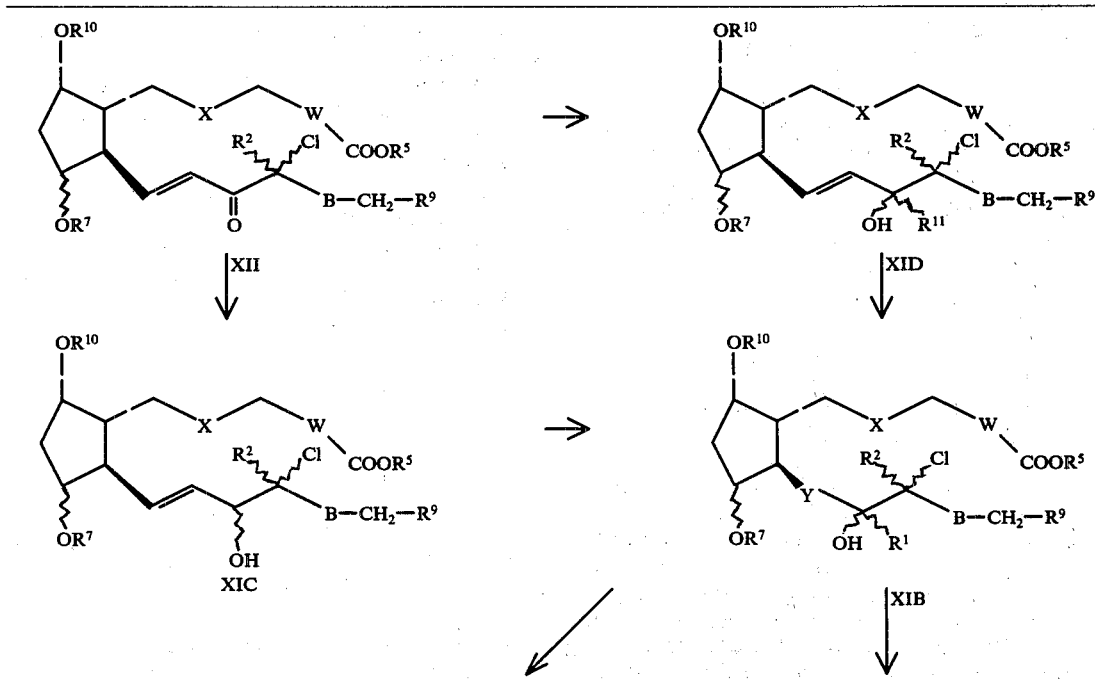

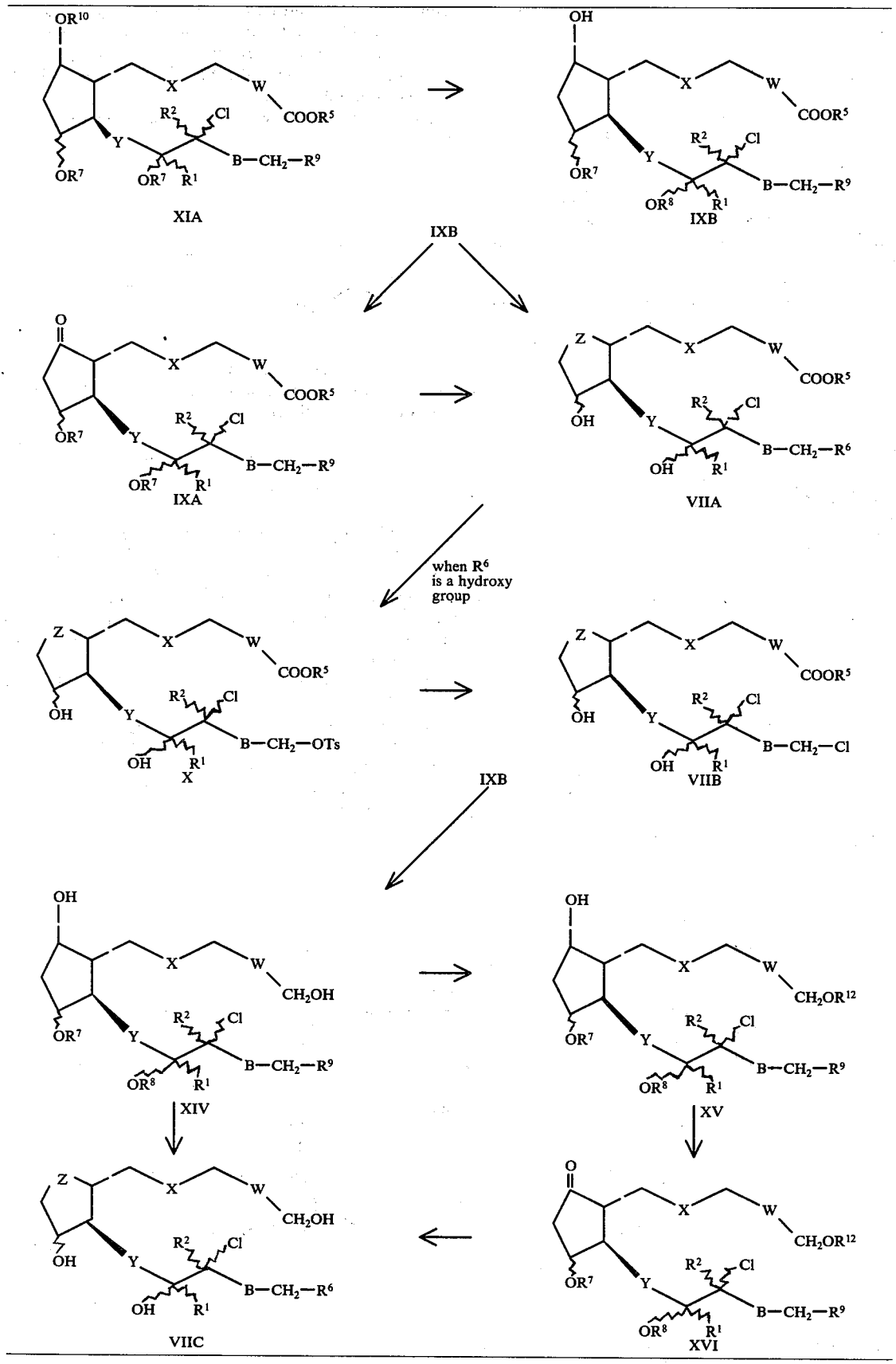
Compounds of general formula XII, wherein $R^2$ represents a hydrogen atom and the other symbols are as

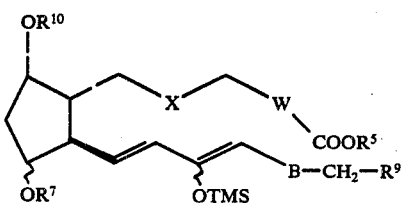

XVII (wherein TMS represents the trimethylsilyl group and the other symbols are as hereinbefore defined) by reaction with N-chlorosuccinimide in an inert organic solvent, e.g. tetrahydrofuran or carbon tetrachloride, at a low temperature, preferably at −20° to −80° C.

Compounds of general formula XVII, wherein the various symbols are as hereinbefore defined, may be prepared from a compound of the general formula:

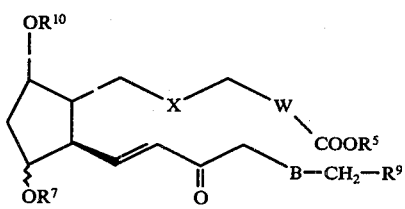

XVIII (wherein the various symbols are as hereinbefore defined) by reaction with a compound of the general formula:

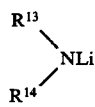

XIX (wherein $R^{13}$ and $R^{14}$ each represent an alkyl group containing from 1 to 6 carbon atoms or a cycloalkyl group containing from 3 to 6 carbon atoms) in an inert organic solvent, e.g. tetrahydrofuran, diethyl ether or 1,2-dimethoxyethane, at a low temperature, preferably at 0° to −80° C., and treatment of the resulting compound with a suitable trimethylsilylating reagent, e.g. trimethylchlorosilane-triethylamine complex, in an inert organic solvent, e.g. tetrahydrofuran or N,N-dimethylformamide, at a low temperature, preferably at 0° to −80° C. [Cf. H.O. House et al, J. Org. Chem., 34, 2324 (1969)].

Compounds of general formula XVIII, wherein the various symbols are as hereinbefore defined, may be prepared by the Wittig reaction of a compound of the general formula:

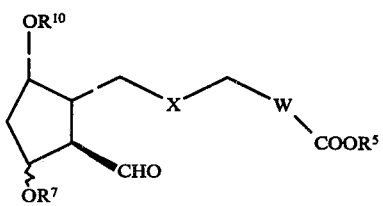

XX (wherein the various symbols are as hereinbefore defined) with the sodium derivative of a diakyl phosphonate of the general formula:

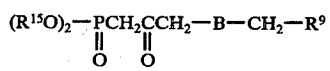

XXI wherein $R^{15}$ represents an alkyl group containing from 1 to 4 carbon atoms and the other symbols are as hereinbefore defined. The reaction is preferably effected by suspending sodium hydride in an inert organic solvent, e.g. tetrahydrofuran or 1,2-dimethoxyethane, and adding the dialkyl phosphonate of formula XXI. The resulting sodium derivative of the dialkyl phosphonate may be reacted with compounds of general formula XX at 20° to 45° C. to form the trans-enone compound of general formula XVIII stereoselectively.

The method hereinbefore described for the preparation of compounds of general formula XIIA may be represented by the series of reactions depicted schematically in Scheme B, wherein the various symbols are as hereinbefore defined.

SCHEME B

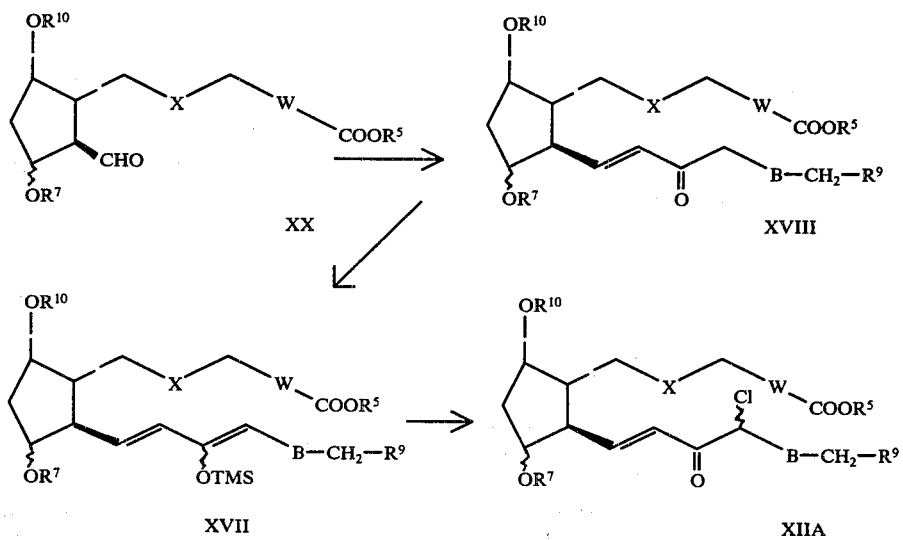

Compounds of general formula XX, used as a starting material in the hereinbefore described procedure, may themselves be prepared by methods known per se from compounds of general formula XXII depicted hereafter by the series of reactions depicted schematically in Scheme C, wherein Q represents the group —SeC$_6$H$_5$ or —SR$^{16}$, wherein R$^{16}$ represents an alkyl group containing from 1 to 4 carbon atoms or a phenyl group, and the other symbols are as hereinbefore defined.

C$_6$H$_5$SeBr) or diphenyldiselenide (i.e. C$_6$H$_5$SeSeC$_6$H$_5$) or a dialkyldisulphide or a diphenyldisulphide of the formula R$^{16}$SSR$^{16}$, wherein R$^{16}$ is as hereinbefore defined, in an inert organic solvent, e.g. tetrahydrofuran, hexamethylphosphotriamide, diethyl ether, n-hexane or n-pentane or a mixture of two or more of them, at a low

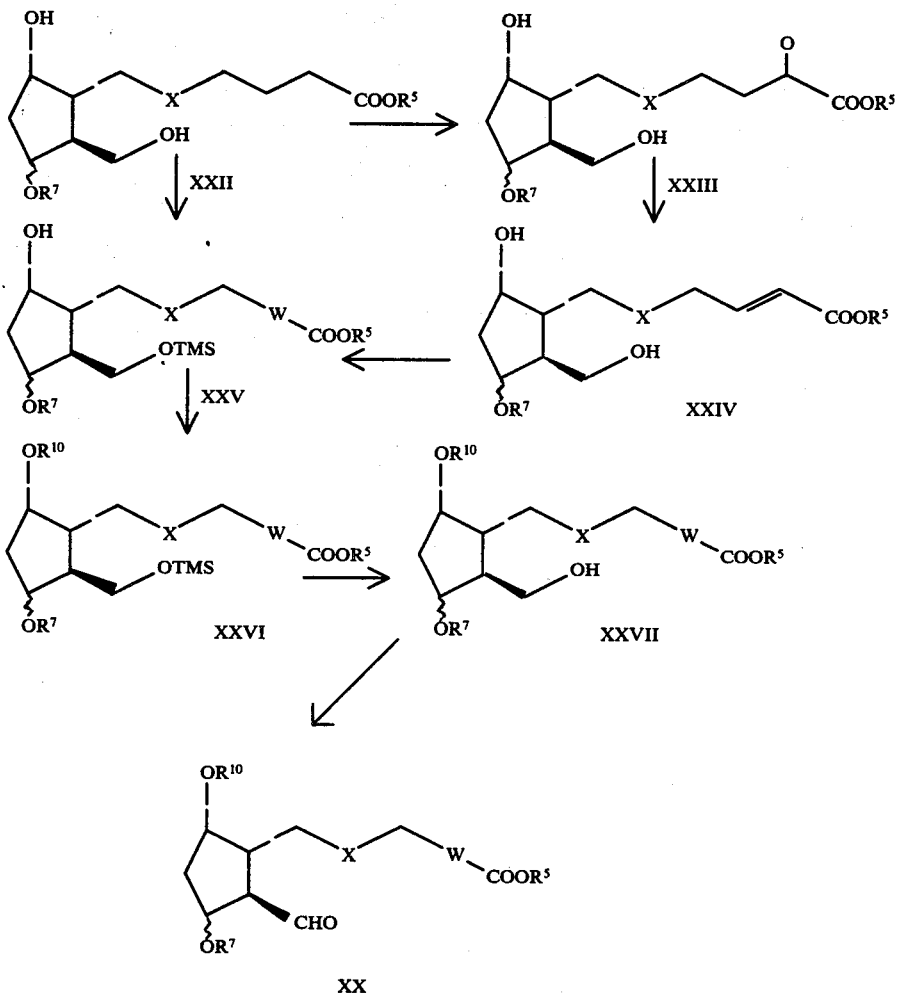

SCHEME C

Compounds of general formula XXII may be converted to compounds of the general formula:

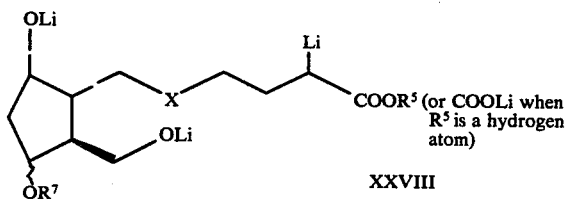

(wherein the various symbols are as hereinbefore defined) by reaction with compounds of general formula XIX, (1) when R$^5$ represents an alkyl group, in tetrahydrofuran at a low temperature, e.g. at −78° C., or (2) when R$^5$ represents a hydrogen atom, in tetrahydrofuran in the presence of hexamethylphosphotriamide at 0° C.

Compounds of general formula XXIII may be prepared from compounds of general formula XXVIII by reaction with benzeneselenenyl bromide (i.e.

temperature, when R$^5$ is an alkyl group, e.g. at −78° C., or, when R$^5$ is a hydrogen atom, at 0° C., followed by hydrolysis of the resulting organolithium compound, for example by treatment with an aqueous solution of ammonium chloride to give compounds of general formula XXIII.

Compounds of general formula XXIII, wherein Q represents the group —SeC$_6$H$_5$, may be converted to compounds of general formula XXIV by reaction (1) with hydrogen peroxide in a mixture of ethyl acetate and tetrahydrofuran or methanol, preferably in the presence of sodium bicarbonate at a temperatur below 30° C., or (2) with sodium periodate in a mixture of water and a lower alkanol, e.g. methanol or ethanol, preferably in the presence of sodium bicarbonate at a temperature below 30° C.

Compounds of general formula XXIII, wherein Q represents the group —SR$^{16}$ (R$^{16}$ being as hereinbefore defined), may be converted to compounds of the general formula:

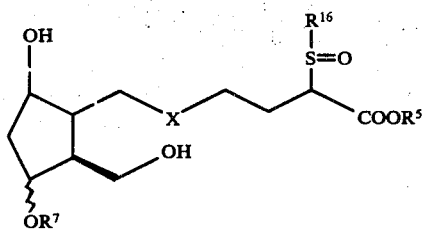

(wherein the various symbols are as hereinbefore defined) by means heretofore mentioned for the conversion of compounds of general formula XXIII, wherein Q represents the group $-SeC_6H_5$, to those of general formula XXIV.

Compounds of general formula XXIX may be converted to compounds of general formula XXIV by treatment (1) when $R^{16}$ represents an alkyl group, in toluene, preferably in the presence of a small amount of calcium carbonate, at a temperature of 100° to 120° C., or (2) when $R^{16}$ represents a phenyl group, in carbon tetrachloride, preferably in the presence of small amount of calcium carbonate, at a temperature of about 50° C.

Compounds of general formula XXII or XXIV may be converted to compounds of general formula XXV by reaction with trimethylchlorosilane in an inert organic solvent, e.g. methylene chloride, in the presence of a base, e.g. pyridine or a tertiary amine, at a low temperature, e.g. at −30° to 0° C.

Compounds of general formula XXV may be converted to compounds of general formula XXVI by reaction with an acyl chloride or an acid anhydride in an inert organic solvent, e.g. methylene chloride, in the presence of a base, e.g. pyridine or a tertiary amine, at a low temperature, e.g. at 0° to 30° C.

Compounds of general formula XXVI may be converted to compounds of general formula XXVII by methods known per se for the removal of the trimethylsilyl group, for example by treatment with an acid; it is preferable not to use a strong acid in order to avoid the risk of the removal of the group $R^7$.

Compounds of general formula XXVII may be converted to compounds of general formula XX under mild and neutral conditions, for example with chromium trioxide-pyridine complex of Jones' reagent in an inert organic solvent, e.g. methylene chloride, at a moderately low temperature, preferably at 0° C.

Compounds of general formula XXII may be prepared by the method described in Japanese Pat. Publication Nos. 49-102646 and 49-134656 from compounds of formula XXX depicted hereafter, which may be represented by the series of reactions depicted schematically below in Scheme D, wherein Ac represents the acetyl group (i.e. $-COCH_3$), $R^{5'}$ represents a straight- or branched-chain alkyl group containing 1 to 4 carbon atoms and the other symbols are as hereinbefore defined.

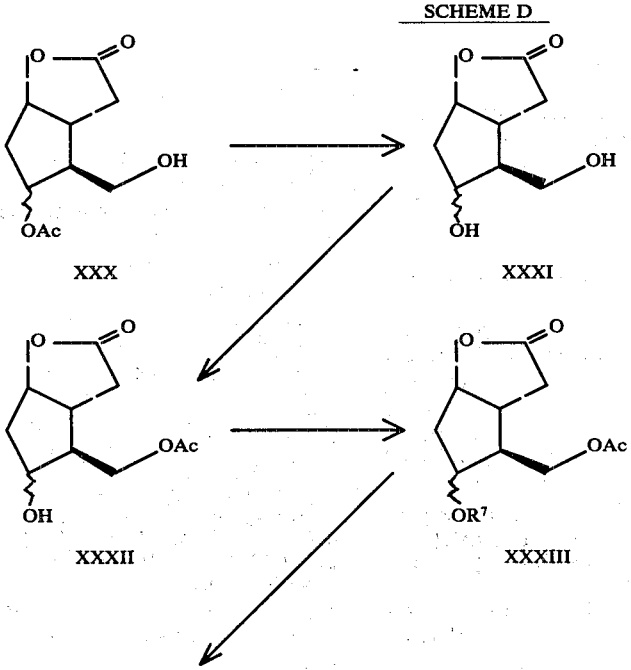

SCHEME D

SCHEME D -continued

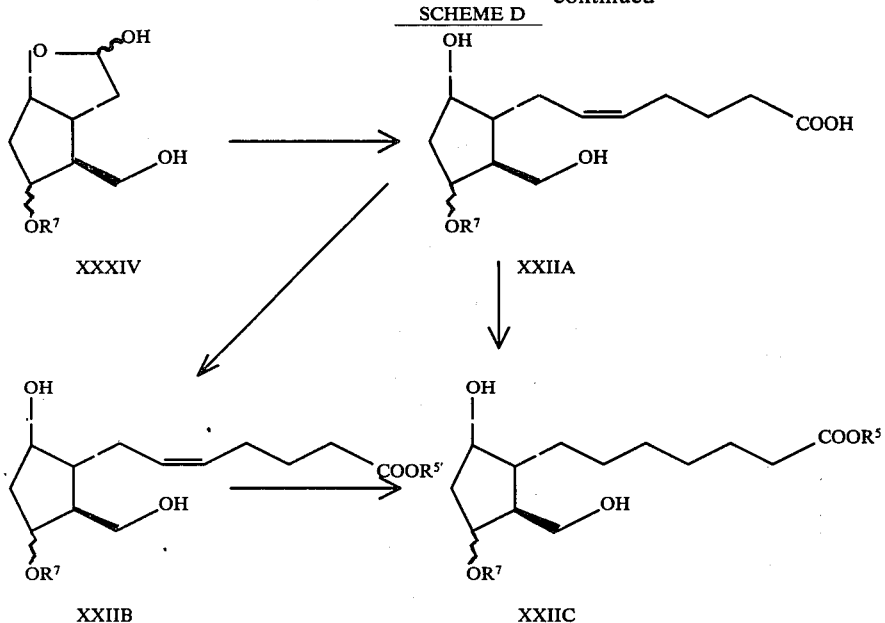

Compounds of formula XXI may be prepared by hydrolysis under alkaline conditions of compounds of formula XXX. Compounds of formula XXXII may be obtained by the acetylation of compounds of formula XXXI under mild conditions and may be converted to compounds of general formula XXXIII by reaction with a dihydropyran, dihydrofuran or ethyl vinyl ether in an inert organic solvent, e.g. methylene chloride, in the presence of a condensing agent, e.g. p-toluenesulphonic acid. Compounds of general formula XXXIV may be prepared by reducing compounds of general formula XXXIII with diisobutylaluminium hydride in an inert organic solvent, e.g. toluene, n-hexane or n-pentane, at −60° C.

Compounds of general formula XXIIA may be prepared from compounds of general formula XXXIV by reaction with (4-carboxybutylidene)triphenylphosphorane of the formula $(C_6H_5)_3P=CH(CH_2)_3COOH$. The reaction between the compounds of general formula XXXIV with (4-carboxybutylidene)triphenylphosphorane [obtained by the reaction of sodium methylsulphinylmethylide with (4-carboxybutyl)triphenylphosphonium bromide] is carried out under the normal conditions utilized for the Wittig reacton, for example in an inert organic solvent, at ambient temperature. The reaction is preferably carried out in dimethyl sulphoxide because the phosphorane compound is practically insoluble in other solvents, e.g. tetrahydrofuran, and because a cis-double bond must be formed stereospecifically in the Wittig reaction. The reaction is generally effected at a temperature of 10° to 40° C., preferably at 20° to 30° C. The acid product of general formula XXIIA may be extracted from the reaction mixture by conventional procedures and further purified by column chromatography on silica gel.

Compounds of general formula XXIIA may, if desired, be reacted with a diazoalkane containing from 1 to 4 carbon atoms, e.g. diazomethane, in an inert organic solvent, e.g. diethyl ether, to give compounds of general formula XXIIB.

Compounds of general formulae XXIIA and XXIIB may, if desired, be reduced to give compounds of general formula XXIIC. Suitably, the reduction may be effected by hyrogenation in the presence of a hydrogenation catalyst, e.g. palladium on charcoal, palladium black or platinum dioxide, in the presence of an inert organic solvent, for example a lower alkanol, e.g. methanol or ethanol, at laboratory temperature at normal or elevated pressure, e.g. at a hydrogen pressure from atmospheric to 15 kg./cm².

The starting compounds of formula XXX wherein the group OAc is in α-configuration, i.e. the compound of the formula:

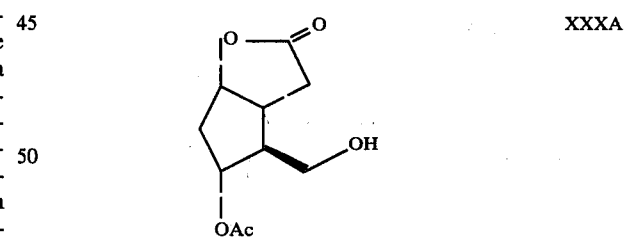

XXXA wherein Ac is as hereinbefore defined, may be prepared as described in J. Amer. Chem. Soc., 91. 5675, (1969) and ibid, 92, 397 (1970) by E. J. Corey et al.

A method for the preparation of the starting materials of formula XXX, wherein the group OAc is in β-configuration, hereinafter depicted in formula XXXB, utilizing known procedures may be represented by the series of reactions depicted schematically below in Scheme E [cf. E. J. Corey and Shiro Terashima, Tetrahedron Letters No. 2,111-113 (1972)], wherein Ts represents the tosyl group and Ac is as hereinbefore defined.

SCHEME E

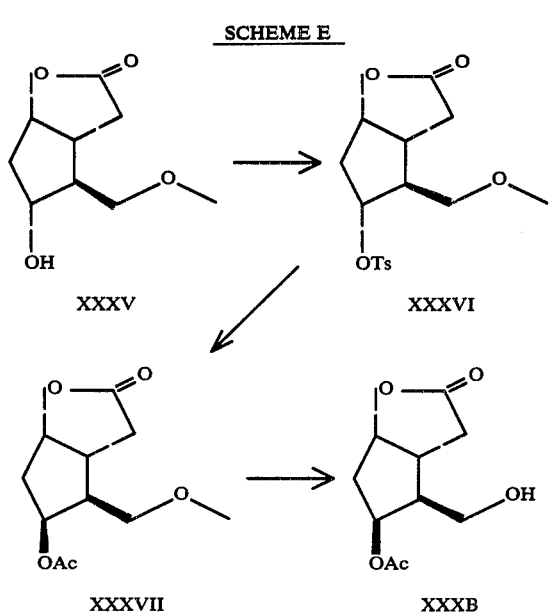

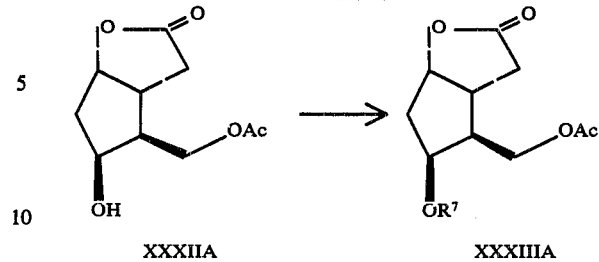

The various reactions depicted above in Scheme E may be effected by methods known per se. Compounds of formula XXXVII may be prepared by reacting compounds of formula XXXVI with tetraethylammonium acetate.

A method for the preparation of the compounds of general formula XXXIII, wherein the group OR⁷ is in β-configuration [hereafter depicted in formula XXXIIIA], may be represented by the series of reactions depicted schematically below in Scheme F, wherein Mes represents the methylsulphonyl group (i.e. —SO₂CH₃) and the other symbols are as hereinbefore defined.

SCHEME F

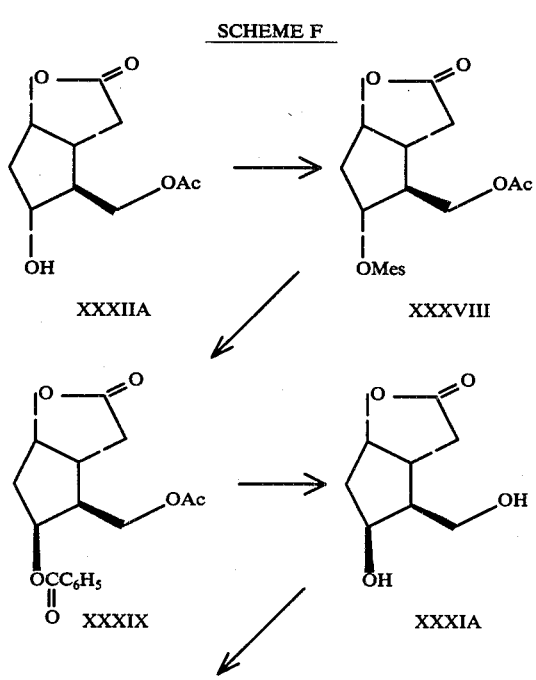

Compounds of general formula XXXVIII may be prepared from compounds of formula XXXIIA by reaction with methanesulphonyl chloride in an inert organic solvent, e.g. methylene chloride, in the presence of triethylamine at a temperature below −20° C.

Compounds of formula XXXIX may be prepared from compounds of formula XXXVIII by reaction with sodium benzoate in N,N-dimethylformamide or dimethyl sulphoxide or a mixture thereof at a temperature ranging from ambient to 90° C.

Compounds of formula XXXIA may be prepared from compounds of formula XXXIX by hydrolysis under alkaline conditions, for example with potassium carbonate in methanol at a temperature below 60° C.

The conversion of compounds of formula XXXIA to those of general formula XXXIIIA may be carried out by means heretofore mentioned for the conversion of compounds of formula XXXI to those of general formula XXXIII.

Compounds of general formula XII may also be prepared from compounds of general formula XX by reaction with the sodium derivative of a compound of the general formula:

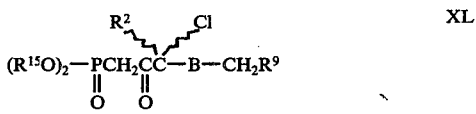

XL wherein the various symbols are as hereinbefore defined. The reaction may be carried out by means heretofore mentioned for the conversion of compounds of general formula XX to those of general formula XVIII.

The dialkyl phosphonates of general formula XXI may be prepared by reacting a solution of n-butyllithium in an inert organic solvent, e.g. diethyl ether, n-hexane or n-pentane, with a solution of dialkyl methylphosphonate of the general formula:

XLI (wherein $R^{15}$ is as hereinbefore defined), e.g. dimethyl methylphosphonate or diethyl methylphosphonate, at a temperature below −50° C. and then adding dropwise to the reaction mixture a solution of a compound of the general formula:

$$R^{17}OOCCH_2\text{—}B\text{—}CH_2R^9 \qquad XLII$$

(wherein $R^{17}$ represents an alkyl group containing from 1 to 4 carbon atoms and the other symbols are as hereinbefore defined) in tetrahydrofuran at a temperature below −50° C., and then stirring at a moderately low temperature, e.g. at 0° C., to give the desired dialkyl phosphonate of general formula XXI.

The dialkyl phosphonates of general formula XL may be prepared by reacting a solution of a compound of general formula:

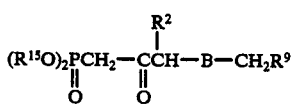

XLIII (wherein the various symbols are as hereinbefore defined) in tetrahydrofuran with a suspension of sodium hydride in tetrahydrofuran at room temperature, and adding to the reaction mixture a solution of n-butyllithium in an inert organic solvent, e.g. n-hexane, at a temperature below 0° C., and adding to the resulting reaction mixture a solution of benzenesulphonyl chloride in tetrahydrofuran at −78° C., then stirring at a temperature ranging from ambient to 0° C. to give the desired dialkyl phosphonate of general formula XL.

Compounds of general formula XLIII may be prepared from a compound of the general formula:

XLIV (wherein the various symbols are as hereinbefore defined) by means heretofore mentioned for the conversion of compounds of general formula XLII to those of general formula XXI.

Compounds of general formula XLII or XLIV may be prepared by methods known per se According to another feature of the present invention, the prostaglandin analogues of general formula VII, wherein A represents a grouping of formula VIIIB and the other symbols are as hereinbefore defined [hereinafter depicted in formula VIID], are prepared by the process which comprises hydrolyzing the trimethylsilyloxy groups of a compound of the general formula:

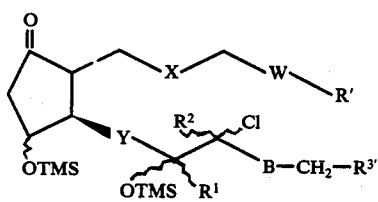

XLV (wherein R' represents the group —COOR$^4$, in which R$^4$ is as hereinbefore defined, or a trimethylsilyloxymethyl group (i.e. —CH$_2$OTMS), R$^{3'}$ represents a hydrogen or chlorine atom or a trimethylsilyloxy group and the other symbols are as hereinbefore defined) to hydroxy groups under extremely mild acidic conditions, for example by treatment of a solution of such a compound in an inert organic solvent, e.g. ethyl acetate or diethyl ether, with an aqueous solution of oxalic acid, preferably at room temperature.

Compounds of general formula XLV may be prepared by oxidation of a compound of the general formula:

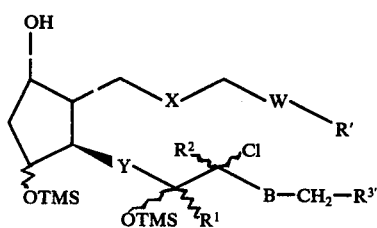

XLVI (wherein the various symbols are as hereinbefore defined) with Collins' reagent in the presence of an inert organic solvent, e.g. methylene chloride, preferably at a temperature of about 10° C., or with dimethyl sulphide-N-chlorosuccinimide complex at 0° to −30° C. [cf. E. J. Corey and C. U. Kim, J. Amer. Chem. Soc., 94, 7586 (1972)].

Compounds of general formula XLVI may be prepared from a compound of the general formula:

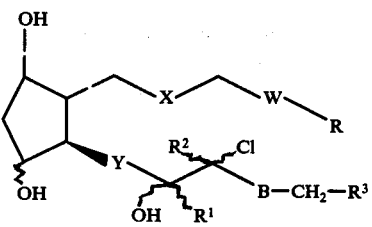

VIIE (wherein the various symbols are as hereinbefore defined) by reaction with a suitable trimethylsilylating reagent, e.g. N-trimethylsilyldiethylamine or N,O-bis(-trimethylsilyl)acetamide, in an inert organic solvent, e.g. acetone or methylene chloride, preferably at room temperature.

The hereinbefore described sequence of reactions is illustrated schematically in following Scheme G, wherein the various symbols are as hereinbefore defined.

SCHEME G

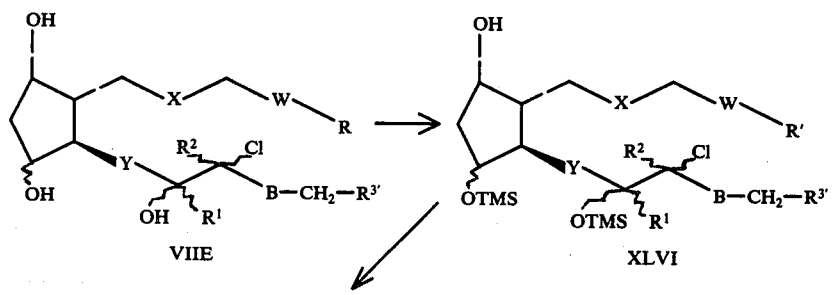

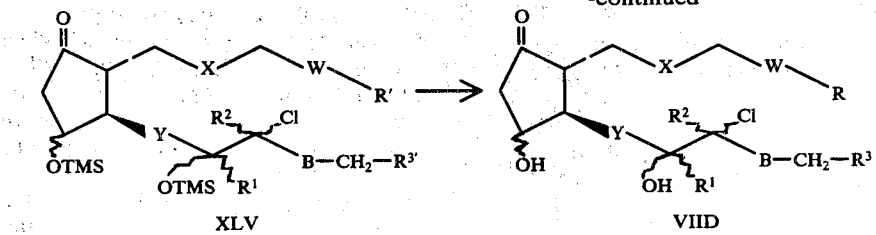

XLV → VIID

According to still another feature of the present invention, the prostaglandin analogues of general formula VIIA, wherein Z represents

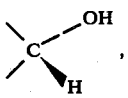

Y represents a transvinylene group, R² represents a hydrogen atom and the other symbols are as hereinbefore defined, i.e. compounds of the general formula:

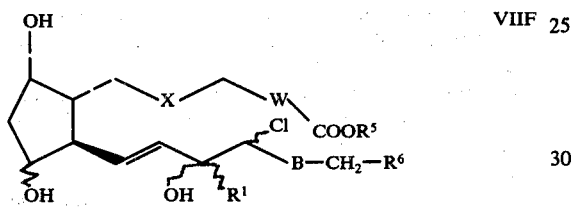

VIIF (wherein the various symbols are as hereinbefore defined), are prepared by the process which comprises hydrolyzing to hydroxy groups, the groups OR⁷ of a compound of the general formula:

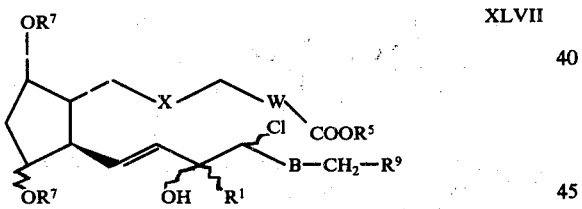

XLVII (wherein the various symbols are as hereinbefore defined) by means heretofore mentioned for the conversion of compounds of general formula IX to those of general formula VIIA.

Compounds of general formula XLVII, wherein the various symbols are as hereinbefore defined, may be prepared from a compound of the general formula:

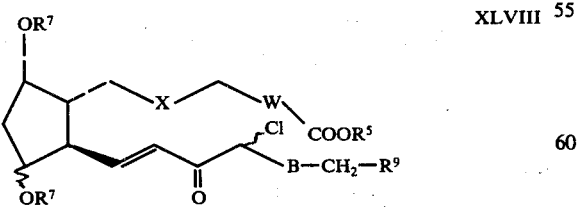

XLVIII (wherein the various symbols are as hereinbefore defined) by means heretofore mentioned for the conversion of compounds of general formula XII to those of general formula XI. The product thus obtained is a mixture of isomers in which the hydroxy group at position 15 is in α- or β-configuration respectively. If desired, the isomer having the hydroxy group in α-configuration may be separated from the isomer having the hydroxy group in β-configuration by column chromatography of the mixture on silica gel.

Compounds of general formula XLVIII, wherein the various symbols are as hereinbefore defined, may be prepared from a compound of the general formula:

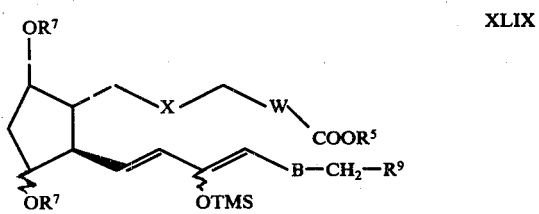

XLIX (wherein the various symbols are as hereinbefore defined) by means heretofore mentioned for the conversion of compounds of general formula XVII to those of general formula XIIA.

Compounds of general formula XLIX, wherein the various symbols are as hereinbefore defined, may be prepared from a compound of the general formula:

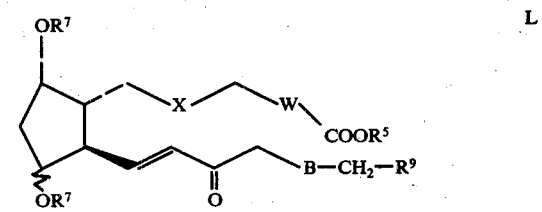

L (wherein the various symbols are as hereinbefore defined) by means heretofore mentioned for the conversion of compounds of general formula XVIII to those of general formula XVII.

Compounds of general formula L, wherein the various symbols are as hereinbefore defined, may be prepared from a compound of the general formula:

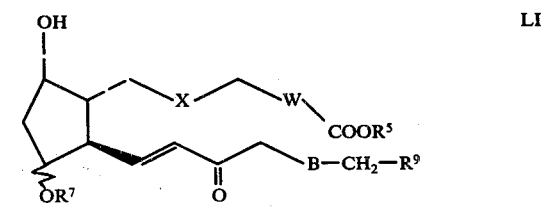

LI (wherein the various symbols are as hereinbefore defined) by reaction with a dihydropyran, dihydrofuran or ethyl vinyl ether in an inert organic solvent, e.g. methylene chloride, in the presence of a condensing agent, e.g. p-toluenesulphonic acid.

Compounds of general formula LI, wherein the various symbols are as hereinbefore defined, may be prepared from a compound of the general formula:

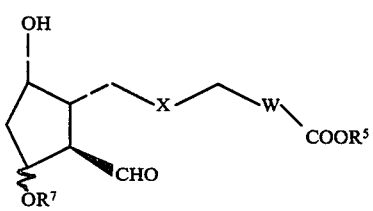

LII (wherein the various symbols are as hereinbefore defined) by means heretofore mentioned for the conversion of compounds of general formula XX to those of general formula XVIII.

Compounds of general formula LII, wherein the various symbols are as hereinbefore defined, may be prepared from compounds of general formula XXII or XXIV by reaction with a chromium trioxide-pyridine complex in an inert organic solvent, e.g. methylene chloride, at a low temperature, preferably at 0° C.

If desired, compounds of general formula L, wherein the grouping —B—$CH_2$—$R^9$ represents the n-butyl group and the other symbols are as hereinbefore defined, may be prepared from a compound of the general formula:

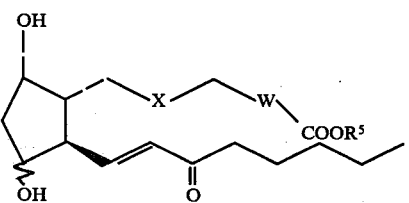

LIII (wherein the various symbols are as hereinbefore defined) by means heretofore mentioned for the conversion of compounds of general formula LI to those of general formula L.

Compounds of general formula LIII wherein the various symbols are as hereinbefore defined, may be prepared from a compound of the general formula:

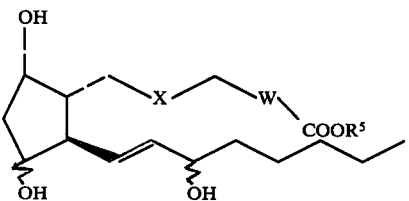

LIV (wherein the various symbols are as hereinbefore defined) by oxidation with active manganese dioxide in an inert organic solvent, e.g. methylene chloride, preferably at room temperature.

Compounds of general formula LIV, wherein W represents a trans-vinylene group and the other symbols are as hereinbefore defined, are described in Belgium Pat. No. 823778.

The method hereinbefore described for the preparation of compounds of general formula VIIF may be represented by the series of reactions depicted schematically below in Scheme H, wherein the various symbols are as hereinbefore defined.

SCHEME H

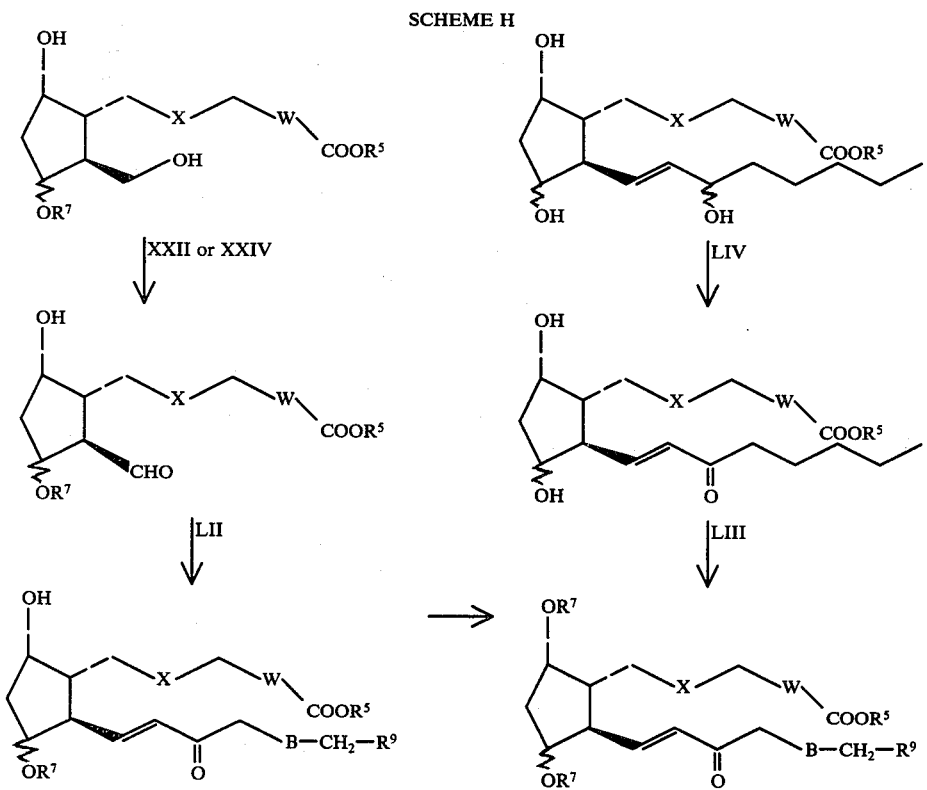

SCHEME H -continued

LI

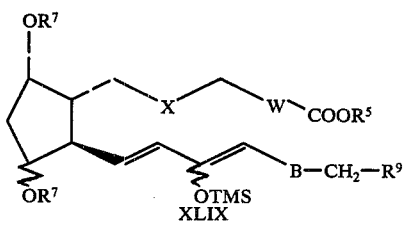
XLIX

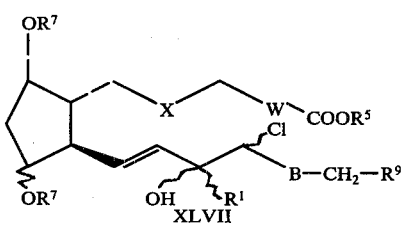
XLVII

L

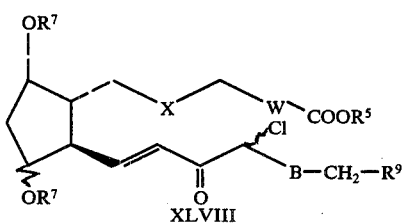
XLVIII

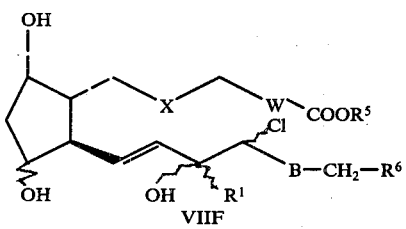
VIIF

According to a still further feature of the present invention, the compounds of general formula VII, wherein A, B, W, X, Y, $R^1$, $R^2$ and $R^3$ are as hereinbefore defined and R represents a grouping —$COOR^{4'}$ in which $R^{4'}$ represents a straight- or branched-chain alkyl group containing from 1 to 12 carbon atoms, are prepared by esterification of the corresponding acids of formula VII wherein R represents a carboxy group (i.e. —COOH) by methods known per se, for example by reaction with (i) the appropriate diazoalkane in an inert organic solvent, e.g. diethyl ether, at a temperature of from −10° C. to 25° C. and preferably 0° C., (ii) the appropriate alcohol in the presence of dicyclohexylcarbodiimide as condensing agent, or (iii) the appropriate alcohol following formation of a mixed anhydride by adding a tertiary amine and pivaloyl halide or an alkylsulphonyl or arylsulphonyl halide (cf. our British Pat. Nos. 1362956 and 1364125).

Compounds of general formula VII wherein R represents a carboxy group may, if desired, be converted by methods known per se into non-toxic salts.

By the term "non-toxic salts," as used in this specification, is meant salts the cations of which are relatively innocuous to the animal organism when used in therapeutic doses so that the beneficial pharmacological properties of the acids within general formula VII are not vitiated by side-effects ascribable to those cations. Preferably the salts are water-soluble. Suitable salts include the alkali metal, e.g. sodium and potassium, and ammonium salts and pharmaceutically-acceptable (i.e. non-toxic) amine salts. Amines suitable for forming such salts with carboxylic acids are well known and include, for example, amines derived in theory by the replacement of one or more of the hydrogen atoms of ammonia by groups, which may be the same or different when more than one hydrogen atom is replaced, selected from, for example, alkyl groups containing from 1 to 6 carbon atoms and hydroxyalkyl groups containing from 1 to 3 carbon atoms.

The non-toxic salts may be prepared from acids of general formula VII wherein R represents a carboxy group by, for example, reaction of stoichiometric quantities of an acid of general formula VII and the appropriate base, e.g. an alkali metal hydroxide or carbonate, ammonium hydroxide, ammonia or an amine, in a suitable solvent. The salts may be isolated by lyophilisation of the solution, or, if sufficiently insoluble in the reaction medium, by filtration, if necessary after removal of part of the solvent.

Cyclodextrin clathrates of the prostaglandin analogues of general formula VII may be prepared by dissolving the cyclodextrin in water or an organic solvent which is miscible with water and adding to the solution the prostaglandin analogue in a water-miscible organic solvent. The mixture is then heated and the desired cyclodextrin clathrate product isolated by concentrating the mixture under reduced pressure or by cooling and separating the product by filtration or decantation. The ratio of organic solvent to water may be varied according to the solubilities of the starting materials and products. Preferably the temperature is not allowed to exceed 70° C. during the preparation of the cyclodextrin clathrates. α-, β- or γ-Cyclodextrins or mixtures thereof may be used in the preparation of the cyclodextrin clathrates. Conversion into their cyclodextrin clathrates serves to increase the stability of the prostaglandin analogues.

The present invention also includes, as further features, the hitherto unknown compounds of general formulae IX, X, XIV, XV, XVI, XVII, XLV and XLVII, and the methods heretofore described for their preparation.

The prostaglandin analogues of general formula VII and their cyclodextrin clathrates and, when R represents a carboxy group, non-toxic salts possess the valuable pharmacological properties typical of the prostaglandins in a selective fashion, in particular hypotensive activity, inhibitory activity on blood platelet aggregation, inhibitory activity on gastric acid secretion and gastric ulceration, stimulatory activity on uterine contraction and abortifacient, luteolytic and antinidatory activity, and are useful in the treatment of hypertension, in the treatment of disorders of the peripheral circulation, in the prevention and treatment of cerebral thrombosis and myocardial infarction, in the treatment of gastric ulceration, in the termination of pregnancy and induction of labour in pregnant female mammals and in the treatment of impaired fertility, in the control of oestrus, contraception and menstrual regulation in female mammals. For example, in standard laboratory tests (i) by intravenous administration to the allobarbital-anaesthetized dog, 16ξ-chloro-PGE$_2$ methyl ester products falls in blood pressure of 20 mm.Hg and 30 mm.Hg lasting 8 and 16 minutes at the doses of 0.2 and 0.5 μg./kg. animal body weight, respectively, 16ξ-chloro-PGE$_1$ methyl ester produces falls in blood pressure of 20 mm.Hg and 36 mm.Hg lasting 28 and 59 minutes at the doses of 0.2 and 0.5 μg./kg. animal body weight, respectively, 16ξ-chloro-13,14-dihydro-PGE$_1$ methyl ester produces falls in blood pressure of 26 mm.Hg, 30 mm.Hg and 44 mm.Hg lasting 20, 22 and 23 minutes at the doses of 0.2, 0.5 and 1.0 μg./kg. animal body weight, respectively, 16ξ-chloro-15-epi-PGE$_2$ methyl ester produces falls in blood pressure of 24 mm.Hg and 60 mm.Hg lasting 14 and 44 minutes at the doses of 5 and ·10 μg./kg. animal body weight, respectively, 16ξ-chloro-11-epi-PGE$_1$ methyl ester produces falls in blood pressure of 24 mm.Hg and 50 mm.Hg lasting 16 and 30 minutes at the doses of 10 and 20 μg./kg. animal body weight, respectively, 16ξ-chloro-PGE$_2$ alcohol produces falls in blood pressure of 20 mm.Hg and 26 mm.Hg lasting 50 and 52 minutes at the doses of 2 and 5 μg./kg. animal body weight, respectively, 15ξ-methyl-16ξ-chloro-PGE$_1$ methyl ester produces falls in blood pressure of 12 mm.Hg, 26 mm.Hg and 38 mm.Hg lasting 16, 34 and 37 minutes at the doses of 2, 5 and 10 μg./kg. animal body weight, respectively, 16ξ-chloro-16-methyl-PGE$_1$ methyl ester produces falls in blood pressure of 16 mm.Hg and 24 mm.Hg lasting 24 and 43 minutes at the doses of 1 and 2 μg./kg. animal body weight, respectively, and 16ξ-chloro-trans-Δ$^2$-PGE$_1$ methyl ester produces falls in blood pressure of 18 mm.Hg and 38 mm.Hg lasting 16 and 26 minutes at the doses of 0.2 and 0.5 μg./kg. animal body weight, respectively; (ii) by oral administration to the conscious spontaneously hypertensive rat, 16ξ-chloro-PGE$_2$ methyl ester produces falls in blood pressure of 54 mm.Hg, 37 mm.Hg and 29 mm.Hg at 0.5, 1.0 and 3.0 hours after administration, respectively, at the dose of 0.1 mg./kg. animal body weight, 16ξ-chloro-PGE$_1$ methyl ester produces falls in blood pressure of 38 mm.Hg, 16 mm.Hg and 12 mm.Hg at 0.5, 1.0 and 3.0 hours after administration, respectively, at the dose of 0.1 mg./kg. animal body weight, 16ξ-chloro-13,14-dihydro-PGE$_1$ methyl ester produces falls in blood pressure of 39 mm.Hg, 32 mm.Hg and 26 mm.Hg at 0.5, 1.0 and 3.0 hours after administration, respectively, at the dose of 1.0 mg./kg. animal body weight, 16ξ-chloro-16-methyl-PGE$_1$ methyl ester produces falls in blood pressure of 33 mm.Hg, 20 mm.Hg and 28 mm.Hg at 0.5, 1.0 and 3.0 hours after administration, respectively, at the dose of 0.1 mg./kg. animal body weight and 16ξ-chloro-trans-Δ$^2$-PGE$_1$ methyl ester produces falls in blood pressure of 37 mm.Hg, 27 mm.Hg and 18 mm.Hg at 0.5, 1.0 and 3.0 hours after administration, respectively, at the dose of 0.1 mg./kg. animal body weight; (iii) 16ξ-chloro-PGE$_1$ methyl ester produces a 50% inhibition of adenosine diphosphate-induced blood platelet aggregation in platelet-rich plasma of rats at the concentration of 5.6 × 10$^{-2}$ μg./ml. in comparison with controls, 16ξ-chloro-13,14-dihydro-PGE$_1$ methyl ester produces a 50% inhibition of adenosine diphosphate-induced blood platelet aggregation in platelet-rich plasma of rats at the concentration of 7.4 × 10$^{-2}$ μg./ml. in comparison with controls and 16ξ-chloro-trans-Δ$^2$-PGE$_1$ methyl ester produces a 50% inhibition of adenosine diphosphate-induced blood platelet aggregation in platelet-rich plasma of rats at the concentration of 2.2 × 10$^{-2}$ μg./ml. in comparison with controls; (iv) in stress ulceration of rats [produced according to the method of Takagi and Okabe – Jap. J. Pharmac., 18, 9–18 (1968) by soaking rats in a water bath at 19° C. for 6 hours], 16ξ-chloro-PGE$_2$ methyl ester produces 64.8% and 80.7% inhibitions of stress ulceration of oral administration at the doses of 10 and 20 μg./kg. animal body weight, respectively, 16ξ-chloro-PGE$_1$ methyl ester produces 84.9% inhibition of stress ulceration by oral administration at the dose of 50 μg./kg. animal body weight, 16ξ-chloro-13,14-dihydro-PGE$_1$ methyl ester produces 36.9% inhibition of stress ulceration by oral administration at the dose of 100 μg./kg. animal body weight, 16ξ-chloro-PGE$_2$ alcohol produces 70.1% inhibition of stress ulceration by oral administration at the dose of 50 μg./kg. animal body weight, 15ξ-methyl-16ξ-chloro-PGE$_1$ methyl ester produces 44.0% and 62.1% inhibitions of stress ulceration by oral administration at the doses of 100 and 200 μg./kg. animal body weight, respectively, 16ξ-chloro-16-methyl-PGE$_1$ methyl ester produces 81.3% inhibition of stress ulceration by oral administration at the dose of 200 μg./kg. animal body weight, 16ξ-chlorotrans-Δ$^2$-PGE$_1$ methyl ester produces 62.3% inhibition of stress ulceration of oral administration at the dose of 200 μg./kg. animal body weight, 16ξ-chloro-20-hydroxy-PGE$_1$ methyl ester produces 52.5% and 53.3% inhibitions of stress ulceration by oral administration at the doses of 100 and 200 μg./kg. animal body weight, respectively, and 16ξ,20-dichloro-PGE$_1$ methyl ester produces 55.4% and 87.9% inhibitions of stress ulceration by oral administration at the doses of 100 and 200 μg./kg. animal body weight, respectively; (v) 16ξ-chloro-PGE$_2$ methyl ester, 15ξ-methyl-16ξ-chloro-PGE$_1$ methyl ester and 16ξ-chloro-16-methyl-PGE$_1$ methyl ester produce an increase in gastric acid pH from 2.0–2.5 to at least 4.0 in 50% of pentagastrin-treated rats when perfused into the stomach at the rates of 0.11, ≧1 and <1 μg./animal/minute, respectively; (vi) 16ξ-chloro-PGF$_{2α}$ methyl ester, 16ξ-chloro-PGE$_2$ methyl ester, 16ξ-chloro-PGE$_1$ methyl ester, 16ξ-chloro-13,14-dihydro-PGE$_1$ methyl ester, 16ξ-chloro-15-epi-PGE$_2$ methyl ester, 16ξ-chloro-11-epi-PGE$_1$ methyl ester, 16ξ-chloro-PGE$_2$ alcohol, 15ξ-methyl-16ξ-chloro-PGE$_1$ methyl ester, 16ξ-chloro-16-methyl-PGE$_1$ methyl ester, 16ξ-chloro-trans-Δ$^2$-PGE$_1$ methyl ester, 16ξ-chloro-20-hydroxy-PGE$_1$ methyl ester and 16ξ,20-dichloro-PGE$_1$ methyl ester stimulate uterine contraction in the pregnant female rat when administered intravenously on the 20th day of gestation at the doses of 5–10, 2, 1, 5–10, 10–20, 10–20, 1–2, 1, 0.2–0.5, 5, 1–2 and 1–2μg./kg. animal body weight, respectively, and (vii) 16ξ-chloro-PGF$_{2α}$ methyl ester inhibits implantation in pregnant female rats when administered subcutaneously on the 3rd, 4th and 5th days of pregnancy at the daily dose of 0.20 mg./kg. animal body weight.

The prostaglandin analogues of the present invention, their cyclodextrin clathrates and non-toxic salts can cause diarrhoea, the doses by oral administration of 16ξ-chloro-PGF$_{2α}$ methyl ester, 16ξ-chloro-PGE$_2$ methyl ester, 16ξ-chloro-PGE$_1$ methyl ester, 16ξ-chloro-13,14-dihydro-PGE$_1$ methyl ester, 16ξ-chloro- 15-epi-PGE₂ methyl ester, 16ξ-chloro-11-epi-PGE₁ methyl ester, 16ξ-chloro-PGE₂ alcohol, 15ξ-methyl-16ξ-chloro-PGE₁ methyl ester, 16ξ-chloro-16-methyl-PGE₁ methyl ester, 16ξ-chloro-trans-$\Delta^2$-PGE₁ methyl ester, 16ξ-chloro-20-hydroxy-PGE₁ methyl ester and 16ξ,20-dichloro-PGE₁ methyl ester required to produce diarrhoea in 50% of mice so treated are <0.5, 0.09, 0.20, 0.9, 7.2, 5–10, 0.046, 0.2–0.4, 0.22, 0.09, 2.0 and 0.65 mg./kg. animal body weight, respectively.

The following Reference Examples and Examples illustrate the preparation of new prostaglandin analogues of the present invention. In them 'IR', 'NMR' and 'TLC' represent respectively 'Infrared absorption spectrum' 'Nuclear magnetic resonance spectrum' and 'Thin layer chromatography'. Where solvent ratios are specified in chromatographic separations and otherwise the ratios are by volume.

REFERENCE EXAMPLE 1

15-Oxo-PGE$_{2\alpha}$ methyl ester 100 g. of active manganese dioxide were added to a solution of 15.47 g. of PGF$_{2\alpha}$ methyl ester in 700 ml. of methylene chloride, and the mixture was stirred at room temperature for 2 hours and then filtered. The precipitate was washed thoroughly with ethyl acetate, and the filtrate and washing were combined and concentrated under reduced pressure. The residue was purified by column chromatography on silica gel using a mixture of benzene and ethyl acetate (2:1) as eluent to give 8.8 g. of the title compound having the following physical characteristics:-

TLC (developing solvent, benzene-ethyl acetate = 1:2):

Rf = 0.44;

IR (liquid film):ν; 1740, 1695, 1670, 1624, 1436, 1240, 980 cm⁻¹;

NMR (CDCl₃ solution): δ; 6.89–6.53 (1H, d—d), 6.34–6.08 (1H, d), 5.53–5.32 (2H, m), 4.36–3.93 (2H, m), 3.66 (3H, s).

REFERENCED EXAMPLE 2

Methyl 9α,11α-bis(2-tetrahydropyranoyloxy)-15-oxoprosta-cis-5,trans-13-dienoate A catalytic amount of p-toluenesulphonic acid and 10 ml. of 2,3-dihydropyran were added to a solution of 2.527 g. of 15-oxo-PGF$_{2\alpha}$ methyl ester (prepared as described in Reference Example 1) in 50 ml. of methylene chloride and the reaction mixture was stirred at room temperature for 15 minutes and then diluted with 100 ml. of ethyl acetate. The mixture was washed with an aqueous sodium bicarbonate solution and an aqueous sodium chloride solution, dried over sodium sulphate and concentrated under reduced pressure. The residue was purified by column chromatography on silica gel using a mixture of benzene and ethyl acetate (10:1) as eluent to give 3.136 g. of the title compound having the following physical characteristics:-

TLC (developing solvent, benzene-ethyl acetate = 1:1):

Rf = 0.61;

IR (liquid film):ν; 1740, 1695, 1670, 1624, 1436, 1350, 1138, 1080, 1030, 990, 873 cm⁻¹;

NMR (CDCl₃ solution): δ; 6.9–6.48 (1H, m), 6.18 (1H, d—d), 5.58–5.25 (2H, m), 4.78–4.45 (2H, m), 4.29–3.3 (6H, m), 3.66 (3H, s), 2.54 (2H, t), 2.31 (2H, t).

REFERENCE EXAMPLE 3

Methyl 9α,11α-bis(2-tetrahydropyranyloxy)-15-trimethylsilyloxyprosta-cis-5,trans-13,cis(or trans)-15-trienoate 70 ml. of 0.15M lithium diisopropylamide solution in a mixture of tetrahydrofuran and diethyl ether (4:3) were added dropwise over a period of 3 hours to a solution of 4.272 g. of methyl 9α,11α-bis(2-tetrahydropyranyloxy)-15-oxoprosta-cis-5,trans-13-dienoate (prepared as described in Reference Example 2) in 17 ml. of dry tetrahydrofuran at −78° C. under an atmosphere of nitrogen, and the reaction mixture was stirred at the same temperature for 30 minutes. To the reaction mixture thus obtained, there was added dropwise over a period of 15 minutes of 8.16 g. of trimethylchlorosilane and 2.02 g. of triethylamine in 30 ml. of dry diethyl ether with stirring and the reaction mixture was stirred at room temperature for 20 minutes, and then concentrated under reduced pressure. The residue was purified by column chromatography on silica gel using a mixture of cyclohexane and ethyl acetate (10:1) as eluent to give 1.227 g. of the title compound having the following physical characteristics:-

TLC (developing solvent, benzene-ethyl acetate = 5:1):

Rf = 0.47;

IR (liquid film):ν; 1741, 1660–1610, 1255, 1140, 1025, 845 cm⁻¹;

NMR (CDCl₃ solution): δ; 5.78–5.13 (4H, m), 4.9–4.35 (3H, m), 4.35–3.26 (6H, m), 3.65 (3H, s), 2.3 (3H, t), 0.21–0.05 (9H, m).

REFERENCE EXAMPLE 4

Methyl 9α,11α-bis(2-tetrahydropyranyloxy)-15-oxo-16ξ-chloroprosta-cis-5,trans-13-dienoate 63 mg. of N-chlorosuccinimide were added portionwise to a solution of 248 mg. of methyl 9α,11α-bis(2-tetrahydropyranyloxy)-15-trimethylsilyloxyprostacis-5,trans-13-cis(or trans)-15-trienoate (prepared as described in Reference Example 3) in 3 ml of tetrahydrofuran at −78° C., and the mixture was stirred at the same temperatue for 30 minutes. The reaction mixture was then diluted with 50 ml. of ethyl acetate, washed with 1N hydrochloric acid, an aqueous sodium bicarbonate solution and an aqueous sodium chloride solution, dried over sodium sulphate and concentrated under reduced pressure. The residue was purified by column chromatography on silica gel using a mixture of benzene and ethyl acetate (15:1) as eluent to give 128 mg. of the title compound having the following physical characteristics:

TLC (developing solvent, benzene-ethyl acetate = 5:1):-

Rf = 0.41;

IR (liquid film):ν; 1740, 1695, 1680, 1622, 1438, 1356, 1140, 1085, 1038, 995, 880 cm⁻¹;

NMR (CDCl₃ solution): δ; 7.3–6.7 (1H, m), 6.5 (1H, d—d), 5.55–5.15 (2H, m), 4.8–4.9 (2H, m), 4.4–3.2 (7H, m), 3.62 (3H, s), 2.3 (2H, t).

EXAMPLE 1

Methyl 9α,11α-bis(2-tetrahydropyranyloxy)-15ξ-hydroxy-16ξ-chloroprosta-cis-5,trans-13-dienoate 54.7 mg. of sodium borohydride were added to a solution of 546 mg. of methyl 9α,11α-bis(2-tetrahydropyranyloxy)-15-oxo-16ξ-chloroprosta-cis-5,trans-13-dienoate (prepared as described in Reference Example 4) in 15 ml. of methanol at −30° C., and the mixture was stirred at the same temperature for 1 hour. The reaction mixture was then diluted with 50 ml. of ethyl acetate, washed with a dilute aqueous hydrochloric acid solution, an aqueous sodium bicarbonate solution and an aqueous sodium chloride solution, dried over sodium sulphate and concentrated under reduced pressure to give 604 mg. of the title compound having the following physical characteristic:-
TCL (developing solvent, benzene-ethyl acetate = 2:1):
Rf = 0.53 and Rf = 0.61.

EXAMPLE 2

Methyl 9α,11α,15α-trihydroxy-16ξ-chloroprosta-cis-5,trans-13-dienoate [or 16ξ-chloro-PGF$_{2α}$ methyl ester]

604 mg. of methyl 9α,11α-bis(2-tetrahydropyranyloxy)-15ξ-hydroxy-16ξ-chloroprosta-cis-5,trans-13-dienoate (prepared as described in Example 1) were dissolved in a mixture of 1.26 ml. of tetrahydrofuran and 12.6 ml. of a 65% acetic acid aqueous solution and the reaction mixture was stirred at 60° C. for 30 minutes and then concentrated under reduced pressure. The residue was purified by column chromatography on silica gel using a mixture of cyclohexane and ethyl acetate (1:1) as eluent to give 226 mg. of the title compound and 102 mg. of its 15β-hydroxy isomer having the following physical characteristics:-
TLC (developing solvent, ethyl acetate): Rf = 0.3; (15β-hydroxy isomer, Rf = 0.4);
IR (liquid film): ν; 3360, 1740, 1435, 1375, 1247, 1055, 980 cm$^{-1}$;
NMR (CDCl$_3$ solution): δ; 5.75–5.52 (2H, m), 5.52–5.2 (2H, m), 4.3–4.04 (1H, m), 4.04–3.5 (3H, m), 3.67 (3H, s), 2.33 (2H, t).

REFERENCE EXAMPLE 5

Methyl 9α-hydroxy-11α,15α-bis(trimethylsilyloxy)-16ξ-chloroprosta-cis-5,trans-13-dienoate 1.24 ml. of trimethylsilyldiethylamine were added to a solution of 260 mg. of 16ξ-chloro-PGF$_{2α}$methyl ester (prepared as described in Example 2) in 3.3 ml. of dry acetone at 0° C. and the reaction mixture was stirred at the same temperature for 1.5 hours, and then concentrated under reduced pressure to give 350 mg. of the title compound having the following physical characteristics:
TLC (developing solvent, cyclohexane-ethyl acetate = 3:1): Rf =0.4.

EXAMPLE 3

Methyl 9-oxo-11α,15α-bis(trimethylsilyloxy)-16ξ-chloroprosta-cis-5,trans-13-dienoate Under an atmosphere of nitrogen, 0.26 ml. of dimethyl sulphide were added to a solution of 393 mg. of N-chlorosuccinimide in 10 ml. of dry toluene and the reaction mixture was cooled to −26° C. There was then added a solution of 350 mg. of methyl 9α-hydroxy-11α,15α-bis(trimethylsilyloxy)-16ξ-chloroprosta-cis-5,trans-13-dienoate (prepared as described in Reference Example 5) in 2 ml. of dry toluene. After stirring at the same temperature for 2 hours, a solution of 0.83 ml. of triethylamine in 1 ml. of dry pentane was added and the mixture stirred at −15° C., for 15 minutes, and then at room temperature for 15 minutes. The reaction mixture was extracted with diethyl ether. The organic solution was washed with a dilute aqueous hydrochloric acid solution, an aqueous sodium bicarbonate solution and an aqueous sodium chloride solution, dried over sodium sulphate and concentrated under reduced pressure to give 327 mg. of the title compound having the following physical characteristic:
TLC (developing solvent, cyclohexane-ethyl acetate = 3:1): Rf = 0.46.

EXAMPLE 4

Methyl 9-oxo-11α,15α-dihydroxy-16ξ-chloroprosta-cis-5,trans-13-dienoate [or 16ξ-chloro-PGE$_2$ methyl ester]

2 ml. of a saturated aqueous oxalic acid solution were added to a solution of 327 mg. of methyl 9-oxo-11α,15α-bis(trimethylsilyloxy)-16ξ-chloroprosta-cis-5,trans-13-dienoate (prepared as described in Example 3) in 10 ml. of ethyl acetate. After stirring for 2 hours at room temperature, the reaction mixture was diluted with 50 ml. of ethyl acetate, washed with an aqueous sodium bicarbonate solution, water and an aqueous sodium chloride solution, dried over sodium sulphate and concentrated under reduced pressure. The residue was purified by column chromatography on silica gel using a mixture of cyclohexane and ethyl acetate (7:5) as eluent to give 83 mg. of the title compound having the following physical characteristics:
TLC (developing solvent, ethyl acetate): Rf = 0.41;
IR (liquid film): ν; 3360, 1740, 1720, 1420, 1240, 1180, 1095, 980 cm$^{-1}$;
NMR (CDC$_3$ solution): δ; 5.72–5.61 (2H, m), 5.40–5.20 (2H, m), 4.45–3.75 (3H, m), 3.66 (3H, s), 2.76 (2H,d—d).

REFERENCE EXAMPLE 6

Methyl 9α-acetoxy-11α-(2-tetrahydropyranyloxy)-15-oxo-prosta-cis-5,trans-13-dienoate 457 mg. of sodium hydride (63% content) were suspended in 150 ml. of anhydrous tetrahydrofuran. With stirring under an atmosphere of nitrogen, 2.89 g. of dimethyl 2-oxo-heptylphosphonate in 7 ml. of anhydrous tetrahydrofuran were added dropwise to the suspension and the mixture was stirred at room temperature for 30 minutes until the solution became clear. 3.96 g. of 1α-acetoxy-2α-(6-methoxycarbonylhex-cis-2-enyl)-3β-formyl-4α-(2-tetrahydropyranyloxy)-cyclopentane (prepared as described hereafter) in 30 ml. of anhydrous tetrahydrofuran were added and the reaction mixture was stirred at room temperature for 2 hours. The reaction mixture was then neutralized with acetic acid. The mixture was filtered through a pad of silica gel, and the filtrate was concentrated under reduced pressure. The residue was purified by column chromatography on silica gel using a mixture of benzene and ethyl acetate (20:1) as eluent to give 4.15 g. of the title compound having the following physical characteristics:

TLC (developing solvent, benzene-ethyl acetate = 2:1): Rf = 0.48;

IR (liquid film):ν; 1740, 1695, 1670, 1625 cm$^{-1}$;

NMR (CDCl$_3$ solution): δ; 6.70 and 6.44 (1H, d—d), 5.99 (1H, d), 5.50–5.05 (2H, m), 5.05–4.70 (1H, m), 4.60–4.20 (1H, m), 3.53 (3H, s), 2.00 (3H, s).

1α-Acetoxy-2α-(6-methoxycarbonylhex-cis-2-enyl)-3β-formyl-4α-(2-tetrahydropyranyloxy)cyclopentane, used as a starting material in the above procedure, was prepared from 2-oxa-3-oxo-6-syn-hydroxymethyl-7-anti-acetoxy-cis-bicyclo[3,3,0]octane [prepared as described by E. J. Corey et al., J. Amer. Chem. Soc., 92, 397 (1970)] as follows:

190 g. of 2-oxa-3-oxo-6-syn-hydroxymethyl-7-anti-acetoxy-cis-bicyclo[3,3,0]octane in 1.5 liters of absolute methanol and 130 g. of potassium hydroxide were stirred at room temperature for one hour, and then successively cooled in an ice-bath, and neutralized with hydrochloric acid. The precipitate was filtered off and the filtrate was concentrated under reduced pressure. The residue was washed with ethanol, and then with ethyl acetate, and dried to give 124 g. of 2-oxa-3-oxo-6-syn-hydroxymethyl-7-anti-hydroxy-cis-bicyclo[3,3,0]-octane as white crystallites having the following physical characteristics:

m.p. 119° C.;

IR (KBr tablet): ν; 3350, 2970–2880, 1740, 1480, 1440, 1410, 1380, 1335, 1305, 1270, 1205, 1100, 1080, 1060, 1040, 1020, 1000 and 975 cm$^{-1}$;

NMR (in CDCl$_3$ + deutero dimethyl sulphoxide solution): δ; 5.10–4.60 (1H, m), 4.29 (2H, s), 4.13–3.77 (1H, m), and 3.38 (2H, d);

TLC (developing solvent, methylene chloride - methanol = 20:1): Rf = 0.27.

124 g. of 2-oxa-3-oxo-6-syn-hydroxymethyl-7-anti-hydroxy-cis-bicyclo[3,3,0]octane obtained above were dissolved in absolute pyridine (1.4 liters) and cooled to −40° C. 74 g. of acetic anhydride were added dropwise and the mixture stirred for 5 hours at −40° to −20° C. and then for 16 hours at 0° C. The pyridine was evaporated off under reduced pressure and the residue was dissolved in 1 liter of ethyl acetate. 200 g. of sodium bisulphate were added, stirred vigorously and filtered. The filtrate was concentrated under reduced pressure and the residue was purified by column chromatography on silica gel using a benzene-ethyl acetate mixture (1:3) as eluent to give 112 g. of 2-oxa-3-oxo-6-syn-acetoxymethyl-7-anti-hydroxy-cis-bicyclo[3,3,0]octane as colourless needles having the following physical characteristics:

m.p. 36° to 37° C.;

IR (KBr tablet): ν; 3450, 2960, 2850, 1775, 1740, 1420, 1370, 1250, 1190, 1120, 1090, 1040 and 980 cm$^{-1}$;

NMR (in CDCl$_3$ solution): δ; 5.15–4.60 (1H, m), 4.3–3.75 (3H, m), 3.50 (1H, s) and 2.02 (3H, s);

TLC (developing solvent, methylene chloride - methanol = 20:1): Rf = 0.50.

43 g. of 2-oxa-3-oxo-6-syn-acetoxymethyl-7-anti-hydroxy-cis-bicyclo[3,3,0]octane, obtained as described above, were dissolved in 520 ml. of methylene chloride, 25 g. of 2,3-dihydropyran and 0.52 g. of p-toluenesulphonic acid were added and the mixture was stirred for 20 minutes at room temperature. The reaction mixture was then neutralized with an aqueous solution of sodium bicarbonate, diluted with ethyl acetate, washed with water, dried and concentrated under reduced pressure to give 56 g. of 2-oxa-3-oxo-6-syn-acetoxymethyl-7-anti-(2-tetrahydropyranyloxy)-cis-bicyclo[3,3,0]octane as a colourless oil having the following physical characteristics:

IR (liquid film): ν; 2950–2840, 1775, 1740, 1465, 1440, 1390–1340, 1240, 1180, 1140–1120, 1080, 1040 and 980 cm$^{-1}$;

NMR (in CDCl$_3$ solution): δ; 5.2–4.72 (1H, m), 4.72–4.30 (1H, m), 4.2–3.2 (5H, m) and 2.01 (3H, s);

TLC (developing solvent, methylene chloride - methanol = 20:1): Rf = 0.74.

56 g. of the acetyl ether, prepared as described above, were dissolved in 900 ml. of toluene and cooled to −60° C. 456 ml. of a 25(w/v)% toluene solution of diisobutylaluminium hydride were added and the mixture stirred for 20 minutes at the same temperature; aqueous methanol was added in order to decompose the excess of diisobutylaluminium hydride. The resulting precipitate was filtered off and the filtrate was dried and concentrated under reduced pressure to give 35.2 g. of 2-oxa-3-hydroxy-6-syn-hydroxymethyl-7-anti-(2-tetrahydropyranyloxy)-cis-bicyclo[3,3,0]octane as a colourless oil having the following physical characteristics:

IR (liquid film): ν; 3400, 2940–2860, 1465–1440, 1380, 1355, 1325, 1260, 1200, 1140, 1120, 1075 and 1020 cm$^{-1}$;

TLC (developing solvent, ethyl acetate): Rf = 0.25.

37.6 g. of sodium hydride (content 63.5%) were suspended in 400 ml. of dimethyl sulphoxide and stirred at 70° C. for 1.5 hours to obtain sodium methylsulphinylmethylide. The reaction mixture was allowed to cool to room temperature and then added dropwise to a solution of 226 g. of (4-carboxybutyl)triphenylphosphonium bromide in 460 ml. of dimethyl sulphoxide, the reaction temperature being kept within the range of 20° to 25° C.

A solution of 35.2 g. of 2-oxa-3-hydroxy-6-syn-hydroxymethyl-7-anti-(2-tetrahydropyranyloxy)-cis-bicyclo-[3,3,0]octane, prepared as described above, in 90 ml. of dimethyl sulphoxide was added to the above reaction mixture and stirred at 35° to 40° C. for 1.5 hours. The reaction mixture was poured into 6 liters of ice-water and the neutral substances were removed by extraction with an ethyl acetate-diethyl ether mixture (1:1). The aqueous layer was acidified to pH 2 with saturated aqueous oxalic acid solution and extracted with a diethyl ether-n-pentane mixture (1:1). The organic layer was washed with water, dried over sodium sulphate and concentrated under reduced pressure. The residue was subjected to column chromatography on silica gel using a benzene-methanol mixture (10:1) as eluent to give 35 g. of 2α-(6-carboxyhex-cis-2-enyl)-3β-hydroxymethyl-4α-(2-tetrahydropyranyloxy)cyclopentan-1α-ol as a colourless oil having the following physical characteristics:

IR (liquid film): ν; 3400, 2940–2860, 2300, 1710, 1450, 1435, 1400, 1355, 1245, 1200, 1140, 1120, 1075 and 1025 cm$^{-1}$;

NMR (in CDCl$_3$ solution): δ; 6.20 (3H, s), 5.50–5.10 (2H, m), 4.75–4.36 (1H, m), 4.24–3.85 (2H, m) and 3.85–3.0 (4H, m);

TLC (developing solvent, chloroform - tetrahydrofuran - acetic acid = 10:2:1): Rf = 0.53.

To a solution of 18.8 g. of 2α-(6-carboxyhex-cis-2-enyl)-3β-hydroxymethyl-4α-(2-tetrahydropyranyloxy)-cyclopentan-1α-ol, obtained as described above, in 130 ml. of diethyl ether, a freshly prepared ethereal solution of diazomethane was added with cooling in an ice-bath until the reaction mixture showed a pale yellow colour. The reaction mixture was concentrated in vacuo, and the residue was subjected to column chromatography on silica gel using a cyclohexan-ethyl acetate mixture (2:1) as eluent to give 15.4 g. of 2α-(6-methoxycarbonyl-hex-cis-2-enyl)-3β-hydroxymethyl-4α-(2-tetrahydropyranyloxy)cyclopentan-1α-ol as a colourless oil having the following physical characteristics:

IR (liquid film): ν; 3450, 2950, 2870, 1740, 1440, 1360, 1325, 1250, 1200, 1140, 1120, 1080 and 1025 cm$^{-1}$;

NMR (in CDCl$_3$ solution): δ; 5.55–5.00 (2H, m), 4.78–4.30 (1H, m), 4.20–3.06 (6H, m), 3.55 (3H, s) and 2.97 (2H, s);

TLC (developing solvent, methylene chloride - methanol = 19:1): Rf = 0.43.

13.1 g. of 2α-(6-methoxycarbonylhex-cis-2-enyl)-3β-hydroxymethyl-4α-(2-tetrahydropyranyloxy)cyclopentan-1α-ol, obtained as described above, were dissolved in 250 ml. of absolute methylene chloride, and 25 ml. of pyridine were added. The air in the apparatus was replaced with nitrogen and the contents cooled to −20° C. To the reaction mixture was added dropwise a solution of 5.1 ml. of trimethylchlorosilane in 30 ml. of methylene chloride with stirring and the mixture was stirred at the same temperature for 30 minutes. A sample of the product thus obtained had the following physical characteristic:

TLC (developing solvent, benzene - ethyl acetate = 2:1): Rf = 0.61.

A solution of 2.9 ml. of acetyl chloride in 20 ml. of methylene chloride was added dropwise to the above reaction mixture and stirred at room temperature for 30 minutes. Then 2 ml. of ethanol were added to decompose the excess of acetyl chloride. Pyridine in the reaction mixture was neutralized by the addition of 50 g. of sodium bisulphate, and the resulting precipitate was filtered off. The filtrate was concentrated under reduced pressure to give a residue having the following physical characteristic:

TLC (developing solvent, benzene - ethyl acetate = 2:1): Rf = 0.82.

The residue was dissolved in 300 ml. of ethyl acetate, 100 ml. of aqueous oxalic acid solution were added and the mixture was stirred vigorously at room temperature. The organic layer was separated, washed successively with water, aqueous sodium bisulphate solution, water and an aqueous sodium chloride solution, dried over sodium sulphate and concentrated under reduced pressure to give 13.7 g. of crude product. The crude product was subjected to column chromatography on silica gel using a benzene-ethyl acetate mixture (3:1) as eluent to give 7.45 g. of 1α-acetoxy-2α-(6-methoxycarbonylhex-cis-2-enyl)-3β-hydroxymethyl-4α-(2-tetrahydropyranyloxy)-cyclopentane, 2.40 g. of 1α-hydroxy-2α-(6-methoxycarbonylhex-cis-2-enyl)-3β-hydroxymethyl-4α-(2-tetrahydropyranyloxy)-cyclopentane, 720 mg. of 1α-acetoxy-2α-(6-methoxycarbonylhex-cis-2-enyl)-3β-acetoxymethyl-4α-(2-tetrahydropyranyloxy)cyclopentane, and 1.45 g. of 1α-acetoxy-2α-(6-methoxycarbonylhex-cis-2-enyl)-3β-acetoxymethyl-4α-(2-tetrahydropyranyloxy)cyclopentane.

1α-Acetoxy-2α-(6-methoxycarbonylhex-cis-2-enyl)-3β-hydroxymethyl-4α-(2-tetrahydropyranyloxy)cyclopentane had the following physical characteristic:

IR (liquid film): ν; 3450, 3000, 2950, 2870, 1740, 1440, 1380, 1330, 1250, 1200, 1160, 1140, 1080, 1030, 980, 920, 875 and 815 cm$^{-1}$;

NMR (in CDCl$_3$ solution): δ; 5.45–5.27 (2H, m), 5.16–4.92 (1H, m), 4.76–4.46 (1H, m), 4.27–3.96 (1H, m), 3.67 (3H, s), 2.98–2.64 (1H, m) and 2.05 (3H, s);

TLC (developing solvent, benzene-ethyl acetate = 2:1): Rf = 0.27.

Under an atmosphere of nitrogen, 4.4 ml. of pyridine were dissolved in 80 ml. of methylene chloride, 2.88 g. of chromium trioxide were added with stirring and the mixture was then stirred for 15 minutes. 12 g. of infusorial earth were added to the reaction mixture, and then there was added a solution of 956 mg. of 1α-acetoxy-2α-(6-methoxycarbonylhex-cis-2enyl)-2β-hydroxymethyl-4α-(2-tetrahydropyranyloxy)cyclopentane (prepared as described above) in 20 ml. of methylene chloride. After stirring for 10 minutes, 20 g. of sodium bisulphate were added to the reaction mixture and stirring was continued for a further 10 minutes. The resulting precipitate was filtered off and the filtrate was concentrated under reduced pressure. The residue was subjected to silica gel column chromatography using a benzene-ethyl acetate mixture (5:1) as eluent to give 768 mg. of 1α-acetoxy-2α-(6-methoxycarbonylhex-cis-2-enyl)-3β-formyl-4α-(2-tetrahydropyranyloxy)cyclopentane as a colourless oil having the following physical characteristics:

IR (liquid film) ν; 3000, 2950, 2860, 2725, 2740, 1440, 1380, 1325, 1255, 1200, 1165, 1140, 1085, 1030, 980, 920, 880 and 820 cm$^{-1}$;

NMR (in CDCl$_3$ solution): δ; 9.85–9.68 (1H, m), 5.45–4.96 (1H, m), 4.68–4.48 (1H, m), 4.48–4.25 (1H, m), 3.67 (3H, s), and 2.08 (3H, s);

TLC (developing solvent, benzene-ethyl acetate = 2:1):

Rf = 0.66.

REFERENCE EXAMPLE 7

Methyl 9α-acetoxy-11α-(2-tetrahydropyranyloxy)-15-trimethylsilyloxyprosta-cis-5,trans-13,cis(or trans)-15-trienoate 130 ml. of 0.29M lithium diisopropylamide solution in a mixture of tetrahydrofuran and diethyl ether (10:3) were added dropwise over a period of 3 hours to a solution of 4.15 g. of methyl 9α-acetoxy-11α-(2-tetrahydropyranyloxy)-15-oxoprosta-cis-5, trans-13-dienoate (prepared as described in Reference Example 6) in 20 ml. of tetrahydrofuran under an atmosphere of nitrogen at −78° C. The reaction mixture was stirred at the same temperature for 30 minutes. To the reaction mixture thus obtained, there was added dropwise over a period of 15 minutes a solution of 9.15 g. of trimethylchlorosilane and 2.13 g. of triethylamine in 30 ml. of diethyl ether and the reaction mixture was stirred at −78° C. for 15 minutes, and allowed to warm to room temperature and then stirred for 30 minutes at room temperature. The reaction mixture was then concentrated under reduced pressure. The residue was purified by column chromatography on silica gel using a mixture of cyclohexane and ethyl acetate (10:1) as eluent to give 1.19 g. of the title compound having the following physical characteristics:

TLC (developing solvent, benzene-ethyl acetate =5:1):

Rf = 0.6;

IR (liquid film): ν; 1740, 1660–1610, 1250, 1140, 1080, 1030, 845 cm$^{-1}$.

REFERENCE EXAMPLE 8

Methyl 9α-acetoxy-11α-(tetrahydropyranyloxy)-15-oxo 16ξ-chloroprosta-cis-5,trans-13-dienoate To a solution of 1.872 g. of methyl 9α-acetoxy-11α-(2-tetrahydropyranyloxy)-15-trimethylsilyloxyprosta-cis-5,trans-13,cis(or trans)-15-trienoate (prepared as described in Reference Example 7) in 30 ml. of tetrahydrofuran, there was added dropwise a solution of 2.02 g. of N-chlorosuccinimide in 20 ml. of tetrahydrofuran at −30° C. and the mixture was stirred at the same temperature for hour. The reaction mixture was then quenched with a dilute hydrochloric acid solution and extracted with diethyl ether. The extract was washed with an aqueous sodium bicarbonate solution and an aqueous sodium chloride solution, dried over sodium sulphate, and concentrated under reduced pressure. The residue was purified by column chromatography on silica gel using a mixture f cyclohexane and ethyl acetate (10:1) as eluent to give 186 mg. of the title compound having the following physical characteristics:

TLC (developing solvent, benzene-ethyl acetate = 5:1):
Rf = 0.5;
IR (liquid film): ν; 1740, 1695, 1680, 1625, 1440, 1355, 1140, 1085, 1030, 990, 880 cm=¹;

REFERENCE EXAMPLE 9

Methyl 9α-acetoxy-11α-(2-tetrahydropyranyloxy)-15ξ-hydroxy-16ξ-chloroprosta-cis-5,trans-13-dienoate 20 mg. of sodium borohydride were added to a solution of 186 mg. of methyl 9α-acetoxy-11α-(2-tetrahydropyranyloxy)-5-oxo-16ξ-chloroprosta-cis-5,trans-13-dienoate (prepared as described in Reference Example 8) in 7 ml. of absolute methanol at −26° C. and the mixture was stirred at the same temperature for 2 hours. The reaction mixture was diluted with 50 ml. of ethyl acetate, washed with a dilute aqueous hydrochloric acid solution, an aqueous sodium bicarbonate solution and an aqueous sodium chloride solution, dried over sodium sulphate and concentrated under reduced pressure. The residue was purified by column chromatography ion silica gel using a mixture of benzene and ethyl acetate (9:1) as eluent to give 84 mg. of the title compound having the following physical characteristics:

TLC (developing solvent, benzene - ethyl acetate = 5:1):
Rf = 0.2;
IR (liquid film): ν; 3360, 1740, 1440, 1360, 1140, 1080, 1030, 980 cm⁻¹.

REFERENCE EXAMPLE 10

Methyl 9α-acetoxy-11α,15ξ-bis(2-tetrahydropranyloxy)-16ξ-chlorroprosta-cis-5,trans-13-dienoate A catalytic amount of p-toluenesulphonic acid and 0.1 ml. of 2,3-dihydropyran were added to a solution of 84 mg. of methyl 9α-acetoxy-11α-(2-tetrahydropyranyloxy)-15ξ-hydroxy-16ξ-chloroprosta-cis-5,trans-13-dienoate (prepared as described in Reference Example 9) in 5 ml. of methylene chloride, and the reaction mixture was stirred at room temperature for 15 minutes and then diluted with 20 ml. of ethyl acetate. The mixture was washed with an aqueous sodium bicarbonate solution and an aqueous sodium chloride solution, dried over sodium sulphate and concentrated under reduced pressure to give 98 mg. of the title compound having the following physical characteristics:

TLC (developing solvent, benzene-ethyl acetate = 5:1):
Rf = 0.38;
IR (liquid film): ν; 1740, 1440, 1365, 1140, 1080, 1030, 975 cm⁻¹.

REFERENCE EXAMPLE 11

Methyl 9α-hydroxy-11α,15ξ-bis(2-tetrahydropyranyloxy)-16ξ-chloroprosta-cis-5,trans-13-dienoate 24 mg. of potassium carbonate were added to a solution of 98 mg. of methyl 9α-acetoxy-11α,15ξ-bis(2-tetrahydropyranyloxy)-16ξ-chloroprosta-cis-5,trans-13-dienoate (prepared as described in Reference Example 10) in 1 ml. of methanol and the mixture was stirred at 40° C. for 1 hour. After cooling to room temperature, the reaction mixture was diluted with 20 ml. of ethyl acetate, washed with a dilute aqueous hydrochloric acid solution, an aqueous sodium bicarbonate solution and an aqueous sodium chloride solution, dried over sodium sulphate and concentrated under reduced pressure to give 99 mg. of the title compound having the following physical characteristics:

TLC (developing solvent, benzene-ethyl acetate = 5:1):
Rf = 0.14;
IR (liquid film): ν; 3370, 1740, 1440, 1360, 1140, 1085, 1025, 980 cm⁻¹.

EXAMPLE 5

Methyl 9-oxo-11α,15ξ-bis(2-tetrahydropyranyloxy)-16ξ-chloroprosta-cis-5,trans-13-dienoate Under an atmosphere of nitrogen, 0.07 ml. of dimethyl sulphide were added to a solution of 98 mg. of N-chlorosuccinimide in 2 ml. of dry toluene and the mixture was cooled to −26° C. There was then added a solution of 99 mg. of methyl 9α-hydroxy-11α,15ξ-bis(2-tetrahydropyranyloxy)-16ξ-chloroprosta-cis-5,trans-13-dienoate (prepared as described in Reference Example 11) in 2 ml. of dry toluene. After stirring at the same temperature for 2 hours, a solution of 0.2 ml. of triethylamine in 0.3 ml. of dry pentane was added and the reaction mixture was stirred at −26° C. for 15 minutes and then stirred at room temperature for 15 minutes. The reaction mixture was diluted with 220 ml. of diethyl ether, washed with a dilute aqueous hydrochloric acid solution, an aqueous sodium bicarbonate solution and an aqueous sodium chloride solution, dried over sodium sulphate and concentrated under reduced pressure. The residue was purified by column chromatography on silica gel using a mixture of cyclohexane and ethyl acetate (10:1) as eluent to give 70 mg. of the title compound having the following physical characteristics:

TLC (developing solvent, benzene-ethyl acetate = 5:1):
Rf = 0:25;
IR (liquid film): ν; 1740, 1720, 1430, 1120, 1090, 1030, 980 cm⁻¹.

EXAMPLE 6

Methyl 9-oxo-11α,15α-dihydroxy-16ξ-chloroprosta-cis-5,trans-13-dienoate [or 16ξ-chloro-PGE$_2$ methyl ester]

70 mg. of methyl 9-oxo-11α,15ξ-bis(2-tetrahydropyranyloxy)-15ξ-chloroprosta-cis-5,trans-13-dienoate (prepared as described in Example 5) were dissolved in a mixture of 0.1 ml. of tetrahydrofuran and 1 ml. of 65% aqueous acetic acid and the reaction mixture was stirred at 60° C. for 20 minutes and then concentrated under reduced pressure. The resulting oil was dissolved in 20 ml. of ethyl acetate, and washed with an aqueous sodium bicarbonate solution and an aqueous sodium chloride solution, dried over sodium sulphate and concentrated under reduced pressure. The residue was purified by column chromatography on silica gel using a mixture of benzene and ethyl acetate (5:1) as eluent to give 28 mg. of the title compound and 14 mg. of its 15β-hydroxy isomer having the following physical characteristics:

TLC (developing solvent, ethyl acetate): Rf = 0.41; (15β-hydroxy isomer, Rf = 0.51);

IR (liquid film): ν; 3360, 1740, 1720, 1420, 1240, 1180, 1095, 980 cm$^{-1}$;

NMR (CDCl$_3$ solution): δ; 5.72–5.61 (2H, m), 5.40–5.20 (2H, m), 4.45–3.75 (3H, m), 3.66 (3H, s), 2.76 (2H, d—d).

REFERENCE EXAMPLE 12

Methyl 9α-acetoxy-11α-(2-tetrahydropyranyloxy)-15-oxo-16ξ-chloroprosta-cis-5,trans-13-dienoate By proceeding as described in Reference Example 6 but replacing the dimethyl 2-oxo-heptylphosphonate by 2.822 g. of dimethyl 2-oxo-3-chloroheptylphosphonate (prepared as described hereafter) dissolved in 5 ml. of tetrahydrofuran and utilizing a suspension of 240 mg. of sodium hydride in 50 ml. of tetrahydrofuran and a solution of 3.96 g. of 1α-acetoxy-2α-(6-methoxycarbonyl-hex-cis-2-enyl)-3β-formyl-4α-(2-tetrahydropyranyloxy)-cylopentane (prepared as described in Reference Example 6) in 10 ml. of tetrahydrofuran, there were obtained 4.162 g. of the title compound having the following physical characteristics:

TLC (developing solvent, benzene-ethyl acetate = 5:1):

Rf = 0.45;

IR (liquid film): ν; 1740, 1695, 1622, 1245, 1030 cm$^{-1}$;

NMR (CDCl$_3$ solution): δ; 7.04 (1H, dd), 6.6 (1H, d), 5.55–5.22 (2H, m), 5.22–4.95 (1H, m), 4.72–4.49 (1H, m), 4.36 (1H, t), 4.4–3.2 (3H, m), 3.67 (3H, s), 2.07 (3H, s).

Dimethyl 2-oxo-3-chloroheptylphosphonate, used as a starting material in the above procedure, was prepared as follows:

Under an atmosphere of nitrogen, a solution of 6.66 g. of dimethyl 2-oxo-heptylphosphonate in 20 ml. of tetrahydrofuran was added to a suspension of 720 mg. of sodium hydride in 100 ml. of tetrahydrofuran at room temperature and the mixture was stirred at the same temperature for 20 minutes. After cooling to 0° C., there were added to the solution 24 ml. of a 1.38M solution of n-butyllithium in n-hexane at that temperature and the mixture was stirred for 30 minutes. After cooling to −78° C., there was added to the solution thus obtained dropwise a solution of 5.82 g. of benzenesulphonyl chloride in 20 ml. of tetrahydrofuran and the mixture was stirred at −78° C. for 30 minutes and then at room temperature for one hour. The reaction mixture was acidified with acetic acid, diluted with 200 ml. of ethyl acetate, washed with an aqueous solution of sodium chloride, dried over sodium sulphate and concentrated under reduced pressure. The residue was purified by column chromatography on silica gel using a mixture of benzene and ethyl acetate (1:3) as eluent to give 4.56 g. of dimethyl 2-oxo-3-chloroheptylphosphonate having the following physical characteristics:

TLC (developing solvent, ethyl acetate): Rf = 0.41;

IR (liquid film): ν; 1725, 1260, 1190, 1100–1000, 900–780 cm$^{-1}$;

NMR (CDCl$_3$ solution): δ; 4.44 (1H, dd), 3.80 (6H, d), 3.71–3.02 (2H, m).

REFERENCE EXAMPLE 13

Methyl 9α-acetoxy-11α-(2-tetrahydropyranyloxy)-15α-hydroxy-16ξ-chloroprosta-cis-5,trans-13-dienoate By proceeding as described in Example 1 but replacing the methyl 9α,11α-bis(2-tetrahydropyranyloxy)-15-oxo-16ξ-chloroprosta-cis-5,trans-13-dienoate by 4.169 g. of methyl 9α-acetoxy-11α-(2-tetrahydropyranyloxy)-15-oxo-16ξ-chloroprosta-cis-5,trans-13-dienoate (prepared as described in Reference Example 12) dissolved in 80 ml. of methanol and utilizing 361 mg. of sodium borohydride, there were obtained 2.98 g. of the title compound and 1.06 g. of its 15β-hydroxy isomer. The title compound showed the following physical characteristics:

TLC (developing solvent, benzene-ethyl acetate = 2:1):

Rf = 0.36, (15β-hydroxy isomer, Rf = 0.43);

IR (liquid film): ν; 3600–3100, 1740, 1245, 1100–1000 cm$^{-1}$;

NMR (CDCl$_3$ solution): δ; 5.87–5.60 (2H, m), 5.60–5.27 (2H, m), 5.27–4.95 (1H, m), 4.72–4.55 (1H, m), 3.70 (3H, s), 2.07 (3H, s).

REFERENCE EXAMPLE 14

Methyl 9α-acetoxy-11α,15α-bis(2-tetrahydropyranyloxy)-16ξ-chloroprosta-cis-5,trans-13-dienoate By proceeding as described in Reference Example 2 but replacing the 15-oxo-PGF$_{2α}$ methyl ester by 2.98 g. of methyl 9α-acetoxy-11α-(2-tetrahydropyranyloxy)-15α-hydroxy-16ξ-chloroprosta-cis-5,trans-13-dienoate (prepared as described in Reference Example 13) dissolved in 30 ml. of methylene chloride and utilizing 15 mg. of p-toluenesulphonic acid and 952 mg. of 2,3-dihydropyran, there were obtained 3.7 g. of the title compound having the following physical characteristics:

TLC (developing solvent, benzene-ethyl acetate = 2:1):

Rf = 0.50;

IR (liquid film): ν; 1740, 1465–1405, 1390–1130, 1240, 1110, 1070, 1050–1000, 990 cm$^{-1}$;

NMR (CDCl$_3$ solution): δ; 5.65–5.50 (2H, m), 5.50–5.20 (2H, m), 5.20–4.95 (1H, m), 4.90–4.50 (2H, m), 3.68 (3H, s), 2.05 (3H, s).

EXAMPLE 7

Methyl 9α-hydroxy-11α,15α-bis(2-tetrahydropyranyloxy)-16ξ-chloroprosta-cis-5,trans-13-dienoate By proceeding as described in Reference Example 11 but replacing the methyl 9α-acetoxy-11α,15ξ-bis(2-tetrahydropyranyloxy)-16ξ-chloroprosta-cis-5,trans-13-dienoate by 3.7 g. of methyl 9α-acetoxy-11α,15α-bis(2-tetrahydropyranyloxy)-16ξ-chloroprosta-cis-5,trans-13-dienoate (prepared as described in Reference Example 14) dissolved in 40 ml. of methanol and utilizing 616 mg. of potassium carbonate, there were obtained 2.961 g. of the title compound having the following physical characteristics:-

TLC (developing solvent, benzene-ethyl acetate = 2:1):
Rf = 0.42;
IR (liquid film): $\nu$; 3600–3100, 1740, 1460–1420, 1200, 1120–1100, 1075, 1010, 970 cm$^{-1}$;
NMR (CDCl$_3$ solution: $\delta$; 5.72–5.20 (4H, m), 4.95–4.59 (2H, m), 4.42–3.20 (8H, m), 3.68 (3H, s).

EXAMPLE 8

Methyl 9-oxo-11α,15α-bis(2-tetrahydropyranyloxy)-16ξ-chloroprosta-cis-5,trans-13-dienoate By proceeding as described in Example 3 but replacing the methyl 9α-hydroxy-11α,15α-bis(trimethylsilyloxy)-16ξ-chloroprosta-cis-5,trans-13-dienoate by 570 mg. of methyl 9α-hydroxy-11α,15α-bis(2-tetrahydropyranyloxy)-16ξ-chloroprosta-cis-5,trans-13-dienoate (prepared as described in Example 7) dissolved in 10 ml. of toluene and utilizing a suspension of 862 mg. of N-chlorosuccinimide in 10 ml. of toluene, 0.1 ml. of dimethyl sulphide and 1 ml. of triethylamine, there were botained 544 mg. of the title compound having the following physical characteristics:-

TLC (developing solvent, benzene-ethyl acetate = 2:1):
Rf = 0.50;
IR (liquid film): $\nu$; 1740, 1710, 1435, 1390–1310, 1240, 1160, 1130, 1080, 1030–1010, 975 cm$^{-1}$;
NMR (CDCl$_3$ solution): $\delta$; 5.85–5.51 (2H, m), 5.51–5.20 (2H, m), 4.85–4.50 (2H, m), 4.50–3.20 (7H, m), 3.67 (3H, s).

EXAMPLE 9

Methyl 9-oxo-11α,15α-dihydroxy-16ξ-chloroprosta-cis-5,trans-13-dienoate [or 16ξ-chloro-PGE$_2$ methyl ester]

By proceeding as described in Example 2 but replacing the methyl 9α,11α-bis(2-tetrahydropyranyloxy)-15ξ-hydroxy-16ξ-chloroprosta-cis-5,trans-13-dienoate by 520 mg. of methyl 9-oxo-11α,15α-bis(2-tetrahydropyranyloxy)-16ξ-chloroprosta-cis-5,trans-13-dienoate (prepared as described in Example 8) dissolved in a mixture of 1 ml. of tetrahydrofuran and 10 ml. of 65% aqueous acetic acid, there were obtained 247 mg. of the title compound having the same physical characteristics as those of the product of Example 6.

EXAMPLE 10

Methyl 9α-hydroxy-11α,15α-bis(2-tetrahydropyranyloxy)-16ξ-chloroprost-trans-13-enoate 1.0 g. of methyl 9α-hydroxy-11α,15α-bis(2-tetrahydropyranyloxy)-16ξ-chloroprosta-cis-5,trans-13-dienoate (prepared as described in Example 7) was hydrogenated at a pressure of one atmosphere in 30 ml. of methanol containing 330 mg. of 5% palladium on charcoal. The reduction was stopped after the absorption of one equivalent of hydrogen gas. The catalyst was filtered off and the filtrate was concentrated under reduced pressure to give 982 mg. of the crude title compound having the following physical characteristics:

TLC (developing solvent, benzene-ethyl acetate = 2:1):
Rf = 0.33;
IR (liquid film): $\nu$; 3600–3200, 1740, 1715, 1622, 1445–1420, 1390–1330, 1240, 1200, 1140–1100, 1075, 1025–1010, 975 cm$^{-1}$;
NMR (CDCl$_3$ solution): $\delta$; 5.73–5.30 (2H, m), 4.88–4.45 (2H, m), 4.35–3.25 (8H, m), 3.62 (3H, s).

EXAMPLE 11

Methyl 9-oxo-11α,15α-bis(2-tetrahydropyranyloxy)-16ξ-chloroprost-trans-13-enoate By proceeding as described in Example 3 but replacing the methyl 9α-hydroxy-11α,15α-bis(trimethylsilyloxy)-16ξ-chloroprosta-cis-5,trans-13-dienoate by 982 mg. of methyl 9α-hydroxy-11α,15α-bis(2-tetrahydropyranyloxy)-16ξ-chloroprost-trans-13-enoate (prepared as described in Example 10) dissolved in 18 ml. of toluene and utilizing a suspension of 1.38 g. of N-chlorosuccinimide in 18 ml. of toluene, 0.18 ml. of dimethyl sulphide and 1.8 ml. of triethylamine, there were obtained 769 mg. of the title compound having the following physical characteristics:

TLC (developing solvent, benzene-ethyl acetate = 2:1):
Rf = 0.58;
IR (liquid film): $\nu$; 1740, 1470–1420, 1390–1335, 1262, 1242, 1200, 1142–1100, 1080, 1060–1010, 978 cm$^{-1}$;
NMR (CDCl$_3$ solution): $\delta$; 5.9–5.5 (2H, m), 4.92–4.5 (2H, m), 4.5–3.2 (7H, m), 3.67 (3H, s).

EXAMPLE 12

Methyl 9-oxo-11α,15α-dihydroxy-16ξ-chloroprost-trans-13-enoate [or 16ξ-chloro-PGE$_1$ methyl ester]

By proceeding as described in Example 2 but replacing the methyl 9α,11α-bis(2-tetrahydropyranyloxy)-15ξ-hydroxy-16ξ-chloroprosta-cis-5,trans-13-dienoate by 769 mg. of methyl 9-oxo-11α,15α-bis(2-tetrahydropyranyloxy)-16ξ-chloroprost-trans-13-enoate (prepared as described in Example 11) dissolved in a mixture of 1.5 ml. of tetrahydrofuran and 13 ml. of 65% aqueous acetic acid, there were obtained 254 mg. of the title compound having the following physical characteristics:

TLC (developing solvent, ethyl acetate): Rf = 0.48;
IR (liquid film): $\nu$; 3600–3100, 1740, 1715, 1460, 1433, 1245, 1200, 1180, 1075, 970 cm$^{-1}$;
NMR (CDCl$_3$ solution): $\delta$; 5.82–5.60 (2H, m), 4.35–3.10 (3H, m), 3.66 (3H, s), 2.74 (1H, dd).

REFERENCE EXAMPLE 15

Methyl 9α-acetoxy-11β-(2-tetrahydropyranyloxy)-15-oxo-16ξ-chloroprost-trans-13-enoate By proceeding as described in Reference Example 12 but replacing the 1α-acetoxy-2α-(6-methoxycarbonyl-hex-cis-2-enyl)-3β-formyl-4α-(2-tetrahydropyranyloxy)-cyclopentane by 796 mg. of 1α-acetoxy-2α-(6-methoxycarbonylhexyl)-3β-formyl-4β-(2-tetrahydropyranyloxy)-cyclopentane (prepared as described hereafter) dissolved in 2 ml. of tetrahydrofuran and utilizing a suspension of 62.5 mg. of sodium hydride in a mixture of 10 ml. of tetrahydrofuran and 0.5 ml. of hexamethylphosphotriamide and 769 mg. of dimethyl 2-oxo-3-chloroheptylphosphonate (prepared as described in Reference Example 12), there were obtained 628 mg. of the title compound and 245 mg. of the starting material. The title compound showed the following physical characteristics:

TLC (developing solvent, benzene-ethyl acetate = 4:1):
Rf = 0.45;
IR (liquid film): ν; 1740, 1695, 1680, 1625, 1440, 1435, 1370, 1240, 1200, 1170, 1113, 1075, 1020, 980 cm$^{-1}$;
NMR (CDCl$_3$ solution): δ; 7.32–6.30 (1H, m), 6.42 (1H, d), 5.45–5.15 (1H, m), 4.74–4.18 (3H, m), 4.10–3.30 (2H, m), 3.66 (3H, s), 2.04 (3H, s).

1α-Acetoxy-2α-(6-methoxycarbonylhexyl)-3β-formyl-4β-(2-tetrahydropyranyloxy)cyclopentane, used as a starting material in the above procedure, was prepared from 2-oxa-3-oxo-6-syn-acetoxymethyl-7-anti-hydroxy-cis-bicyclo[3,3,0]octane (prepared as described in Reference Example 6) as follows:

1.
2-Oxa-3-oxo-6-syn-acetoxymethyl-7-anti-methylsulphonyloxy-cis-bicyclo[3,3,0]octane Under an atmosphere of nitrogen, 6.87 g. of methanesulphonyl chloride were added portionwise to a solution of 10.7 g. of 2-oxa-3-oxo-6-syn-acetoxymethyl-7-anti-hydroxy-cis-bicyclo[3,3,0]octane and 6.06 g. of triethylamine in 150 ml. of methylene chloride at −20° C. and the mixture was stirred at the same temperature for one hour. The reaction mixture was quenched with dilute hydrochloric acid and extracted with ethyl acetate. The extract was washed with water and an aqueous solution of sodium chloride, dried over sodium sulphate and concentrated under reduced pressure to give 16 g. of the crude title compound having the following physical characteristic:

TLC (developing solvent, ethyl acetate): Rf = 0.39.

2.
2-Oxa-3-oxo-6-syn-acetoxymethyl-7-syn-benzoyloxy-cis-bicyclo[3,3,0]octane To a solution of 16 g. of 2-oxa-3-oxo-6-syn-acetoxymethyl-7-anti-methylsulphonyloxy-cis-bicyclo[3,3,0]octane (prepared as described above) in 100 ml. of N,N-dimethylformamide were added 9.7 g. of sodium benzoate at room temperature and the mixture was heated to 90° C. and then stirred at that temperature for one hour. To the solution were added 30 ml. of dimethyl sulphoxide and the mixture stirred at 90° C. for 4.5 hours. After cooling to room temperature, the reaction mixture was diluted with 180 ml. of water and extracted with ethyl acetate. The extract was washed with water and an aqueous solution of sodium chloride, dried over sodium sulphate and concentrated under reduced pressure. The residue was purified by column chromatography on silica gel using a mixture of benzene and ethyl acetate (3:1) as eluent to give 12.592 g. of the title compound having the following physical characteristics:

TLC (developing solvent, benzene-ethyl acetate = 1:1):
Rf = 0.45;
NMR (CDCl$_3$ solution): δ; 8.25–7.8 (2H, m), 7.65–7.23 (3H, m), 5.80–5.45 (1H, m), 5.45–4.90 (1H, m), 4.40–4.15 (2H, m), 2.05 (3H, s).

3.
2-Oxa-3-oxo-6-syn-hydroxymethyl-7-syn-hydroxy-cis-bicyclo[3,3,0]octane

To a solution of 12.6 g. of 2-oxa-3-oxo-6-syn-acetoxymethyl-7-syn-benzyloxy-cis-bicyclo[3,3,0]octane (prepared as described above) in 60 ml. of methanol were added 6.9 g. of potassium carbonate and the mixture stirred at 50° C. for 2.5 hours. The reaction mixture was acidified to pH 1 with conc. hydrochloric acid, stirred at room temperature for 30 minutes and filtered. The filtrate was concentrated under reduced pressure to give 8.4 g. of the crude title compound having the following physical characteristic:

TLC (developing solvent, ethyl acetate-methanol = 95:1):
Rf = 0.22.

4.
2-Oxa-3-oxo-6-syn-acetoxymethyl-7-syn-hydroxy-cis-bicyclo[3,3,0]octane

Under an atmosphere of nitrogen, a solution of 3.56 ml. of acetyl chloride in 60 ml. of methylene chloride was added dropwise to a solution of 8.4 g. of 2-oxa-3-oxo-6-syn-hydroxymethyl-7-syn-hydroxy-cis-bicyclo[3,3,0]octane (prepared as described above) in a mixture of 25 ml. of pyridine and 40 ml. of methylene chloride at −20° C. and the mixture was stirred at the same temperature for 3 hours. The reaction was then acidified to pH 1 with conc. hydrochloric acid, poured into 150 ml. of a saturated aqueous solution of ammonium sulphate and extracted with ethyl acetate. The extract was dried over sodium sulphate and concentrated under reduced pressure to give 4.01 g. of the crude title compound as white powder having the following physical characteristics:

TLC (developing solvent, ethyl acetate): Rf = 0.36;
NMR $$(CD_3OD + CD_3\overset{\overset{\text{O}}{\|}}{S}CD_3 \text{ solution}):$$

δ; 5.17–4.87 (1H, m), 4.38–4.02 (3H, m), 2.02 (3H, s).

5.
2-Oxa-3-oxo-6-syn-acetoxymethyl-7-syn-(2-tetrahydropyranyloxy)-cis-bicyclo[3,3,0]octane To a solution of 4 g. of 2-oxa-3-oxo-6-syn-acetoxymethyl-7-syn-hydroxy-cis-bicyclo[3,3,0]octane (prepared as described above) in 70 ml. of methylene chloride were added 50 mg. of p-toluenesulphonic acid and 2.52 g. of 2,3-dihydropyran and the mixture was stirred at room temperature for 30 minutes. The reaction mixture was diluted with ethyl acetate, washed with an aqueous solution of sodium bicarbonate and an aqueous solution of sodium chloride, dried over sodium sulphate and concentrated under reduced pressure to give 6.3 g. of the crude title compound having the following physical characteristic:

TLC (developing solvent, ethyl acetate): Rf = 0.54.

6.
2-Oxa-3-hydroxy-6-syn-hydroxymethyl-7-syn-(2-tetrahydropyranyloxy)-cis-bicyclo[3,3,0]octane Under an atmosphere of nitrogen, 26.5 ml. of a 25(w/v)% solution of diisobutylaluminium hydride in toluene were added portionwise to a solution of 6.3 g. of 2-oxa-3-oxo-6-syn-acetoxymethyl-7-syn-(2-tetrahydropyranyloxy)-cis-bicyclo[3,3,0]octane (prepared as described above) in 70 ml. of toluene at −78° C. and the mixture was stirred at the same temperature for 40 minutes. Aqueous methanol was added in order to decompose the excess of diisobutylaluminium hydride and the resulting precipitate was filtered off. The filtrate was concentrated under reduced pressure and the residue was purified by column chromatography on silica gel using a mixture of benzene and ethyl acetate (2:5) as eluent to give 3.627 g. of the title compound having the following physical characteristics:

TLC (developing solvent, ethyl acetate): Rf = 0.15;
NMR (CDCl$_3$ solution): δ; 5.70–5.45 (1H, m), 5.15–4.27 (3H, m), 4.15–3.30 (4H, m).

7.
2α-(6-Carboxyhex-cis-2-enyl)-3β-hydroxymethyl-4β-(2-tetrahydropyranyloxy)-cyclopentan-1α-ol A suspension of 4.27 g. of sodium hydride (63% content) in 90 ml. of dimethyl sulphoxide was stirred at 70° C. for one hour to obtain sodium methylsulphinylmethylide. The reaction mixture was allowed to cool to room temperature and then added dropwise to a solution of 24.8 g. of (4-carboxybutylidene)-triphenylphosphonium bromide in 50 ml. of dimethyl sulphoxide, the reaction temperature being kept within the range of 20° to 25° C.

To the solution thus obtained was added a solution of 3.6 g. of 2-oxa-3-hydroxy-6-syn-hydroxymethyl-7-syn-(2-tetrahydropyranyloxy)-cis-bicyclo[3,3,0]octane (prepared as described above) in 10 ml. of dimethyl sulphoxide at room temperature and the mixture stirred at room temperature for 2 hours. The reaction mixture was poured into 500 ml. of ice-water and the neutral substance was removed by extraction with a mixture of ethyl acetate and diethyl ether (1:1). The aqueous layer was acidified to pH 2 with a saturated aqueous solution of oxalic acid and extracted with a mixture of diethyl ether and n-pentane (1:1). The extract was washed with water, dried over sodium sulphate and concentrated under reduced pressure to give 4.7 g. of the crude title compound having the following physical characteristic:

TLC (developing solvent, ethyl acetate-methanol = 95:5):
Rf = 0.39.

8.
2α-(6-Methoxycarbonylhex-cis-2-enyl)-3β-hydroxymethyl-4β-(2-tetrahydropyranyloxy)cyclopentan-1α-ol To a solution of 4.7 g. of 2α-(6-carboxyhex-cis-2-enyl)-3β-hydroxymethyl-4β-(2-tetrahydropyranyloxy)-cyclopentan-1α-ol (prepared as described above) in 50 ml. of diethyl ether, a freshly prepared solution of diazomethane in diethyl ether was added with cooling in an ice-bath until the reaction mixture showed a pale yellow colour. The reaction mixture was concentrated under reduced pressure and the residue was purified by column chromatography on silica gel using a mixture of ethyl acetate and benzene (2:1) as eluent to give 3.98 g. of the title compound having the following physical characteristics:

TLC (developing solvent, ethyl acetate): Rf = 0.43;
IR (liquid film): ν; 3400, 1738, 1432, 1200, 1158, 1120, 1070, 1023, 993 cm$^{-1}$;
NMR (CDCl$_3$ solution): δ; 5.65–5.23 (2H, m), 4.85–4.14 (3H, m), 4.14–3.25 (4H, m), 3.65 (3H, s).

9.
1α-Acetoxy-2α-(6-methoxycarbonylhex-cis-2-enyl)-3β-hydroxymethyl-4β-(2-tetrahydropyranyloxy)cyclopentane Under an atmosphere of nitrogen, 1.79 g. of trimethylsilyldiethylamine were added dropwise to a solution of 3.98 g. of 2α-(6-methoxycarbonylhex-cis-2-enyl)-3β-hydroxymethyl-4β-(2-tetrahydropyranyloxy)-cyclopentan-1α-ol (prepared as described above) in 50 ml. of acetone at −20° C. and the mixture was stirred at the same temperature for one hour and then at room temperature for 1.5 hours. The reaction mixture was concentrated under reduced pressure. The residue showed the following physical characteristic:

TLC (developing solvent, benzene-ethyl acetate = 1.1):
Rf = 0.47.

The crude product thus obtained was dissolved in a mixture of 30 ml. of methylene chloride and 1.97 g. of pyridine and to the solution were added dropwise 1.57 g. of acetyl chloride at room temperature. After one hour of stirring at room temperature, the reaction mixture was diluted with ethyl acetate, washed with 0.5N hydrochloric acid, an aqueous solution of sodium bicarbonate and an aqueous solution of sodium chloride, dried over sodium sulphate and concentrated under reduced pressure to give a residue having the following physical characteristic:

TLC (developing solvent, benzene-ethyl acetate = 2:1):
Rf = 0.58.

To a solution of the crude product in 50 ml. of ethyl acetate were added 10 ml. of a saturated aqueous solution of oxalic acid and the mixture was stirred vigorously at room temperature for one hour. The reaction mixture was extracted with ethyl acetate and the extract was washed with an aqueous solution of sodium bicarbonate and an aqueous solution of sodium chloride, dried over sodium sulphate and concentrated under reduced pressure. The residue was purified by column chromatography on silica gel using a mixture of benzene and ethyl acetate (4:1) as eluent to give 2.472 g. of the title compound and 661 mg. of 1α-acetoxy-2α-(6-methoxycarbonylhex-cis-2-enyl)-3β-acetoxymethyl-4β-(2-tetrahydropyranyloxy)cyclopentane. The title compound showed the following physical characteristics:

TLC (developing solvent, benzene-ethyl acetate = 1:1):
Rf = 0.38, (the diacetate, Rf = 0.54);
IR (liquid film): ν; 3450, 1738, 1433, 1375, 1241, 1155, 1130, 1075, 1030, 995 cm$^{-1}$;
NMR (CDCl$_3$ solution): δ; 5.60–5.10 (3H, m) 4.90–4.25 (2H, m), 4.25–3.35 (4H, m), (3H, s), 2.03 (3H, s).

10.
1α-Acetoxy-2α-(6-methoxycarbonylhexyl)-3β-hydroxymethyl-4β-(2-tetrahydropyranyloxy)cyclopentane 2.45 g. of 1α-acetoxy-2α-(6-methoxycarbonylhex-cis-2-enyl)-3β-hydroxymethyl-4β-(2-tetrahydropyranyloxy)-cyclopentane (prepared as described above) were hydrogenated at a pressure of one atmosphere in 25 ml. of methanol containing 1.0 g. of 5% palladium on charcoal. The reduction was stopped after the absorption of one equivalent of hydrogen gas. The catalyst was filtered off and the filtrate was concentrated under reduced pressure. The residue was purified by column chromatography on silica gel using a mixture of benzene and ethyl acetate (5:1) as eluent to give 1.987 g. of the title compound having the following physical characteristics:

TLC (developing solvent, benzene-ethyl acetate = 1.1):
Rf = 0.42 and 0.38;
IR (liquid film): $\nu$; 3460, 1739, 1438, 1375, 1250, 1135, 1077, 1030 cm$^{-1}$;
NMR (CDCl$_3$ solution): $\delta$; 5.55-5.15 (1H, m), 4.82-4.25 (2H, m), 4.25-3.35 (4H, m), 3.65 (3H, s), 2.03 (3H, s).

11.
1α-Acetoxy-2α-(6-methoxycarbonylhexyl)-3β-formyl-4β-(2-tetrahydropyranyloxy)cyclopentane By proceeding as described in Reference Example 6 but replacing the 1α-acetoxy-2α-(6-methoxycarbonylhex-cis-2-enyl)-3β-hydroxymethyl-4α-(2-tetrahydropyranyloxy)-cyclopentane by 1.07 g. of 1α-acetoxy-2α-(6-methoxycarbonylhexyl)-3β-hydroxymethyl-4β-(2-tetrahydropyranyloxy)-cyclopentane (prepared as described above) dissolved in 25 ml. of methylene chloride and utilizing a solution of 2.69 g. of chromium trioxide and 4.27 ml. of pyridine in 75 ml. of methylene chloride, 14.5 g. of infusorial earth and 14.5 g. of sodium bisulphate, there were obtained 801 mg. of the title compound having the following physical characteristics:

TLC (developing solvent, benzene-ethyl acetate = 1:1):
Rf = 0.59;
IR (liquid film): $\nu$; 1740, 1435, 1372, 1240, 1120, 1075, 1030, 1020 cm$^{-1}$;
NMR (CDCl$_3$ solution): $\delta$; 9.90-9.60 (1H, m), 5.55-5.20 (1H, m), 4.90-4.43 (2H, m), 4.00-3.30 (2H, m), 3.65 (3H, s), 2.03 (3H, s).

REFERENCE EXAMPLE 16
Methyl 9α-acetoxy-11β-(2-tetrahydropyranyloxy)-15α-hydroxy-16ξ-chloroprost-trans-13-enoate By proceeding as described in Example 1 but replacing the methyl 9α,11α-bis(2-tetrahydropyranyloxy)-15-oxo-16ξ-chloroprosta-cis-5,trans-13-dienoate by 628 mg. of methyl 9α-acetoxy-11β-(2-tetrahydropyranyloxy)-15-oxo-16ξ-chloroprost-trans-13-enoate (prepared as described in Reference Example 15) dissolved in 10 ml. of methanol and utilizing 54.3 mg. of sodium borohydride, there were obtained 385 mg. of the title compound and 198 mg. of its 15β-hydroxy isomer. The title compound showed the following physical characteristics:

TLC (developing solvent, benzene-ethyl acetate = 4:1):
Rf = 0.33, (15β-hydroxy isomer, Rf = 0.21);
IR (liquid film): $\nu$; 3450, 1740, 1435, 1375, 1246, 1200, 1130, 1113, 1020, 982 cm$^{-1}$;
NMR (CDCl$_3$ solution): $\delta$; 6.10-5.43 (2H, m), 5.43-5.15 (1H, m), 4.68-4.46 (1H, m), 4.40-3.25 (5H, m), 3.65 (3H, s), 2.02 (3H, s).

REFERENCE EXAMPLE 17
Methyl 9α-acetoxy-11β,15α-bis(2-tetrahydropyranyloxy)-16ξ-chloroprost-trans-13-enoate By proceeding as described in Reference Example 2 but replacing the 15-oxo-PGF$_{2\alpha}$ methyl ester by 385 mg. of methyl 9α-acetoxy-11β-(2-tetrahydropyranyloxy)-15α-hydroxy-16ξ-chloroprost-trans-13-enoate (prepared as described in Reference Example 16) dissolved in 5 ml. of methylene chloride and utilizing 3 mg. of p-toluenesulphonic acid and 0.1 ml. of 2,3-dihydropyran, there were obtained 463 mg. of the crude title compound having the following physical characteristic:

TLC (developing solvent, benzene-ethyl acetate = 4:1):
Rf = 0.39.

EXAMPLE 13
Methyl 9α-hydroxy-11β,15α-bis(2-tetrahydropyranyloxy)-16ξ-chloroprost-trans-13-enoate By proceeding as described in Reference Example 11 but replacing the methyl 9α-acetoxy-11α,15ξ-bis(2-tetrahydropyranyloxy)-16ξ-chloroprosta-cis-5,trans-13-dienoate by 463 mg. of methyl 9α-acetoxy-11β,15α-bis(2-tetrahydropyranyloxy)-16ξ-chloroprost-trans-13-enoate (prepared as described in Reference Example 17) dissolved in 4 ml. of methanol and utilizing 70 mg. of potassium carbonate, there were obtained 362 mg. of the title compound having the following physical characteristics:

TLC (developing solvent, benzene-ethyl acetate = 4:1):
Rf = 0.19;
IR (liquid film): $\nu$; 3460, 1740, 1465, 1450, 1438, 1380, 1375, 1322, 1262, 1243, 1200, 1180, 1130, 1118, 1078, 1033, 1020, 982 cm$^{-1}$;
NMR (CDCl$_3$ solution): $\delta$; 6.20-5.20 (2H, m), 4.85-4.45 (3H, m), 4.45-3.30 (7H, m), 3.65 (3H, s).

EXAMPLE 14
Methyl 9-oxo-11β,15α-bis(2-tetrahydropyranyloxy)-16ξ-chloroprost-trans-13-enoate By proceeding as described in Example 3 but replacing the methyl 9α-hydroxy-11α,15α-bis(trimethylsilyloxy)-16ξ-chloroprosta-cis-5,trans-13-dienoate by 362 mg. of methyl 9α-hydroxy-11β,15α-bis(2-tetrahydropyranyloxy)-16ξ-chloroprost-trans-13-enoate (prepared as described in Example 13) dissolved in 6 ml. of toluene and utilizing a suspension of 505 mg. of N-chlorosuccinimide in 6 ml. of toluene, 0.06 ml. of dimethyl sulphide and 0.6 ml. of triethylamine, there were obtained 360 mg. of the crude title compound having the following physical characteristic:

TLC (developing solvent, benzene-ethyl acetate = 2:1):

Rf = 0.53.

EXAMPLE 15

Methyl 9-oxo-11β,15α-dihydroxy-16ξ-chloroprost-trans-13-enoate [or 16ξ-chloro-11-epi-PGE₁ methyl ester]

By proceeding as described in Example 2 but replacing the methyl 9α,11α-bis(2-tetrahydropyranyloxy)-15ξ-hydroxy-16ξ-chloroprosta-cis-5,trans-13-dienoate by 360 mg. of methyl 9-oxo-11β,15α-bis(2-tetrahydropyranyloxy)-16ξ-chloroprost-trans-13-enoate (prepared as described in Example 14) dissolved in a mixture of 0.6 ml. of tetrahydrofuran and 6 ml. of 65% aqueous acetic acid, there were obtained 160 mg. of the title compound having the following physical characteristics:

TLC (developing solvent, ethyl acetate): Rf = 0.48;
IR (liquid film): ν, 3445, 1740, 1460, 1435, 1375, 1245, 1167, 1047, 980 cm⁻¹;
NMR (CDCl₃ solution): δ; 6.13–5.53 (2H, m), 4.32–4.10 (1H, m), 4.53–4.32 (1H, m), 4.10–3.76 (1H, m), 3.65 (3H, s).

EXAMPLE 16

11α,15α-Bis(2-tetrahydropyranyloxy)-16ξ-chloroprosta-cis-5,trans-13-dien-1,9α-diol Under an atmosphere of nitrogen, 1.84 ml. of a 25(w/v)% solution of diisobutylaluminium hydride in toluene were added dropwise to a solution of 559 mg. of methyl 9α-hydroxy-11α,15α-bis(2-tetrahydropyranyloxy)-16ξ-chloroprosta-cis-5,trans-13-dienoate (prepared as described in Example 7) in 5 ml. of toluene at −78° C. and the mixture was stirred at the same temperature for 30 minutes and then at −10° C. for 1.5 hours. The reaction mixture was quenched with methanol, diluted with 20 ml. of ethyl acetate, washed with 1N hydrochloric acid, an aqueous solution of sodium bicarbonate and an aqueous solution of sodium chloride, dried over sodium sulphate and concentrated under reduced pressure to give 575 mg. of the crude title compound having the following physical characteristics:

TLC (developing solvent, benzene-ethyl acetate = 1:1):
Rf = 0.26;
IR (liquid film): ν; 3420, 1462, 1448, 1437, 1376, 1353, 1260, 1240, 1200, 1130, 1110, 1073, 1032, 1020, 972 cm⁻¹.

EXAMPLE 17

1-Trimethylsilyloxy-11α,15α-bis(2-tetrahydropyranyloxy)-16ξ-chloroprosta-cis-5,trans-13-dien-9α-ol By proceeding as described in Reference Example 5 but replacing the 16ξ-chloro-PGF₂α methyl ester by 575 mg. of 11α,15α-bis(2-tetrahydropyranyloxy)-16ξ-chloroprosta-cis-5,trans-13-dien-1,9α-diol (prepared as described in Example 16) dissolved in 5 ml. of methylene chloride and utilizing 0.21 ml. of N-trimethylsilyldiethylamine, there were obtained 607 mg. of the crude title compound having the following physical characteristic:

TLC (developing solvent, benzene-ethyl acetate = 2:1):
Rf = 0.50.

EXAMPLE 18

1-Trimethylsilyloxy-11α,15α-bis(2-tetrahydropyranyloxy)-16ξ-chloroprosta-cis-5,trans-13-dien-9-one By proceeding as described in Example 3 but replacing the methyl 9α-hydroxy-11α,15α-bis(trimethylsilyloxy)-16ξ-chloroprosta-cis-5,trans-13-dienoate by 607 mg. of 1-trimethylsilyloxy-11α,15α-bis(2-tetrahydropyranyloxy)-16ξ-chloroprosta-cis-5,trans-13-dien-9α-ol (prepared as described in Example 17) dissolved in 10 ml. of toluene and utilizing a suspension of 667.5 mg. of N-chlorosuccinimide in 10 ml. of toluene, 0.1 ml. of dimethyl sulphide and 1 ml. of triethylamine, there were obtained 595 mg. of the crude title compound having the following physical characteristic:

TLC (developing solvent, benzene-ethyl acetate = 2:1):
Rf = 0.49.

EXAMPLE 19

1,11α,15α-Trihydroxy-16ξ-chloroprosta-cis-5,trans-13-dien-9-one [or 16ξ-chloro-PGE₂ alcohol]

By proceeding as described in Example 2 but replacing the methyl 9α,11α-bis(2-tetrahydropyranyloxy)-15ξ-hydroxy-16ξ-chloroprosta-cis-5,trans-13-dienoate by 595 mg. of 1-trimethylsilyloxy-11α,15α-bis(2-tetrahydropyranyloxy)-16ξ-chloroprosta-cis-5,trans-13-dien-9-one (prepared as described in Example 18) dissolved in a mixture of 1 ml. of tetrahydrofuran and 9 ml. of 65% aqueous acetic acid, there were obtained 57 mg. of the title compound having the following physical characteristics:

TLC (developing solvent, ethyl acetate): Rf = 0.25;
IR (liquid film): ν; 3400, 1730, 1420, 1370, 1240, 1155, 1070, 1040, 968 cm⁻¹;
NMR (CDCl₃ solution): δ; 5.83–5.55 (2H, m), 5.55–5.10 (2H, m), 4.40–3.74 (3H, m), 3.74–3.36 (2H, m), 2.75 (1H,dd).

REFERENCE EXAMPLE 18

Methyl 9α-acetoxy-11α-(2-tetrahydropyranyloxy)-15-oxo-16ξ-chloroprost-trans-13-enoate By proceeding as described in Reference Example 12 but replacing the 1α-acetoxy-2α-(6-methoxycarbonylhex-cis-2-enyl)-3β-formyl-4α-(2-tetrahydropyranyloxy)-cyclopentane by 720 mg. of 1α-acetoxy-2α-(6-methoxycarbonylhexyl)-3β-formyl-4α-(2-tetrahydropyranyloxy)-cyclopentane (prepared as described hereafter) dissolved in 4 ml. of tetrahydrofuran and utilizing a suspension of 89.5 mg. of sodium hydride (63% content) in 3 ml. of tetrahydrofuran and a solution of 695 mg. of dimethyl 2-oxo-3-chloroheptylphosphonate (prepared as described in Reference Example 12) in 3 ml. of tetrahydrofuran, there were obtained 783 mg. of the title compound having the following physical characteristics:

TLC (developing solvent, benzene-ethyl acetate = 2:1):
Rf = 0.58;
IR (liquid film): ν; 1740, 1696, 1680, 1627, 1437, 1375, 1223, 1200, 1130, 1078, 1032, 1020, 970 cm⁻¹;
NMR (CDCl₃ solution): δ; 7.14–6.70 (1H, m), 6.68–6.36 (1H, m), 5.26–5.00 (1H, m), 4.66–4.43

(1H, m), 4.43–4.22 (1H, m), 4.22–3.24 (3H, m), 3.66 (3H, s), 2.29 (2H, t), 2.06 (3H, s).

1α-Acetoxy-2α-(6-methoxycarbonylhexyl)-3β-formyl-4α-(2-tetrahydropyranyloxy)-cyclopentane, used as a starting material in the above procedure, was prepared from 1α-acetoxy-2α-(6-methoxycarbonylhex-cis-2-enyl)-3β-formyl-4α-(2-tetrahydropyranyloxy)cyclopentane (prepared as described in Reference Example 6) as follows:

1.15 g. of 1α-acetoxy-2α-(6-methoxycarbonylhex-cis-2-enyl)-3β-formyl-4α-(2-tetrahydropyranyloxy)cyclopentane were hydrogenated at a pressure of one atmosphere in 30 ml. of methanol containing 290 mg. of 5% palladium on charcoal. The reduction was stopped after the absorption of one equivalent of hydrogen gas. The catalyst was filtered off and the filtrate was concentrated under reduced pressure to give 1.12 g. of 1α-acetoxy-2α-(6-methoxycarbonylhexyl)-3β-formyl-4α-(2-tetrahydropyranyloxy)-cyclopentane having the following physical characteristics:

TLC (developing solvent, benzene-ethyl acetate = 2:1):

Rf = 0.49;

IR (liquid film): ν; 2970, 2880, 2730, 1740, 1430, 1370, 1240, 1125, 1015, 960 cm$^{-1}$;

NMR (CDCl$_3$ solution): δ; 9.75 (1H, t), 5.3–4.9 (1H, m), 4.8–4.1 (1H, m), 3.65 (3H, s), 2.06 (3H, s).

REFERENCE EXAMPLE 19

Methyl 9α-acetoxy-11α-(2-tetrahydropyranyloxy-15ξ-hydroxy-15-methyl-16ξ-chloroprost-trans-13-enoate.

Under an atmosphere of nitrogen, 2.5 ml. of a 0.9M solution of metyllithium in diethyl ether were added dropwise to a solution of 768 mg. of methyl 9α-acetoxy-11α-(2-tetrahydropyranyloxy)-15-oxo-16ξ-chloroprost-trans-13-enoate (prepared as described in Reference Examples 18) in 10 ml. of tetrahydrofuran at −78° C. and the mixture was stirred at the same temperature or 1 hour. The reaction mixture was quenched with acetic acid and poured into 20 ml. of water. The solution was extracted with ethyl acetate and the extract was washed with a saturated aqueous solution of sodium bicarbonate and an aqueous solution of sodium chloride, dried over sodium sulphate and concentrated under reduced pressure. The residue was purified by column chromatography on silica gel using a mixture of benzene and ethyl acetate (9:1) as eluent to give 296 mg. of the title compound having the following physical characteristics:-

TLC (developing solvent, benzene-ethyl acetate = 2:1):

Rf = 0.39;

IR (liquid film): ν; 3460, 1740, 1438, 1377, 1249, 1200, 1133, 1079, 1030, 1021, 975 cm$^{-1}$;

NMR (CDCl$_3$ solution): δ; 5.78–5.56 (2H, m), 5.22–5.00 (1H, m), 4.71–4.52 (1H, m), 4.30–3.20 (4H, m), 3.66 (3H, s), 2.29 (2H, m), 2.05 (3H, s), 1.42–1.24 (3H, m).

REFERENCE EXAMPLE 20

Methyl 9α-acetoxy-11α, 15ξ-bis(2-tetrahydropyranyloxy)-15-methyl-16ξ-chloroprost-trans-13-enoate By proceeding as described in Reference Examples 2 but replacing the 15-oxo-PGF$_{2α}$methyl ester by 283 mg. of methyl 9α-acetoxy-11α-(2-tetrahydropyranyloxy)-15ξ-hydroxy-15-methyl-16ξ-chloroprost-trans-13-enoate (prepared as described in Reference Example 19) dissolved in 5 ml. of methylene chloride and utilized a catalytic amount of p-toluenesulphonic acid and 0.2 ml. of 2,3-dihydropyran, there were obtained 296 mg. of the title compound having the following physical characteristics:- TLC (developing solvent, benzene-ethyl acetate = 2:1):

Rf = 0.55;

IR (liquid film): ν; 1740, 1436, 1373, 1242, 1200, 1120, 1033, 1020, 979 cm$^{-1}$.

EXAMPLE 20

Methyl 9α-hydroxy-11α,15ξ-bis(2-tetrahydropyranyloxy)-15-methyl-16ξ-chloroprost-trans-13-enoate By proceeding as described in Reference Example 11 but replacing the methyl 9α-acetoxy-11α, 15ξ-bis(2-tetrahydropyranyloxy)-16ξ-chloroprosta-cis-5,trans-13-dienoate by 296 mg. of methyl 9α-acetoxy-11α, 15ξ-bis(2-tetrahydropyranyloxy)-15-methyl-16ξ-chloroprost-trans-13-enoate (prepared as described in Reference Example 20) dissolved in 5 ml. of methanol and utilizing 120 mg. of potassium carbonate, there were obtained 204 mg. of the title compound having the following physical characteristics:-

TLC (developing solvent, benzene-ethyl acetate = 2:1):

Rf = 0.35;

IR (liquid film): ν; 3460, 1740, 1439, 1380, 1260, 1242, 1200, 1120, 1075, 1031, 1021, 980 cm$^{-1}$;

NMR (CDCl$_3$ solution): δ; 5.78–5.42 (2H, m), 4.90–4.55 (2H, m), 4.35–3.20 (7H, m), 3.66 (3H, s), 1.52–1.33 (3H, m).

EXAMPLE 21

Methyl 9-oxo-11α, 15ξ-bis(2-tetrahydropyranyloxy)-15-methyl-16ξ-chloroprost-trans-13-enoate By proceeding as described in Example 3 but replacing the methyl 9α-hydroxy-11α, 15α-bis-(trimethylsilyloxy)-16ξ-chloroprosta-cis-5,trans-13-dienoate by 204 mg. of methyl 9α-hydroxy-11α,15ξ-bis(2-tetrahydropyranyloxy)-15-metyl-16ξ-chloroprost-trans-13-enoate (prepared as described in Example 20) dissolved in 4 ml. of toluene and utilizing a suspension of 280 mg. of N-chlorosuccinimide in 4 ml. of toluene, 0.04 ml. of dimethyl sulphide and 0.4 ml. of triethylamine, there were obtained 230 mg. of the crude title compound having the following physical characteristic:-

TLC (developing solvent, benzene-ethyl acetate = 2:1):

Rf = 0.55.

EXAMPLE 22

Methyl 9-oxo-11α,15ξ-dihydroxy-15-methyl-16ξ-chloroprost-trans-13-enoate [or 15ξ-methyl-16ξ-chloro-PGE$_1$ methyl ester]

By proceeding as described in Example 2 but replacing the methyl 9α,11α-bis(2-tetrahydropyranyloxy)-15ξ-hydroxy-16ξ-chloroprosta-cis-5,trans-13-dienoate by 230 mg. of methyl 9-oxo-11α,15ξ-bis(2-tetrahydropyranyloxy)-15-methyl-16ξ-chloroprost-trans-13-enoate (prepared as described in Example 21) dissolved in a mixture of 0.5 ml. of tetrahydrofuran and 4 ml. of 65% aqueous acetic acid, there were obtained 100 mg.

of the title compound having the following physical characteristics:-
- TLC (developing solvent, ethyl acetate): Rf = 0.48;
- IR (liquid film): ν; 3420, 1740, 1435, 1372, 1243, 1163, 1073, 975 cm$^{-1}$;
- NMR (CDCl$_3$ solution): δ; 5.85–5.64 (2H, m), 4.25–3.70 (2H, m), 3.65 (3H, s), 2.75 (1H, dd), 1.39 (3H, s).

REFERENCE EXAMPLE 21

Methyl 9α-acetoxy-11α-(2-tetrahydropyranyloxy)-15-oxo-16ξ-chloro-16-methylprost-trans-13-enoate By proceeding as described in Reference Example 18 but replacing the dimethyl 2-oxo-3-chloroheptylphosphonate by 376 mg. of dimethyl 2-oxo-3-chloro-3-methylheptylphosphonate (prepared as described hereafter) dissolved in 2 ml. of tetrahydrofuran and utilizing a suspension of 45.7 mg. of sodium hydride (63% content) in 3 ml. of tetrahydrofuran and a solution of 394 mg. of 1α-acetoxy-2α-(6-methoxycarbonylhexyl)-3β-formyl-4α-(2-tetrahydropyranyloxy)cyclopentane (prepared as described in Reference Example 18) in 5 ml. of tetrahydrofuran, there were obtained 431 mg. of the title compound having the following physical characteristics:-
- TLC (developing solvent, benzene-ethyl acetate = 2:1):
- Rf = 0.59;
- IR (liquid film): ν; 1739, 1696, 1624, 1437, 1376, 1222, 1200, 1130, 1074, 1031, 1020, 970 cm$^{-1}$;
- NMR (CDCl$_3$ solution): δ; 7.2–6.72 (2H, m), 5.26–5.00 (1H, m), 4.68–4.42 (1H, m), 4.30–3.26 (3H, m), 3.66 (3H, s), 2.06 (3H, s), 1.66 (3H, s).

Dimethyl 2-oxo-3-chloro-3-methylheptylphosphonate, used as a starting material, was prepared from dimethyl 2-oxo-3-methylheptylphosphonate (described in British Pat. Specification No. 1398291) as follows:

Under an atmosphere of nitrogen, a solution of 9.44 g. of dimethyl 2-oxo-3-methylheptylphosphonate in 20 ml. of tetrahydrofuran was added dropwise to a suspension of 1.68 g. of sodium hydride (63% content) in 80 ml. of tetrahydrofuran at room temperature and the mixture stirred at room temperature for 30 minutes. After cooling the solution to 0° C., there was added dropwise 36 ml. of a 1.4M solution of n-butyllithium in n-hexane and the mixture was stirred at that temperature for 45 minutes. After cooling the resulting solution to −78° C., there was added dropwise a solution of 8.83 g. of benzenesulphonyl chloride in 20 ml. of tetrahydrofuran and the mixture was stirred at −78° C. for 30 minutes, then at 0° C. for 30 minutes and at room temperature for 30 minutes. The reaction mixture was then acidified to pH 3 with acetic acid, diluted with 50 ml. of chloroform, washed with water and an aqueous solution of sodium chloride, dried over sodium sulphate an concentrated under reduced pressure. The residue was purified by column chromatography on silica gel using a mixture of benzene and ethyl acetate (1:2) as eluent to give 3.18 g. of dimethyl 2-oxo-3-chloro-3-methylheptylphosphonate having the following physical characteristics:-
- TLC (developing solvent, ethyl acetate): Rf = 0.41;
- IR (liquid film): ν; 1715, 1450, 1374, 1258, 1183, 1032, 870, 860, 808 cm$^{-1}$;
- NMR (CDCl$_3$ solution): δ; 3.73 (6H, d), 3.39 (2H, d), 1.63 (3H, s).

REFERENCE EXAMPLE 22

Methyl 9α-acetoxy-11α-(2-tetrahydropyrayloxy)-15α-hydroxy-16ξ-chloro-16-methylprost-trans-13-enoate By proceeding as described in Example 1 but replacing the methyl 9α,11α-bis(2-tetrahydropyranyloxy)-15-oxo-16ξ-chloroprosta-cis-5,trans-13-dienoate by 469 mg. of methyl 9α-acetoxy-11α-(2-tetrahydropyranyloxy)-15-oxo-16ξ-chloro-16-chloro-16-methylprost-trans-13-enoate (prepared as described in Reference Example 21) dissolved in 7 ml. of methanol and utilizing 39.5 mg. of sodium borohydride, there were obtained 322 mg. of the title compound and 84 mg. of its 15β-hydroxy isomer. The title compound showed the following physical characteristics:-
- TLC (developing solvent, benzene-ethyl acetate = 2:1):
- Rf = 0.38, (15β-hydroxy isomer, Rf = 0.46);
- IR (liquid film): ν; 3450, 1740, 1438, 1375, 1244, 1200, 1172, 1075, 1020, 971 cm$^{-1}$;
- NMR (CDCl$_3$solution): δ; 5.82–5.52 (2H, m), 5.26–4.95 (1H, m), 4.72–4.48 (1H, m), 4.28–3.26 (4H, m), 3.66 (3H, s), 2.06 (3H, s), 1.64–1.47 (3H, m).

REFERENCE EXAMPLE 23

Methyl 9α-acetoxy-11α,15α-bis(2-tetrahydropyranyloxy)-16ξ-chloro-16-methylprost-trans-13-enoate By proceeding as described in Reference Example 2 but replacing the 15-oxo-PGF$_{2α}$methyl ester by 304 mg. of methyl 9α-acetoxy-11α-(2-tetrahydropyranyloxy)-15α-hydroxy-16ξ-chloro-16-methylprost-trans-13-enoate (prepared as described in Example 22) dissolved in 5 ml. of methylene chloride and utilizing a catalytic amount of p-toluenesulphonic acid and 0.1 ml. of 2,3-dihydropyran, there were obtained 390 mg. of the crude title compound having the following physical characteristics:-
- TLC (developing solvent, benzene-ethyl acetate =2:1):
- Rf = 0.54;
- IR (liquid film):ν; 1740, 1438, 1373, 1350, 1221, 1130, 1118, 1078, 1035, 1020, 972 cm$^{-1}$.

EXAMPLE 23

Methyl 9α-hydroxy-11α,15α-bis(2-tetrahydropyranyloxy)-16ξ-chloro-16-methylprost-trans-13-enoate By proceeding as described in Reference Example 11 but replacing the methyl 9α-acetoxy-11α,15ξ-bis(2-tetrahydropyranyloxy)-16ξ-chloroprosta-cis-5,trans-13-dienoate by 390 mg. of methyl 9α-acetoxy-11α,15α-bis(2-tetrahydropyranyloxy)-16ξ-chloro-16-methyl-prost-trans-13-enoate (prepared as described in Reference Example 23) dissolved in 5 ml. of methanol and utilizing 67 mg. of potassium carbonate, there were obtained 302 mg. of the title compound having the following physical characteristics:-
- TLC (developing solvent, benzene-ethyl acetate = 2:1):
- Rf = 0.34;
- IR (liquid film):ν; 3470, 1740, 1438, 1376, 1260, 1200, 1130, 1117, 1077, 1020, 975 cm$^{-1}$;

NMR (CDCl₃ solution): δ; 5.70–5.35 (2H, m), 4.95–4.52 (2H, m), 4.32–3.20 (7H, m), 3.66 (3H, s).

EXAMPLE 24

Methyl 9-oxo-11α,15α-bis(2-tetrahydropyranyloxy)-16ξ-chloro-16-methylprost-trans-13-enoate By proceeding as described in Example 3 but replacing the methyl 9α-hydroxy-11α,15α-bis(trimethylsilyloxy)-16ξ-chloroprosta-cis-5,trans-13-dienoate by 291 mg. of methyl 9α-hydroxy-11α,15α-bis(2-tetrahydropyranyloxy)-16ξ-chloro-16-methylprost-trans-13-enoate (prepared as described in Example 23) dissolved in 5 ml. of toluene and utilizing a suspension of 398 mg. of N-chlorosuccinimide in 5 ml. of toluene, 0.05 ml. of dimethyl sulphide and 0.5 ml. of triethylamine, there were obtained 310' mg. of the crude title compound having the following physical characteristic:-

TLC (developing solvent, benzene-ethyl acetate = 2:1):
Rf = 0.51.

EXAMPLE 25

Methyl 9-oxo-11α,15α-dihydroxy-16ξ-chloro-16-methylprost-trans-13-enoate [or 16ξ-chloro-16-methyl-PGE₁ methyl ester]

By proceeding as described in Example 2 but replacing the methyl 9α,11α-bis(2-tetrahydropyranyloxy)-15ξ-hydroxy-16ξ-chloroprosta-cis-5,trans-13-dienoate by 310 mg. of methyl 9-oxo-11α,15α-bis(2-tetrahydropyranyloxy)-16ξ-chloro-16-methylprost-trans-13-enoate (prepared as described in Example 24) dissolved in a mixture of 1 ml. of tetrahydrofuran and 5 ml. of 65% aqueous acetic acid, there were obtained 117 mg. of the title compound having the following physical characteristics:

TLC (developing solvent, ethyl acetate): Rf = 0.47;
IR (liquid film): ν; 3415, 1740, 1435, 1377, 1243, 1161, 1075, 975 cm⁻¹;
NMR (CDCl₃ solution): δ; 5.92–5.60 (2H, m), 4.32–3.76 (2H, m), 3.65 (3H, s), 2.75 (1H, dd), 1.57–1.46 (3H, m).

REFERENCE EXAMPLE 24

Methyl 9α-acetoxy-11α-(2-tetrahydropyranyloxy)-15-oxo-16ξ-chloroprosta-trans-2,trans-13-dienoate By proceeding as described in Reference Example 12 but replacing the 1α-acetoxy-2α-(6-methoxycarbonylhex-cis-3-enyl)-3β-formyl-4α-(2-tetrahydropyranyloxy)-cyclopentane by 500 mg. of 1α-acetoxy-2α-(6-methoxycarbonylhex-trans-5-enyl)-3β-formyl-4α-(2-tetrahydropyranyloxy)cyclopentane (prepared as described hereafter) dissolved in 3 ml. of tetrahydrofuran and utilizing a suspension of 62.6 mg. of sodium hydride (63% content) in 5 ml of tetrahydrofuran and a solution of 486 mg. of dimethyl 2-oxo-3-chloroheptylphosphonate (prepared as described in Reference Example 12) in 2 ml. of tetrahydrofuran, there were obtained 575 mg. of the title compound having the following physical characteristics:

TLC (developing solvent, benzene-ethyl acetate = 2:1):
Rf = 0.56;
IR (liquid film): ν; 1740, 1700, 1660, 1628, 1435, 1376, 1244, 1137, 1080, 1038, 1022, 980 cm⁻¹;
NMR (CDCl₃ solution): δ; 7.4–6.75 (2H, m), 6.57 (1H, dd), 5.81 (1H, d), 5.35–5.04 (1H, m), 4.75–3.25 (5H, m), 3.74 (3H, s), 2.05 (3H, s).

1α-Acetoxy-2α-(6-methoxycarbonylhex-trans-5-enyl)-3β-formyl-4α-(2-tetrahydropyranyloxy)cyclopentane, used as a starting material in the above procedure, was prepared from 2α-(6-methoxycarbonylhex-cis-2-enyl)-3β-hydroxymethyl-4α-(2-tetrahydropyranyloxy)cyclopentan-1α-ol (prepared as described in Reference Example 6) as follows:

1. 2α-(6-methoxycarbonylhexyl)-3β-hydroxymethyl-4α-(2-tetrahydropyranyloxy)cyclopentan-1α-ol 14.2 g. of 2α-(6-methoxycarbonylhex-cis-2-enyl)-3β-hydroxymethyl-4α-(2-tetrahydropyranyloxy)cyclopentan-1α-ol (prepared as described in Reference Example 6) was hydrogenated at a pressure of one atmosphere in 300 ml. of methanol containing 3 g. of 5% palladium on charcoal. The reduction was stopped after the absorption of one equivalent of hydrogen gas. The catalyst was removed by filtration and the filtrate was concentrated under reduced pressure to give 13.8 g. of the title compound having the following physical characteristics:

TLC (developing solvent, benzene-ethyl acetate = 1:1):
Rf = 0.28;
IR (liquid film): ν; 3450, 1740, 1440, 1030 cm⁻¹;
NMR (CDCl₃ solution): δ; 5.00–4.55 (1H, m), 3.70 (3H, s).

2. 2α-Phenylseleno-6-methoxycarbonylhexyl)-3β-hydroxymethyl-4α-(2-tetrahydropyranyloxy)cyclopentan-1α-ol Under an atmosphere of nitrogen, a solution of 19.4 ml. of diisopropylamine in 350 ml. of tetrahydrofuran was cooled to −78° C., and to it was added dropwise 114 ml. of a 1.2M solution of n-butyllithium in n-hexane and the mixture was stirred at −78° C. for 20 minutes to give lithium diisopropylamide. To the lithium diisopropylamide solution was added dropwise a solution of 13.8 g. of 2α-(6-methoxycarbonylhexyl)-3β-hydroxymethyl-4α-(2-tetrahydropyranyloxy)cyclopentan-1α-ol [prepared as described in (1) above] in 100 ml. of tetrahydrofuran at −78° C. and the mixture was stirred at the same temperature for 30 minutes. A solution of 18.2 g. of diphenyldiselenide in 50 ml. of tetrahydrofuran was added dropwise to the reaction mixture at −78° C. and the solution was stirred at the same temperature for one hour and then at 0° C. for 20 minutes. The reaction mixture was poured into an aqueous solution of ammonium chloride and extracted with ethyl acetate. The extract was washed with water and an aqueous solution of sodium chloride, dried over magnesium sulphate and concentrated under reduced pressure. The residue was purified by column chromatography on silica gel using a mixture of benzene and ethyl acetate (3:2) as eluent to give 15.8 g. of the title compound having the following physical characteristics:

TLC (developing solvent, benzene-ethyl acetate = 1:1):
Rf = 0.37;
IR (liquid film): ν; 3450, 1740, 1580, 1440, 1030 cm⁻¹;

NMR (CDCl₃ solution): δ; 7.75–7.10 (5H, m), 5.00–4.55 (1H, m), 3.70 (3H, s).

3.
2α-(6-Methoxycarbonylhex-trans-5-enyl)-3β-hydroxymethyl-4α-(2-tetrahydropyranyloxy)cyclopentan-1α-ol To a solution of 15.8 g. of 2α-(6-phenylseleno-6-methoxycarbonylhexyl)-3β-hydroxymethyl-4α-(2-tetrahydropyranyloxy)cyclopentan-1α-ol [prepared as described in (2) above] in a mixture of 200 ml. of ethyl acetate and 100 ml. of tetrahydrofuran, there were added 4.5 g. of sodium carbonate and 6.2 ml. of 30% hydrogen peroxide and the mixture was stirred at 30° C for 30 minutes. The reaction mixture was then poured into water, washed with an aqueous solution of sodium carbonate, water and an aqueous solution of sodium chloride, dried over magnesium sulphate and concentrated under reduced pressure to give 10.4 g. of the title compound having the following physical characteristics:

TLC (developing solvent, benzene-ethyl acetate = 1:1):
Rf = 0.28;
IR (liquid film): ν; 3450, 1735, 1660, 1440, 1030 cm⁻¹;
NMR (CDCl₃ solution): δ; 6.90 (1H, dt), 5.82 (1H, d), 5.00–4.55 (1H, m), 3.70 (3H, s).

4.
1α-Acetoxy-2α-(6-methoxycarbonylhex-trans-5-enyl)-3β-hydroxymethyl-4α-(2-tetrahydropyranyloxy)cyclopentane Under an atmosphere of nitrogen, a solution of 4.3 ml. of trimethylchlorosilane in 20 ml. of methylene chloride was added dropwise to a solution of 10.4 g. of 2α-(6-methoxycarbonylhex-trans-5-enyl)-3β-hydroxymethyl-4α-(2-tetrahydropyranyloxy)cyclopentan-1α-ol [prepared as described in (3) above] in a mixture of 150 ml. of methylene chloride and 18.8 ml. of pyridine at −20° C., and the mixture was stirred at the same temperature for 20 minutes. To the solution thus obtained was added dropwise a solution of 2.45 ml. of acetyl chloride in 50 ml. of methylene chloride at −20° C. and the mixture was stirred at room temperature for 30 minutes. Then 3 ml. of ethanol was added to the reaction mixture in order to decompose the excess of acetyl chloride. Pyridine in the solution was quenched with 80 g. of sodium bisulphate, and the resulting precipitate was filtered off. The filtrate was concentrated under reduced pressure. The residue was dissolved in 300 ml. of ethyl acetate, 100 ml. of a saturated aqueous solution of oxalic acid was added and the mixture was stirred vigorously at room temperature for 30 minutes. The reaction mixture was then extracted with ethyl acetate, the extract was washed with water, an aqueous solution of sodium bisulphate, water and an aqueous solution of sodium chloride, dried over magnesium sulphate and concentrated under reduced pressure. The residue was purified by column chromatography on silica gel using a mixture of benzene and ethyl acetate (3:1) as eluent to give 7.2 g. of the title compound having the following physical characteristics:

TLC (developing solvent, benzene-ethyl acetate = 1:1):
Rf = 0.51;
IR (liquid film): ν; 3450, 1735, 1660, 1440, 1030 cm⁻¹;
NMR (CDCl₃ solution): δ; 6.90 (1H, dt), 5.82 (1H, d), 5.25–4.90 (1H, m), 4.85–4.45 (1H, m), 3.71 (3H, s), 2.05 (3H, s).

5.
1α-Acetoxy-2α-(6-methoxycarbonylhex-trans-5-enyl)-3β-formyl-4α-(2-tetrahydropyranyloxy)cyclopentane Under an atmosphere of nitrogen, 34 ml. of pyridine were dissolved in 440 ml. of methylene chloride, 20.2 g. of chromium trioxide were added with stirring and the mixture was then stirred at room temperature for 15 minutes. To the reaction mixture was added 88 g. of infusorial earth and the solution was cooled to 0° C. To it was added a solution of 7.2 g. of 1α-acetoxy-2α-(6-methoxycarbonylhex-trans-5-enyl)-3β-hydroxymethyl-4α-(2-tetrahydropyranyloxy)cyclopentane [prepared as described in (4) above] in 100 ml. of methylene chloride at 0° C. After 10 minutes of stirring at 0° C., 155 g. of sodium bisulphate were added to the reaction mixture and stirring was continued for a further 10 minutes. The resulting precipitate was filtered through a pad of magnesium sulphate and the filtrate was concentrated under reduced pressure. The residue was purified by column chromatography on silica gel using a mixture of benzene and ethyl acetate (5:1) as eluent to give 5.85 g. of the title compound having the following physical characteristics:

TLC (developing solvent, benzene-ethyl acetate = 2:1):
Rf = 0.67;
IR (liquid film): ν; 1735, 1660, 1440, 1250, 1030 cm⁻¹;
NMR (CDCl₃ solution): δ; 10.00–9.70 (1H, m), 6.90 (1H, dt), 5.82 (1H, d), 5.30–4.96 (1H, m), 4.75–4.10 (2H, m), 3.72 (3H, s), 2.06 (3H, s).

REFERENCE EXAMPLE 25

Methyl 9α-acetoxy-11α-(2-tetrahydropyranyloxy)-15ξ-hydroxy-16ξ-chloroprosta-trans-2,trans-13-dienoate By proceeding as described in Example 1 but replacing the methyl 9α,11α-bis(2-tetrahydropyranyloxy)-15-oxo-16ξ-chloroprosta-cis-5,trans-13-dienoate by 570 mg. of methyl 9α-acetoxy-11α-(2-tetrahydropyranyloxy)-15-oxo-16ξ-chloroprosta-trans-2-trans,-13-dienoate (prepared as described in Reference Example 24) dissolved in 8 ml. of methanol and utilizing 49.4 mg. of sodium borohydride, there were obtained 623 mg. of the title compound having the following physical characteristics:

TLC (developing solvent, benzene-ethyl acetate = 2:1):
Rf = 0.35 and 0.40;
IR (liquid film): ν; 3450, 1738, 1654, 1434, 1242, 1132, 1035, 1020, 974 cm⁻¹;
NMR (CDCl₃ solution): δ; 7.18–6.70 (1H, m), 5.94–5.45 (3H, m), 5.22–4.96 (1H, s), 4.74–4.42 (1H, m), 4.30–3.30 (5H, m), 3.72 (3H, s), 2.66 (3H, s).

REFERENCE EXAMPLE 26

Methyl 9α-acetoxy-11α,15ξ-bis(2-tetrahydropyranyloxy)-16ξ-chloroprosta-trans-2,trans-13-dienoate By proceeding as described in Reference Example 2 but replacing the 15-oxo-PGF$_{2\alpha}$ methyl ester by 610 mg. of methyl 9α-acetoxy-11α-(2-tetrahydropyranyloxy)-15ξ-hydroxy-16ξ-chloroprosta-trans-2,trans-13-dienoate (prepared as described in Reference Example 25)

dissolved in 10 ml. of methylene chloride and utilizing a catalytic amount of p-toluenesulphonic acid and 0.3 ml. of 2,3-dihydropyran, there were obtained 730 mg. of the crude title compound having the following physical characteristics:

TLC (developing solvent, benzene-ethyl acetate = 2:1):
Rf = 0.51;
IR (liquid film): $\nu$; 1735, 1658, 1437, 1380, 1245, 1200, 1130, 1120, 1080, 1040, 1023, 978 cm$^{-1}$.

EXAMPLE 26

Methyl 9α-hydroxy-11α,15ξ-bis(2-tetrahydropyranyloxy)-16ξ-chloroprosta-trans-2,trans-13-dienoate By proceeding as described in Reference Example 11 but replacing the methyl 9α-acetoxy-11α,15ξ-bis(2-tetrahydropyranyloxy)-16ξ-chloroprosta-cis-5,trans-13-dienoate by 730 mg. of methyl 9α-acetoxy-11α,15ξ-bis(2-tetrahydropyranyloxy)-16ξ-chloroprosta-trans-2,trans-13-dienoate (prepared as described in Reference Example 26) dissolved in 12 ml. of methanol and utilizing 228 mg. of potassium carbonate, there were obtained 552 mg. of the title compound having the following physical characteristics:

TLC (developing solvent, benzene-ethyl acetate = 2:1):
Rf = 0.30;
IR (liquid film): $\nu$; 3450, 1730, 1658, 1435, 1273, 1242, 1200, 1132, 1117, 1080, 1036, 1022, 978 cm$^{-1}$;
NMR (CDCl$_3$ solution): $\delta$; 7.18–6.70 (1H, m), 5.96–5.38 (3H, m), 4.92–4.50 (2H, m), 4.34–3.30 (8H, m), 3.72 (3H, s).

EXAMPLE 27

Methyl 9-oxo-11α,15ξ-bis(2-tetrahydropyranyloxy)-16ξ-chloroprosta-trans-2,trans-13-dienoate By proceeding as described in Example 3 but replacing the methyl 9α-hydroxy-11α,15α-bis(trimethylsilyloxy)-16ξ-chloroprosta-cis-5,trans-13-dienoate by 536 mg. of methyl 9α-hydroxy-11α,15ξ-bis(2-tetrahydropyranyloxy)-16ξ-chloroprosta-trans-2,trans-13-dienoate (prepared as described in Example 26) dissolved in 10 ml. of toluene and utilizing a suspension of 703 mg. of N-chlorosuccinimide in 10 ml. of toluene, 0.5 ml. of dimethyl sulphide and 1.75 ml. of triethylamine, there were obtained 422 mg. of the title compound having the following physical characteristics:

TLC (developing solvent, benzene-ethyl acetate = 2:1):
Rf = 0.48;
IR (liquid film): $\nu$; 1741, 1725, 1655, 1435, 1273, 1241, 1200, 1120, 1075, 1034, 1020, 972 cm$^{-1}$;

EXAMPLE 28

Methyl 9-oxo-11α,15α-dihydroxy-16ξ-chloroprosta-trans-2,trans-13-dienoate [or 16ξ-chloro-trans-$\Delta^2$-PGE$_1$ methyl ester]

By proceeding as described in Example 2 but replacing the methyl 9α,11α-bis(2-tetrahydropyranyloxy)-15ξ-hydroxy-16ξ-chloroprosta-cis-5,trans-13-dienoate by 422 mg. of methyl 9-oxo-11α,15ξ-bis(2-tetrahydropyranyloxy)-16ξ-chloroprosta-trans-2,trans-13-dienoate (prepared as described in Example 27) dissolved in a mixture of 1 ml. of tetrahydrofuran and 7 ml. of 65% aqueous acetic acid, there were obtained 94 mg. of the title compound and 68 mg. of its 15β-hydroxy isomer. The title compound showed the following physical characteristics:

TLC (developing solvent, ethyl acetate): Rf = 0.35, (15β-hydroxy isomer, Rf = 0.45);
IR (liquid film): $\nu$; 3410, 1743, 1727, 1656, 1435, 1275, 1200, 1177, 1158, 1074, 1040, 974 cm$^{-1}$;
NMR (CDCl$_3$ solution)- $\delta$; 6.92 (1H, dt), 5.95–5.53 (3H, m), 4.34–3.57 (3H, m), 3.71 (3H, s), 2.75 (1H, dd).

REFERENCE EXAMPLE 27

Methyl 9α-acetoxy-11α,20-bis(2-tetrahydropyranyloxy)-15-oxo-16ξ-chloroprost-trans-13-enoate By proceeding as described in Reference Example 15 but replacing the dimethyl 2-oxo-3-chloroheptylphosphonate by 2.83 g. of dimethyl 2-oxo-3-chloro-7-(2-tetrahydropyranyloxy)heptylphosphonate (prepared as described hereafter) dissolved in 10 ml. of tetrahydrofuran and utilizing a suspension of 258 mg. of sodium hydride (63% content) in 5 ml. of tetrahydrofuran and a solution of 2.25 g. of 1α-acetoxy-2α-(6-methoxycarbonylhexyl)-3β-formyl-4α-(2-tetrahydropyranyloxy)-cyclopentane (prepared as described in Reference Example 15) in 10 ml. of tetrahydrofuran, there were obtained 2.99 g. of the title compound having the following physical characteristics:-

TLC (developing solvent, benzene-ethyl acetate = 2:1):
Rf = 0.27;
IR (liquid film):$\nu$; 1738, 1694, 1625, 1437, 1373, 1355, 1322, 1240, 1198, 1131, 1118, 1075, 1031, 1020, 970 cm$^{-1}$;
NMR (CDCl$_3$ solution): $\delta$;7.16–6.74 (1H, m), 6.54 (1H, dd), 5.25–5.01 (1H, m), 4.70–4.45 (2H, m), 4.45–4.25 (1H, m), 4.25–3.24 (7H, m), 3.66 (3H, s), 2.07 (3H, s).

Dimethyl 2-oxo-3-chloro-7-(2-tetrahydropyranyloxy)-heptylphosphonate, used as a starting material in the above procedure, was prepared from ethyl 6-hydroxyhexanote [prepared as described by S. R. Sandler and W. Karo, in 'Organic Functional Group Preparation', Academic Press, New York and London, Vol. 1, page 262. -cf. G. B. Hatch and H. Adkins, J. Amer. Chem. Soc., 59, 1694 (1937)] as follows.

1. Ethyl 6-(2-tetrahydropyranyloxy)hexanoate

To a solution of 66 g. of ethyl 6-hydroxyhexanoate in 400 ml. of methylene chloride were added 1 g. of p-toluenesulphonic acid and 45 g. of 2,3-dihydropyran and the mixture was stirred at 25° C. for 20 minutes. The reaction mixture was then washed with an aqueous solution of sodium bicarbonate, dried and concentrated. The residue was distilled in vacuo to obtain 77 g. of the title compound having the following physical characteristics:- b.p. 135° C./3 mm.Hg;
IR (liquid film): $\nu$; 2940, 2860, 1740, 1445, 1370, 1350, 1325, 1260, 1160, 1140, 1120, 1080, 1040, 985, 910, 870, 820 cm$^{-1}$;
NMR (CDCl$_3$ solution): $\delta$; 4.70–4.35 (1H, m), 4.05 (2H, q), 4.00–3.00 (4H, m), 2.24 (2H, t), 1.20 (3H, t).

2. Dimethyl 2-oxo-7-(2-tetrahydropyranyloxy)heptylphosphonate 45 g. of dimethyl methylphosphonate were dissolved in 400 ml. of absolute tetrahydrofuran and 180 ml. of a 2M solution of n-butyllithium in diethyl ether were added dropwise whilst maintaining the temperature below −50° C. Ten minutes later, 37 g. of ethyl 6-(2-tetrahydropyranyloxy)-hexanoate (prepared as described above) in 100 ml. of absolute tetrahydrofuran were added dropwise to the solution, and the reaction mixture stirred at the same temperature for 3 hours and then at 0° C. for 16 hours. The reaction mixture was acidified with acetic acid and concentrated under reduced pressure. The residue was dissolved in a small amount of water and extracted with diethyl ether. The extract was dried over magnesium sulphate and concentrated under reduced pressure. The residue was distilled at 140° C. (oil bath temperature) at a pressure of 0.2 mm.Hg. The residue was 31 g. of the title compound, the boiling point of which was too high to permit distillation and which had the following physical characteristics:-

IR (liquid film): ν; 2950, 2870, 1720, 1455, 1410, 1375, 1365, 1335, 1275, 1200, 1190, 1140, 1120, 1110–990, 920, 880, 820 cm$^{-1}$;

NMR (CDCl$_3$ solution): δ; 4.75–4.30 (1H, m), 4.15–3.10 (4H, m), 3.75 (6H, d), 3.06 (2H, d), 2.58 (2H, t).

3. Dimethyl 2-oxo-3-chloro-7-(2-tetrahydropyranyloxy)-heptylphosphonate

Under an atmosphere of nitrogen, a solution of 4.2 g. of dimethyl 2-oxo-7-(2-tetrahydropyranyloxy)-heptylphosphonate (prepared as described above) in 15 ml. of tetrahydrofuran was added to a suspension of 596 mg. of sodium hydride (63% content) in 20 ml. of tetrahydrofuran at room temperature, and the mixture was stirred at the same temperature for 30 minutes. After cooling to 0° C., 14 ml. of a 1.3M solution of n-butyllithium in n-hexane were added to the solution and the mixture was stirred at 0° C. for 30 minutes. After cooling the solution to −78° C., there was added a solution of 3.23 g. of benzenesulphonyl chloride in 10 ml. of tetrahydrofuran. The mixture was stirred at −78° C. for one hour and then at room temperature for one hour. The reaction mixture was acidified to pH 3 with acetic acid and concentrated under reduced pressure. The residue was dissolved in ethyl acetate, washed with water, dried over sodium sulphate and concentrated under reduced pressure. The residue was purified by column chromatography on silica gel using a mixture of ethyl acetate and benzene (5:1) as eluent to give 2.97 g. of the title compound having the following physical characteristics:-

TLC (developing solvent, ethyl acetate): Rf = 0.25;

IR (liquid film): ν; 1720, 1440, 1348, 1225, 1180, 1130, 1118, 1025, 862, 810 cm$^{-1}$;

NMR (CDCl$_3$ solution): δ; 4.75–4.20 (2H, m), 3.84 (6H, d), 4.10–3.15 (6H, m).

REFERENCE EXAMPLE 28

Methyl 9α-acetoxy-11α,20-bis(2-tetrahydropyranyloxy)-15ξ-hydroxy-16ξ-chloroprost-trans-13-enoate By proceeding as described in Example 1 but replacing the methyl 9α,11α-bis(2-tetrahydropyranyloxy)-15-oxo-16ξ-chloroprosta-cis-5,trans-13-dienoate by 2.96 g. of methyl 9α-acetoxy-11α,20-bis(2-tetrahydropyranyloxy)-15-oxo-16ξ-chloroprost-trans-13-enoate (prepared as described in Reference Example 27) dissolved in 20 ml. of methanol and utilizing 215 mg. of sodium borohydride, there were obtained 2.82 g. of the title compound having the following physical characteristics:-

TLC (developing solvent, benzene-ethyl acetate = 2:1):

Rf = 0.29, 0.25 and 0.18;

IR (liquid film): ν; 3450, 1738, 1438, 1376, 1248, 1138, 1120, 1080, 1038, 1027, 980 cm$^{-1}$;

NMR (CDCl$_3$ solution): δ; 5.75–5.54 (2H, m), 5.22–5.00 (1H, m), 4.76–4.41 (2H, m), 4.41–3.20 (9H, m), 3.66 (3H, s), 2.04 (3H, s).

REFERENCE EXAMPLE 29

Methyl 9α-acetoxy-11α,15ξ,20-tris(2-tetrahydropyranyloxy)-16ξ-chloroprost-trans-13-enoate By proceeding as described in Reference Example 2 but replacing the 15-oxo-PGF$_{2α}$ methyl ester by 2.41 g. of methyl 9α-acetoxy-11α,20-bis(2-tetrahydropyranyloxy)-15ξ-hydroxy-16ξ-chloroprost-trans-13-enoate (prepared as described in Reference Example 28) dissolved in 30 ml. of methylene chloride and utilizing a catalytic amount of p-toluenesulphonic acid and 1.4 ml. of 2,3-dihydropyran, there were obtained 2.594 g. of the title compound having the following physical characteristics:-

TLC (developing solvent, benzene-ethyl acetate = 2:1):

Rf = 0.46;

IR (liquid film): ν; 1738, 1437, 1373, 1352, 1243, 1200, 1133, 1120, 1077, 1033, 1020, 973 cm$^{-1}$;

NMR (CDCl$_3$ solution): δ; 5.75–5.54 (2H, m), 5.22–5.00 (1H, m), 4.77–4.40 (3H, m), 4.40–3.20 (11H, m), 3.66 (3H, s), 2.04 (3H, s).

EXAMPLE 29

Methyl 9α-hydroxy-11α,15ξ,20-tris(2-tetrahydropyranyloxy)16ξ-chloroprost-trans-13-enoate By proceeding as described in Reference Example 11 but replacing the methyl 9α-acetoxy-11α,15ξ-bis(2-tetrahydropyranyloxy)-16ξ-chloroprosta-cis-5,trans-13-dienoate by 2.56 g. of methyl 9α-acetoxy-11α,15ξ,20-tris(2-tetrahydropyranyloxy)-16ξ-chloroprost-trans-13enoate (prepared as described in Reference Example 29) dissolved in 35 ml of methanol and utilizing 712 mg. of potassium carbonate, there were obtained 2.2 g. of the title compound having the following physical characteristics:-

TLC (developing solvent, benzene-ethyl acetate = 2:1):

Rf = 0.27;

IR (liquid film): ν; 3470, 1740, 1438, 1355, 1261, 1200, 1137, 1120, 1079, 1037, 1023, 977 cm$^{-1}$;

NMR (CDCl$_3$ solution): δ; 5.74–5.34 (2H, m), 4.86–4.42 (3H, m), 4.30–3.18 (12H, m), 3.64 (3H, s).

EXAMPLE 30

Methyl 9oxo-11α,15ξ,20-tris(2-tetrahydropyranyloxy)-16ξ-chloroprost-trans-13-enoate by proceeding as described in Example 3 but replacing the methyl 9α-hydroxy-11α,15α-bis(trimethylsilyloxy)-16ξ-chloroprosta-cis-5,trans-13-dienoate by 2.2 g. of methyl 9α-hydroxy-11α,15ξ,20-tris(2-tetrahydropyranyloxy)-16ξ-chloroprost-trans-13-enoate (prepared as described in Example 29) dissolved in 15 ml. of toluene and utilizing a suspension of 2.62 g. of N-chlorosuccinimide in 15 ml. of toluene, 1.93 g. of dimethyl sulphide and 3.88 g. of triethylamine, there were obtained 2.19 g. of the title compound having the following physical characteristics:-

TLC (developing solvent, benzene-ethyl acetate = 2:1):
Rf = 0.38;
IR (liquid film): ν; 1740, 1438, 1355, 1261, 1200, 1135, 1120, 1080, 1037, 1022, 975 cm$^{-1}$;
NMR (CDCl$_3$ solution): δ; 5.88–5.50 (2H, m), 4.88–4.44 (3H, m), 4.38–3.20 (11H, m), 3.66 (3H, s).

EXAMPLE 31

Methyl 9-oxo-11α,15α,20-trihydroxy-16ξ-chloroprost-trans13-enoate [or 16ξ-chloro-20-hydroxy-PGE$_1$ methyl ester]

By proceeding as described in Example 2 but replacing the methyl 9α,11α-bis(2-tetrahydropyranyloxy)-15ξ-hydroxy-16ξ-chloroprosta-cis-5,trans-13-dienoate by 2.17 g. of methyl 9-oxo-11α,15ξ,20-tris(2-tetrahydropyranyloxy)-16ξ-chloroprost-trans-13-enoate (prepared as described in Example 30) dissolved in a mixture of 5 ml. of tetrahydrofuran and 30 ml. of 65% aqueous acetic acid, there were obtained 532 mg. of the title compound and 299 mg. of its 15β-hydroxy isomer. The title compound showed the following physical characteristics:-

TLC (developing solvent, ethyl acetate-methanol = 95:5):
Rf = 0.24 and 0.20, (15β-hydroxy isomer, Rf = 0.27);
IR (liquid film): ν; 3400, 1740, 1438, 1250, 1165, 1075, 978 cm$^{-1}$;
NMR (CDCl$_3$ solution): δ; 5.82–5.60 (2H, m), 4.34–3.82 (3H, m), 3.74–3.46 (2H, m), 3.65 (3H, s), 2.74 (1H, dd).

EXAMPLE 32

Methyl 9-oxo-11α,15α,15α-dihydroxy-16ξ-chloro-20-(p-toluenesulphonyloxy)prost-trans-13-enoate To a solution of 262 mg. of methyl 9-oxo-11α,15α,20-trihydroxy-16ξ-chloroprost-trans-13-enoate (prepared as described in Example 31) in 5 ml. of methylene chloride were added 0.11 ml. of pyridine and 262 mg. of tosyl chloride at 0° C., and the mixture was stirred at the same temperature for 6 hours and then overnight at room temperature. The reaction mixture was diluted with 50 ml. of ethyl acetate, washed with dilute hydrochloric acid, an aqueous solution of sodium bicarbonate and an aqueous solution of sodium chloride, dried over sodium sulphate and concentrated under reduced pressure. The residue was purified by column chromatography on silica gel using a mixture of benzene and ethyl acetate (3:1) as eluent to give 234 mg. of the title compound having the following physical characteristics:-

TLC (developing solvent, ethyl acetate): Rf = 0.44;
IR (liquid film): ν; 3450, 1740, 1600, 1440, 1362, 1250, 1190, 1180, 1100, 1050, 975, 940, 820 cm$^{-1}$;
NMR (CDCl$_3$ solution): δ; 7.89–7.68 (2H, m), 6.44–6.16 (2H, m), 5.83–5.61 (2H, m), 4.38–3.76 (5H, m), 3.66 (3H, s), 2.46 (3H, s).

EXAMPLE 33

Methyl 9-oxo-11α,15α-dihydroxy-16ξ,20-dichloroprost-trans-13-enoate [or 16ε,20-dichloro-PGE$_1$ methyl ester]

To a solution of 221 mg. of methyl 9-oxo-11α,15α-dihydroxy-16ξ-chloro-20-(p-toluenesulphonyloxy)-prosttrans-13-enoate (prepared as described in Example 32) in 10 ml. of N,N-dimethylformamide were added 33 mg. of lithium chloride and the mixture was stirred overnight at room temperature. The reaction mixture was then diluted with 50 ml. of ethyl acetate, washed with water and an aqueous solution of sodium chloride, dried over sodium sulphate and concentrated under reduced pressure. The residue was purified by column chromatography on silica gel using a mixture of benzene and ethyl acetate (3:1) as eluent to give 118 mg. of the title compound having the following physical characteristics:-

TLC (developing solvent, ethyl acetate): Rf = 0.44;
IR (liquid film): ν; 3420, 1733, 1435, 1248, 1162, 1077, 975 cm$^1$;
NMR (CDCl$_3$ solution): δ; 5.71–5.64 (2H, m), 4.84–3.74 (3H, m), 3.74–3.42 (2H, m), 3.64 (3H, s), 2.74 (1H, dd).

EXAMPLE 34

9α-Hydroxy-11α,15α-bis(2-tetrahydropyranyloxy)-16ξ-chloroprosta-cis-5,trans-13-dienoic acid To a solution of 330 mg. of methyl 9α-hydroxy-11α,15α-bis(2-tetrahydropyranyloxy)-16ξ-chloroprostacis-5,trans-13-dienoate (prepared as described in Example 7) in 3 ml. of methanol was added 1 ml. of a 50% aqueous solution of potassium hydroxide and the mixture was stirred at room temperature for 20 minutes. The reaction mixture was then acidified to pH 4 with a saturated aqueous solution of oxalic acid and extracted with ethyl acetate. The extract was washed with water and an aqeuous solution of sodium chloride, dried over sodium sulphate and concentrated under reduced pressure. The residue was purified by column chromatography on silica gel using a mixture of benzene and acetate (1:1) as eluent to give 260 mg. of the title compound having the following physical characteristics:-

TLC (developing solvent, ethyl acetate-benzene = 2:1):
Rf = 0.31;
IR (liquid film): ν; 3450, 1710, 1432, 1350, 1240, 1200, 1130, 1112, 1075, 1020, 975 cm$^{-1}$.

EXAMPLE 35

9α,11α,15α-Trihydroxy-16ξ-chloroprosta-cis-5,trans-13-dienoic acid [or 16ε-chloro-PGF$_{2α}$]

To a solution of 260 mg. of 9α-hydroxy-11α,15α-bis(2-tetrahydropyranyloxy)-16ξ-chloroprosta-cis-5,trans13-dienoic acid (prepared as described in Example 34) in 4 ml. of methanol were added 20 mg. of p-toluenesulphonic acid, and the mixture was stirred at room temperature for 30 minutes. The reaction mixture was concentrated under reduced pressure and the residue was purified by column chromatography on silica gel using ethyl acetate as eluent to give 100 mg. of the title compound having the following physical characteristics:-

TLC (developing solvent, ethyl acetate-methanol = 95:5): Rf = 0.23;
IR (liquid film): $\nu$; 3380, 1710, 1408, 1242, 1050, 973 cm$^{-1}$;
NMR (CDCl$_3$ solution): $\delta$; 5.74–5.52 (2H, m), 5.52–5.25 (2H, m), 4.27–3.75 (4H, m).

EXAMPLE 36

Methyl 9-oxo-11$\alpha$,15$\alpha$-dihydroxy-16$\xi$-chloroprostanoate

[or 16$\epsilon$-chloro-13,14-dihydro-PGE$_1$ methyl ester]

By proceeding as described in Example 10 but replacing the methyl 9$\alpha$-hydroxy-11$\alpha$,15$\alpha$-bis(2-tetrahydropyranyloxy)-16$\xi$-chloroprosta-cis-5,trans-13-dienoate by 78 mg. of methyl 9-oxo-11$\alpha$,15$\alpha$-dihydroxy-16$\xi$-chloroprosta-cis-5,trans-13-dienoate (prepared as described in Example 4) dissolved in 3 ml. of methanol and utilizing 30 mg. of 5% palladium on charcoal, there was obtained a crude product. The crude product was purified by column chromatography on silica gel using a mixture of benzene and ethyl acetate (2:1) as eluent to give 66 mg. of the title compound having the following physical characteristics:-

TLC (developing solvent, ethyl acetate): Rf = 0.52;
IR (liquid film): $\nu$; 3650–3100, 1740, 1720, 1438, 1242, 1200, 1170, 1070 cm$^{-1}$;
NMR (CDCl$_3$ solution): $\delta$; 4.3–3.55 (3H, m), 3.67 (3H, s), 2.71 (1H, dd).

The present invention includes within its scope pharmaceutical compositions which comprise at least one pharmacologically active prostaglandin analogue of general formula VII or a cyclodextrin clathrate or, when R$^1$ represents a hydrogen atom, a non-toxic salt thereof, together with a pharmaceutical carrier or coating. In clinical practice such novel compounds will normally be administered orally, rectally, vaginally or parenterally.

Solid compositions for oral administration include compressed tablets, pills, dispersible powders, and granules. In such solid compositions one or more of the active compounds is, or are, admixed with at least one inert diluent such as calcium carbonate, potato starch, alginic acid, mannitol or lactose. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as water and liquid paraffin. Besides inert diluents such compositions may also comprise adjuvants, such as wetting and suspending agents, and sweetening, flavouring, perfuming and preserving agents. The compositions according to the invention for oral administration also include capsules of absorbable material such as gelatin containing one or more of the active substances with or without the addition of diluents or excipients.

Solid compositions for rectal administration include suppositories formulated in manner known per se and containing one or more of the active compounds.

Solid compositions for vaginal administration include pessaries formulated in manner known per se and containing one or more of the active compounds.

Preparations according to the invention for parenteral administration include sterile aqueous or non-aqueous solution, suspensions, or emulsions. Examples of non-aqueous solvents or suspending media are propylene glycol, polyethylene glycol, vegetable oils such as olive oil, and injectable organic esters such as ethyl oleate. These compositions may also include adjuvants such as preserving, wetting, emulsifying, and dispersing agents. They may be sterilised, for example, by filtration through a bacteria-retaining filter, by incorporation of sterilising agents in the compositions or by irradiation. They may also be manufactured in the form of sterile solid compositions, which can be dissolved in sterile water or some other sterile injectable medium immediately before use.

The percentage of active ingredient in the compositions of the invention may be varied, it being necessary that it should constitute a proportion such that a suitable dosage for the therapeutic effect desired shall be obtained. Obviously several unit dosage forms may be administered at about the same time. In general, the preparations should normally contain at least 0.025% by weight of active substance when required for administration by injection; for oral administration the preparations will normally contain at least 0.1% by weight of active substance. The dose employed depends upon the desired therapeutic effect, the route of administration and the duration of the treatment.

In the human adult, the doses per person are generally between 0.005 and 5 mg. by oral administration in the treatment of hypertension, between 0.005 and 5 mg. by oral administration in the treatment of disorders of the peripheral circulation, between 0.01 and 50 mg. by oral administration in the prevention and treatment of cerebral thrombosis and myocardial infarction, between 0.0005 and 1 mg. by oral administration in the treatment of gastric ulceration, between 0.00005 and 5 mg. by oral, intravaginal, intrauterine, intravenous, intramuscular and extra-ovular administration in the termination of pregnancy and induction of labour in pregnant female mammals and in the treatment of imparied fertility, in the control of oestrus, contraception and menstrual regulation in female mammals. In domestic female mammals such as cows, mares, sows, ewes and bitches, the doses are generally between 0.01 and 50 mg./animal by intramuscular, subcutaneous, intrauterine, intravaginal and intravenous administration for the synchronisation of oestrus, treatment of impaired fertility and the induction of abortion and labour.

Prostaglandin compounds according to the present invention may be administered orally by any method known per se for administration by inhalation of drugs which are not themselves gaseous under normal conditions of administration. Thus, a solution of the active ingredient in a suitable pharmaceutically-acceptable solvent, for example water, can be nebulized by a mechanical nebulizer, for example a Wright Nebulizer, to give an aerosol of finely divided liquid particles suitable for inhalation. Advantageously, the solution to be nebulized is diluted, and aqueous solutions containing from 0.001 to 5 mg., and preferably 0.01 to 0.5 mg., of active ingredient per ml. of solution are particularly suitable. The solution may contain stabilizing agents such as sodium bisulphite and buffering agents to give it an isotonic character, e.g., sodium chloride, sodium citrate and citric acid.

The active ingredients may also be administered orally by inhalation in the form of aerosols generated from self-propelling pharmaceutical compositions. Compositions suitable for this purpose may be obtained by dissolving or suspending in finely-divided form, preferably micronized to an average particle size of less than 5 microns, the active ingredients in pharmaceutically-acceptable solvents, e.g. ethanol, which are co-solvents assisting in dissolving the active ingredients in the volatile liquid propellants hereinafter described, or pharmaceutically-acceptable suspending or dispersing agents, for example aliphatic alcohols such as oleyl alcohol, and incorporating the solutions or suspensions obtained with pharmaceutically-acceptable volatile liquid propellants, in conventional pressurized packs which may be made of any suitable material, e.g. metal, plastics or glass, adequate to withstand the pressures generated by the volatile propellant in the pack. Pressurized pharmaceutically-acceptable gases, such as nitrogen, may also be used as propellants. The pressurized pack is preferably fitted with a metered valve which dispenses a controlled quantity of the self-propelling aerosol composition as a single dose.

Suitable volatile liquid propellants are known in the art and include fluorochlorinated alkanes containing from one to four, and preferably one or two, carbon atoms, for example dichlorodifluoromethane, dichlorotetrafluoroethane, trichloromonofluoromethane, dichloromonofluoromethane and monochlorotrifluoromethane. Preferably, the vapour pressure of the volatile liquid propellant is between about 25 and 65 pound, and more especially between about 30 and 55 pounds, per square inch gauge at 21° C. As is well-known in the art, volatile liquid propellants of different vapour pressures may be mixed in varying proportions to give a propellant having a vapour pressure appropriate to the production of a satisfactory aerosol and suitable for the chosen container. For example dichlorodifluoromethane (vapour pressure 85 pounds per square inch gauge at 21° C.) and dichlorotetrafluoroethane (vapour pressure 28 pounds per square inch gauge at 21° C.) may be mixed in varying proportions to give propellants having vapour pressures intermediate between those of the two constituents, e.g. a mixture of dichlorofluoromethane and dichlorotetrafluoroethane in the proportions 38:62 respectively by weight has a vapour pressure of 53 pounds per square inch gauge at 21° C.

The self-propelling pharmaceutical compositions may be prepared by dissolving the required quantity of active ingredient in the co-solvent or combining the required quantity of active ingredient with a measured quantity of suspending or dispersing agent. A measured quantity of this composition is then placed in an open container which is to be used as the pressurized pack. The container and its contents are then cooled below the boiling temperature of the volatile propellant to be used. The required quantity of liquid propellant, cooled below its boiling temperature, is then added and the contents of the container mixed. The container is then sealed with the required valve fitting, without allowing the temperature to rise above the boiling temperature of the propellant. The temperature of the sealed container is then allowed to rise to ambient with shaking to ensure complete homogeneity of the contents to give a pressurized pack suitable for generating aerosols for inhalation. Alternatively, the co-solvent solution of the active ingredient or combination of active ingredient and suspending or dispersing agent is placed in the open container, the container sealed with a valve, and the liquid propellant introduced under pressure.

Means for producing self-propelling compositions for generating aerosols for the administration of medicaments are, for example, described in detail in U.S. Pat. Nos. 2,868,691 and 3,095,355.

Preferably, the self-propelling pharmaceutical compositions according to the present invention contain from 0.001 to 5 mg., and more particularly 0.01 to 0.5 mg., of active ingredient per ml. of solution or suspension. It is important that the pH of solutions and suspensions used, according to the present invention, to generate aerosols should be kept within the range 3 to 8 and preferable that they should be stored at or below 4° C., to avoid pharmacological deactivation of the active ingredient.

The following Examples illustrate pharmaceutical compositions according to the invention.

EXAMPLE 37

16ξ-Chloro-PGE$_2$ methyl ester (2 mg.) was dissolved in ethanol (10 ml.), mixed with mannitol (18.5 g.), sieved through a 30-mesh sieve, dried at 30° C. for 90 minutes and again sieved through a 30-mesh sieve. Aerosil (microfine silica; 200 mg.) was added and the powder obtained was machine-filled into one hundred No. 2 hard gelatin capsules to give capsules each containing 20 μg. of 16ξ-chloro-PGE$_2$ methyl ester, which after swallowing of the capsules is released into the stomach.

EXAMPLE 38

16ξ-Chloro-20-hydroxy-PGE$_1$ methyl ester (2 mg) was dissolved in ethanol (10 ml.), mixed with mannitol (18.5 g.), sieved through a 30-mesh sieve, dried at 30° C. for 90 minutes and again sieved through a 30-mesh sieve. Aerosil (microfine silica; 200 mg.) was added and the powder obtained was machine-filled into one hundred No. 2 hard gelatin capsules to give capsules each containing 20 μg. of 16ξ-chloro-20-hydroxy-PGE$_1$ methyl ester, which after swallowing of the capsules is released into the stomach.

We claim:

1. A compound of the formula:

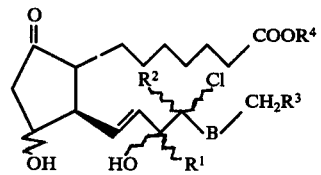

wherein B represents a single bond or a straight- or branched- chain alkylene group containing from 1 to 9 carbon atoms, R$^4$ represents a hydrogen atom or a straight- or branched-chain alkyl group containing from 1 to 12 carbon atoms, R$^1$ represents a hydrogen atom or methyl or ethyl group, R$^2$ represents a hydrogen atom or a methyl or ethyl group and R$^3$ represents a chlorine atom or a hydroxy group and cyclodextrin clathrates of such acids and esters and, when R$^4$ represents a hydrogen atom, non-toxic salts thereof.

2. A compound according to claim 1, wherein B represents the n-propyl group.

3. A compound according to claim 1 wherein -COOR$^4$ represents the carboxy or methoxycarbonyl group.

4. A compound according to claim 1 wherein R$^1$ represents a hydrogen atom or a methyl group.

5. A compound according to claim 1 wherein R$^2$ represents a hydrogen atom or a methyl group.

6. A compound according to claim 1 wherein R$^3$ represents a chlorine atom.

7. A compound according to claim 1 wherein B represents a single bond or a straight- or branched-chain alkylene group containing from 1 to 4 carbon atoms, R$^1$ and R$^2$ represent hydrogen atoms, and R$^3$ represents a chlorine atom.

8. A compound according to claim 1 in which the hydroxy group depicted in formula VII is attached to the carbon atom in α-configuration.

9. A compound according to claim 1 which is methyl 9-oxo-11α,15α,20-trihydroxy-16ξ-chloroprost-trans-13-enoate.

10. A compound according to claim 1 which is methyl 9-oxo-11α,15α-dihydroxy-16ξ,20-dichloroprost-trans-13-enoate.

* * * * *